(12) United States Patent
Wilson et al.

(10) Patent No.: US 7,705,031 B2
(45) Date of Patent: Apr. 27, 2010

(54) BENZIMIDAZOLES USEFUL AS MODULATORS OF ION CHANNELS

(75) Inventors: Dean M. Wilson, San Diego, CA (US); Andreas P. Termin, Encinitas, CA (US); Jesus E. Gonzalez, III, San Diego, CA (US); Nicole Zimmermann, San Diego, CA (US); Yulian Zhang, San Diego, CA (US); Lev T. D. Fanning, San Diego, CA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 11/933,724

(22) Filed: Nov. 1, 2007

(65) Prior Publication Data

US 2008/0306129 A1    Dec. 11, 2008

Related U.S. Application Data

(62) Division of application No. 10/977,609, filed on Oct. 28, 2004, now Pat. No. 7,309,716.

(60) Provisional application No. 60/515,088, filed on Oct. 28, 2003.

(51) Int. Cl.
*A61K 31/4184*    (2006.01)
*A61K 31/165*    (2006.01)

(52) U.S. Cl. ............... 514/394; 514/615; 514/613; 514/617; 548/304.4; 548/304.7; 548/310.1; 548/310.4; 564/161

(58) Field of Classification Search ........... 514/613, 514/617; 548/304.4, 304.7, 310.1, 310.4
See application file for complete search history.

(56) References Cited

U.S. PATENT DOCUMENTS

| 3,162,644 A | 12/1964 | Englisch Alfred et al. |
|---|---|---|
| 4,088,768 A | 5/1978 | Paget et al. |
| 2005/0113283 A1 | 5/2005 | Solow-Cordero et al. |

FOREIGN PATENT DOCUMENTS

| EP | 0563001 A1 | 9/1993 |
|---|---|---|
| WO | 00/59886 A2 | 10/2000 |
| WO | 01/32174 A1 | 5/2001 |
| WO | 00/78728 A1 | 12/2001 |
| WO | 01/96289 A1 | 12/2001 |
| WO | 03/062392 A2 | 7/2003 |

OTHER PUBLICATIONS

Goldin, A. L. (2001) "Resurgence of sodium channel research" Annu Rev Physiol 63: 871-94, cited in the specification.*

De Waard et al. Structural and functional diversity of voltage-activated calcium channels. In Ion Channels, (ed. T. Narahashi) 41-87, (Plenum Press, New York, 1996), cited in the specification.*
Maekawa et al, "Pesticides derived from amino acids," Chemical Abstracts Services, (1984), Database accession No. BRN: 1976:554963.
Walter et al, "Preparation of 2-(alpha.-aminoalkyl)benzimidazoles," Chemical Abstracts Services, (1960), Database Accession No. 1960:80598.
Balboni et al., "Evaluation of Dmt-Tic Pharmacophore: Conversion of a Potent Opioid Receptor Antagonist into a Potent Agonist and Ligands with Mixed Properties," Journal of Medicinal Chemistry 45(3):713-720 (2002).
Rangarajan et al, "2"-substituted 5-phenylterbenzimidazoles as topoisomerase I poisons", Bioorganic & Medicinal Chemistry, 8:1371-1382 (2000).
Database Crossfire Beilstein, Collect. Czech. Chem, Commun. 15:196-200 (1950), Database Accession No. 231224.
Database Crossfire Beilstein, Tetrahedron Letters, 43(16):3003-3006 (2002), Database Accession No. 287207.
Database Crossfire Beilstein, J. Indian Chem. Soc., 53:310-311 (1976), Database Accession No. 924836.
Database Crossfire Beilstein, Indian J. Chem. Sect. A., 15:568 (1977), Database Accession No. 291714.
Database Crossfire Beilstein, Chem. Pharm. Bull., 12:127-129 (1964), Database Accession No. 547537.
Database Crossfire Beilstein, Indian J. Chem. Sect. B., 26:73-74 (1987), Database Accession No. 223899.
Database Crossfire Beilstein, Journal of Medicinal Chemistry, 40(15):2289-2292 (1997), Database Accession No. 7782964.
Database Crossfire Beilstein, Chemical and Pharmaceutical Bulletin, 34(6):2501-2505 (1986), Database Accession No. 5579945.
Database Crossfire Beilstein Mutat. Res. 467(1):41-54 (2000), Database Accession No. 8485329.
Database Crossfire Beilstein, Chem. Heterocycl. Compd., 5:649-650 (1969), Database Accession No. 921882.
Database Crossfire Beilstein, Eur. J. Med. Chem. Chim. Ther., 14:435-438 (1979), Database Accession No. 917933.

* cited by examiner

*Primary Examiner*—Yong Chu
(74) *Attorney, Agent, or Firm*—Wei-Chuan Chen

(57) ABSTRACT

The present invention relates to compounds of Formula I:

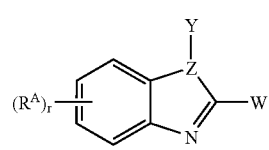

or a pharmaceutically acceptable salt thereof, wherein the $R^1$, Z, Y, $R^4$, and W groups of formula I are as defined herein. The invention also provides pharmaceutically acceptable compositions and methods of using the compositions in the treatment of various disorders.

20 Claims, No Drawings

BENZIMIDAZOLES USEFUL AS MODULATORS OF ION CHANNELS

CROSS-REFERENCE TO RELATED APPLICATIONS

This application is a divisional of U.S. patent application Ser. No. 10/977,609, filed Oct. 28, 2004, now U.S. Pat. No. 7,309,716 titled "BENZIMIDAZOLES USEFUL AS MODULATORS OF ION CHANNELS," which claims the benefit under 35 U.S.C. §119(e) of U.S. provisional application Ser. No. 60/515,088, titled "COMPOSITIONS USEFUL AS INHIBITORS OF VOLTAGE-GATED SODIUM CHANNELS," filed Oct. 28, 2003, the entire contents of each application being incorporated herein by reference.

TECHNICAL FIELD OF THE INVENTION

The present invention relates to compounds useful as inhibitors of voltage-gated sodium channels. The invention also provides pharmaceutically acceptable compositions comprising the compounds of the invention and methods of using the compositions in the treatment of various disorders.

BACKGROUND OF THE INVENTION

Na channels are central to the generation of action potentials in all excitable cells such as neurons and myocytes. They play key roles in excitable tissue including brain, smooth muscles of the gastrointestinal tract, skeletal muscle, the peripheral nervous system, spinal cord and airway. As such they play key roles in a variety of disease states such as epilepsy (See, Moulard, B. and D. Bertrand (2002) "Epilepsy and sodium channel blockers" *Expert Opin. Ther. Patents* 12 (1): 85-91)), pain (See, Waxman, S. G., S. Dib-Hajj, et al. (1999) "Sodium channels and pain" *Proc Natl Acad Sci USA* 96 (14): 7635-9 and Waxman, S. G., T. R. Cummins, et al. (2000) "Voltage-gated sodium channels and the molecular pathogenesis of pain: a review" *J Rehabil Res Dev* 37 (5): 517-28), myotonia (See, Meola, G. and V. Sansone (2000) "Therapy in myotonic disorders and in muscle channelopathies" *Neurol Sci* 21 (5): S953-61 and Mankodi, A. and C. A. Thornton (2002) "Myotonic syndromes" *Curr Opin Neurol* 15 (5): 545-52), ataxia (See, Meisler, M. H., J. A. Kearney, et al. (2002) "Mutations of voltage-gated sodium channels in movement disorders and epilepsy" *Novartis Found Symp* 241: 72-81), multiple sclerosis (See, Black, J. A., S. Dib-Hajj, et al. (2000) "Sensory neuron-specific sodium channel SNS is abnormally expressed in the brains of mice with experimental allergic encephalomyelitis and humans with multiple sclerosis" *Proc Natl Acad Sci USA* 97 (21): 11598-602, and Renganathan, M., M. Gelderblom, et al. (2003) "Expression of Na(v)1.8 sodium channels perturbs the firing patterns of cerebellar purkinje cells" *Brain Res* 959 (2): 235-42), irritable bowel (See, Su, X., R. E. Wachtel, et al. (1999) "Capsaicin sensitivity and voltage-gated sodium currents in colon sensory neurons from rat dorsal root ganglia" *Am J Physiol* 277 (6 Pt 1): G1180-8, and Laird, J. M., V. Souslova, et al. (2002) "Deficits in visceral pain and referred hyperalgesia in Nav1.8 (SNS/PN3)-null mice" *J Neurosci* 22 (19): 8352-6), urinary incontinence and visceral pain (See, Yoshimura, N., S. Seki, et al. (2001) "The involvement of the tetrodotoxin-resistant sodium channel Na(v)1.8 (PN3/SNS) in a rat model of visceral pain" *J Neurosci* 21 (21): 8690-6), as well as an array of psychiatry dysfunctions such as anxiety and depression (See, Hurley, S. C. (2002) "Lamotrigine update and its use in mood disorders" *Ann Pharmacother* 36 (5): 860-73).

Voltage gated Na channels comprise a gene family consisting of 9 different subtypes (NaV1.1-NaV1.9). As shown in Table 1, these subtypes show tissue specific localization and functional differences (See, Goldin, A. L. (2001) "Resurgence of sodium channel research" *Annu Rev Physiol* 63: 871-94). Three members of the gene family (NaV1.8, 1.9, 1.5) are resistant to block by the well-known Na channel blocker TTX, demonstrating subtype specificity within this gene family. Mutational analysis has identified glutamate 387 as a critical residue for TTX binding (See, Noda, M., H. Suzuki, et al. (1989) "A single point mutation confers tetrodotoxin and saxitoxin insensitivity on the sodium channel II" *FEBS Lett* 259 (1): 213-6).

Table 1 (Abbreviations: CNS=central nervous system, PNS=peripheral nervous system, DRG=dorsal root ganglion, TG=Trigeminal ganglion):

| Na isoform | Tissue | TTX IC50 | Indications |
|---|---|---|---|
| NaV1.1 | CNS, PNS soma of neurons | 10 nM | Pain, Epilepsy, neurodegeneration |
| NaV1.2 | CNS, high in axons | 10 nM | Neurodegeneration Epilepsy |
| NaV1.3 | CNS, embryonic, injured nerves | 15 nM | Pain |
| NaV1.4 | Skeletal muscle | 25 nM | Myotonia |
| NaV1.5 | Heart | 2 µM | Arrythmia, long QT |
| NaV1.6 | CNS widespread, most abuntant | 6 nM | Pain, movement disorders |
| NaV1.7 | PNS, DRG, terminals neuroendocrine | 25 nM | Pain, Neuroendocrine disorders |
| NaV1.8 | PNS, small neurons in DRG & TG | >50 µM | Pain |
| NaV1.9 | PNS, small neurons in DRG & TG | 1 µM | Pain |

In general, voltage-gated sodium channels (NaVs) are responsible for initiating the rapid upstroke of action potentials in excitable tissue in nervous system, which transmit the electrical signals that compose and encode normal and aberrant pain sensations. Antagonists of NaV channels can attenuate these pain signals and are useful for treating a variety of pain conditions, including but not limited to acute, chronic, inflammatory, and neuropathic pain. Known NaV antagonists, such as TTX, lidocaine (See, Mao, J. and L. L. Chen (2000) "Systemic lidocaine for neuropathic pain relief" *Pain* 87 (1): 7-17) bupivacaine, phenyloin (See, Jensen, T. S. (2002) "Anticonvulsants in neuropathic pain: rationale and clinical evidence" *Eur J Pain* 6 (Suppl A): 61-8), lamotrigine (See, Rozen, T. D. (2001) "Antiepileptic drugs in the management of cluster headache and trigeminal neuralgia" *Headache* 41 Suppl 1: S25-32 and Jensen, T. S. (2002) "Anticonvulsants in neuropathic pain: rationale and clinical evidence" *Eur J Pain* 6 (Suppl A): 61-8), and carbamazepine (See, Backonja, M. M. (2002) "Use of anticonvulsants for treatment of neuropathic pain" *Neurology* 59 (5 Suppl 2): S14-7), have been shown to be useful attenuating pain in humans and animal models.

Hyperalgesia (extreme sensitivity to something painful) that develops in the presence of tissue injury or inflammation reflects, at least in part, an increase in the excitability of high-threshold primary afferent neurons innervating the site of injury. Voltage sensitive sodium channels activation is critical for the generation and propagation of neuronal action potentials. There is a growing body of evidence indicating that modulation of NaV currents is an endogenous mechanism used to control neuronal excitability (See, Goldin, A. L. (2001) "Resurgence of sodium channel research" *Annu Rev Physiol* 63: 871-94). Several kinetically and pharmacologically distinct voltage-gated sodium channels are found in dorsal root ganglion (DRG) neurons. The TTX-resistant current is insensitive to micromolar concentrations of tetrodotoxin, and displays slow activation and inactivation kinetics and a more depolarized activation threshold when compared to other voltage-gated sodium channels. TTX-resistant sodium currents are primarily restricted to a subpopulation of sensory neurons likely to be involved in nociception. Specifically, TTX-resistant sodium currents are expressed almost exclusively in neurons that have a small cell-body diameter; and give rise to small-diameter slow-conducting axons and that are responsive to capsaicin. A large body of experimental evidence demonstrates that TTX-resistant sodium channels are expressed on C-fibers and are important in the transmission of nociceptive information to the spinal cord.

Intrathecal administration of antisense oligo-deoxynucleotides targeting a unique region of the TTX-resistant sodium channel (NaV1.8) resulted in a significant reduction in $PGE_2$-induced hyperalgesia (See, Khasar, S. G., M. S. Gold, et al. (1998) "A tetrodotoxin-resistant sodium current mediates inflammatory pain in the rat" *Neurosci Lett* 256 (1): 17-20). More recently, a knockout mouse line was generated by Wood and colleagues, which lacks functional NaV1.8. The mutation has an analgesic effect in tests assessing the animal's response to the inflammatory agent carrageenan (See, Akopian, A. N., V. Souslova, et al. (1999) "The tetrodotoxin-resistant sodium channel SNS has a specialized function in pain pathways" *Nat Neurosci* 2 (6): 541-8). In addition, deficit in both mechano- and thermoreception were observed in these animals. The analgesia shown by the Nav1.8 knockout mutants is consistent with observations about the role of TTX-resistant currents in nociception.

Immunohistochemical, in-situ hybridization and in-vitro electrophysiology experiments have all shown that the sodium channel NaV1.8 is selectively localized to the small sensory neurons of the dorsal root ganglion and trigeminal ganglion (See, Akopian, A. N., L. Sivilotti, et al. (1996) "A tetrodotoxin-resistant voltage-gated sodium channel expressed by sensory neurons" *Nature* 379 (6562): 257-62). The primary role of these neurons is the detection and transmission of nociceptive stimuli. Antisense and immunohistochemical evidence also supports a role for NaV1.8 in neuropathic pain (See, Lai, J., M. S. Gold, et al. (2002) "Inhibition of neuropathic pain by decreased expression of the tetrodotoxin-resistant sodium channel, NaV1.8" *Pain* 95 (1-2): 143-52, and Lai, J., J. C. Hunter, et al. (2000) "Blockade of neuropathic pain by antisense targeting of tetrodotoxin-resistant sodium channels in sensory neurons" *Methods Enzymol* 314: 201-13). NaV1.8 protein is upregulated along uninjured C-fibers adjacent to the nerve injury. Antisense treatment prevents the redistribution of NaV1.8 along the nerve and reverses neuropathic pain. Taken together the gene-knockout and antisense data support a role for NaV1.8 in the detection and transmission of inflammatory and neuropathic pain.

In neuropathic pain states there is a remodeling of Na channel distribution and subtype. In the injured nerve, expression of NaV1.8 and NaV1.9 are greatly reduced whereas expression of the TTX sensitive subunit NaV1.3 is 5-10 fold upregulated (See, Dib-Hajj, S. D., J. Fjell, et al. (1999) "Plasticity of sodium channel expression in DRG neurons in the chronic constriction injury model of neuropathic pain." *Pain* 83 (3): 591-600). The timecourse of the increase in NaV1.3 parallels the appearance of allodynia in animal models subsequent to nerve injury. The biophysics of the NaV1.3 channel is distinctive in that it shows very fast repriming after inactivation following an action potential. This allows for sustained rates of high firing as is often seen in the injured nerve (See, Cummins, T. R., F. Aglieco, et al. (2001) "Nav1.3 sodium channels: rapid repriming and slow closed-state inactivation display quantitative differences after expression in a mammalian cell line and in spinal sensory neurons" *J Neurosci* 21 (16): 5952-61). NaV1.3 is expressed in the central and peripheral systems of man. NaV1.9 is similar to NaV1.8 as it is selectively localized to small sensory neurons of the dorsal root ganglion and trigeminal ganglion (See, Fang, X., L. Djouhri, et al. (2002). "The presence and role of the tetrodotoxin-resistant sodium channel Na(v)1.9 (NaN) in nociceptive primary afferent neurons." *J Neurosci* 22 (17): 7425-33). It has a slow rate of inactivation and left-shifted voltage dependence for activation (See, Dib-Hajj, S., J. A. Black, et al. (2002) "NaN/Nav1.9: a sodium channel with unique properties" *Trends Neurosci* 25 (5): 253-9). These two biophysical properties allow NaV1.9 to play a role in establishing the resting membrane potential of nociceptive neurons. The resting membrane potential of NaV1.9 expressing cells is in the −55 to −50 mV range compared to −65 mV for most other peripheral and central neurons. This persistent depolarization is in large part due to the sustained low-level activation of NaV1.9 channels. This depolarization allows the neurons to more easily reach the threshold for firing action potentials in response to nociceptive stimuli. Compounds that block the NaV1.9 channel may play an important role in establishing the set point for detection of painful stimuli. In chronic pain states, nerve and nerve ending can become swollen and hypersensitive exhibiting high frequency action potential firing with mild or even no stimulation. These pathologic nerve swellings are termed neuromas and the primary Na channels expressed in them are NaV1.8 and NaV1.7 (See, Kretschmer, T., L. T. Happel, et al. (2002) "Accumulation of PN1 and PN3 sodium channels in painful human neuroma-evidence from immunocytochemistry" *Acta Neurochir* (Wien) 144 (8): 803-10; discussion 810). NaV1.6 and NaV1.7 are also expressed in dorsal root ganglion neurons and contribute to the small TTX sensitive component seen in these cells. NaV1.7 in particular my therefore be a potential pain target in addition to it's role in neuroendocrine excitability (See, Klugbauer, N., L. Lacinova, et al. (1995) "Structure and functional expression of a new member of the tetrodotoxin-sensitive voltage-activated sodium channel family from human neuroendocrine cells" *Embo J* 14 (6): 1084-90).

NaV1.1 (See, Sugawara, T., E. Mazaki-Miyazaki, et al. (2001) "Nav1.1 mutations cause febrile seizures associated with afebrile partial seizures." *Neurology* 57 (4): 703-5) and NaV1.2 (See, Sugawara, T., Y. Tsurubuchi, et al. (2001) "A missense mutation of the Na+ channel alpha II subunit gene Na(v) 1.2 in a patient with febrile and afebrile seizures causes channel dysfunction" *Proc Natl Acad Sci USA* 98 (11): 6384-9) have been linked to epilepsy conditions including febrile seizures. There are over 9 genetic mutations in NaV1.1 associated with febrile seizures (See, Meisler, M. H., J. A. Kearney, et al. (2002) "Mutations of voltage-gated sodium channels in movement disorders and epilepsy" *Novartis Found Symp* 241: 72-81)

Antagonists for NaV1.5 have been developed and used to treat cardiac arrhythmias. A gene defect in NaV1.5 that produces a larger noninactivating component to the current has been linked to long QT in man and the orally available local anesthetic mexilitine has been used to treat this condition (See, Wang, D. W., K. Yazawa, et al. (1997) "Pharmacological targeting of long QT mutant sodium channels." *J Clin Invest* 99 (7): 1714-20).

Several Na channel blockers are currently used or being tested in the clinic to treat epilepsy (See, Moulard, B. and D. Bertrand (2002) "Epilepsy and sodium channel blockers" *Expert Opin. Ther. Patents* 12 (1): 85-91); acute (See, Wiffen, P., S. Collins, et al. (2000) "Anticonvulsant drugs for acute and chronic pain" *Cochrane Database Syst Rev* 3), chronic (See, Wiffen, P., S. Collins, et al. (2000) "Anticonvulsant drugs for acute and chronic pain" *Cochrane Database Syst Rev* 3, and Guay, D. R. (2001) "Adjunctive agents in the management of chronic pain" *Pharmacotherapy* 21 (9): 1070-81), inflammatory (See, Gold, M. S. (1999) "Tetrodotoxin-resistant Na+ currents and inflammatory hyperalgesia." *Proc Natl Acad Sci USA* 96 (14): 7645-9), and neuropathic pain (See, Strichartz, G. R., Z. Zhou, et al. (2002) "Therapeutic concentrations of local anaesthetics unveil the potential role of sodium channels in neuropathic pain" *Novartis Found Symp* 241: 189-201, and Sandner-Kiesling, A., G. Rumpold Seitlinger, et al. (2002) "Lamotrigine monotherapy for control of neuralgia after nerve section" *Acta Anaesthesiol Scand* 46 (10): 1261-4); cardiac arrhythmias (See, An, R. H., R. Bangalore, et al. (1996) "Lidocaine block of LQT-3 mutant human Na+ channels" *Circ Res* 79 (1): 103-8, and Wang, D. W., K. Yazawa, et al. (1997) "Pharmacological targeting of long QT mutant sodium channels" *J Clin Invest* 99 (7): 1714-20); neuroprotection (See, Taylor, C. P. and L. S. Narasimhan (1997) "Sodium channels and therapy of central nervous system diseases" *Adv Pharmacol* 39: 47-98) and as anesthetics (See, Strichartz, G. R., Z. Zhou, et al. (2002) "Therapeutic concentrations of local anaesthetics unveil the potential role of sodium channels in neuropathic pain." *Novartis Found Symp* 241: 189-201).

Various animal models with clinical significance have been developed for the study of sodium channel modulators for numerous different pain indications. E.g., malignant chronic pain, see, Kohase, H., et al., Acta Anaesthesiol Scand. 2004; 48 (3):382-3; femur cancer pain (see, Kohase, H., et al., Acta Anaesthesiol Scand. 2004; 48 (3):382-3); non-malignant chronic bone pain (see, Ciocon, J. O. et al., J Am Geriatr Soc. 1994; 42 (6):593-6); rheumatoid arthritis (see, Calvino, B. et al., Behav Brain Res. 1987; 24 (1):11-29); osteoarthritis (see, Guzman, R. E., et al., Toxicol Pathol. 2003; 31 (6):619-24); spinal stenosis (see, Takenobu, Y. et al., J Neurosci Methods. 2001; 104 (2):191-8); Neuropathic low back pain (see, Hines, R., et al., Pain Med. 2002; 3 (4):361-5; Massie, J. B., et al., J Neurosci Methods. 2004; 137 (2):283-9; neuropathic low back pain (see, Hines, R., et al., Pain Med. 2002; 3 (4):361-5; Massie, J. B., et al., J Neurosci Methods. 2004; 137 (2):283-9); myofascial pain syndrome (see, Dalpiaz & Dodds, J Pain Palliat Care Pharmacother. 2002; 16 (1):99-104; Sluka K A et al., Muscle Nerve. 2001; 24 (1):37-46); fibromyalgia (see, Bennet & Tai, Int J Clin Pharmacol Res. 1995; 15 (3):115-9); temporomandibular joint pain (see, Ime H, Ren K, Brain Res Mol Brain Res. 1999; 67 (1):87-97); chronic visceral pain, including, abdominal (see, Al-Chaer, E. D., et al., Gastroenterology. 2000; 119 (5):1276-85); pelvic/perineal pain, (see, Wesselmann et al., Neurosci Lett. 1998; 246 (2):73-6); pancreatic (see, Vera-Portocarrero, L. B., et al., Anesthesiology. 2003; 98 (2):474-84); IBS pain (see, Verne, G. N., et al., Pain. 2003; 105 (1-2):223-30; La J H et al., World Gastroenterol. 2003; 9 (12):2791-5); chronic headache pain (see, Willimas & Stark, Cephalalgia. 2003; 23 (10):963-71); migraine (see, Yamamura, H., et al., J Neurophysiol. 1999; 81 (2):479-93); tension headache, including, cluster headaches (see, Costa, A., et al., Cephalalgia. 2000; 20 (2):85-91); chronic neuropathic pain, including, post-herpetic neuralgia (see, Attal, N., et al., Neurology. 2004; 62 (2):218-25; Kim & Chung 1992, Pain 50:355); diabetic neuropathy (see, Beidoun A et al., Clin J Pain. 2004; 20 (3):174-8; Courteix, C., et al., Pain. 1993; 53 (1):81-8); HIV-associated neuropathy (see, Portegies & Rosenberg, Ned Tijdschr Geneeskd. 2001; 145 (15):731-5; Joseph E K et al., Pain. 2004; 107 (1-2):147-58; Oh, S. B., et al., J Neurosci. 2001; 21 (14):5027-35); trigeminal neuralgia (see, Sato, J., et al., Oral Surg Oral Med Oral Pathol Oral Radiol Endod. 2004; 97 (1):18-22; Imamura Y et al., Exp Brain Res. 1997; 116 (1):97-103); Charcot-Marie Tooth neuropathy (see, Sereda, M., et al., Neuron. 1996; 16 (5):1049-60); hereditary sensory neuropathies (see, Lee, M. J., et al., Hum Mol Genet. 2003; 12 (15):1917-25); peripheral nerve injury (see, Attal, N., et al., Neurology. 2004; 62 (2):218-25; Kim & Chung 1992, Pain 50:355; Bennett & Xie, 1988, Pain 33:87; Decostered, I. & Woolf, C. J., 2000, Pain 87:149; Shir, Y. & Seltzer, Z. 1990; Neurosci Lett 115:62); painful neuromas (see, Nahabedian & Johnson, Ann Plast Surg. 2001; 46 (1):15-22; Devor & Raber, Behav Neural Biol. 1983; 37 (2): 276-83); ectopic proximal and distal discharges (see, Liu, X. et al., Brain Res. 2001; 900 (1):119-27); radiculopathy (see, Devers & Galer, (see, Clin J Pain. 2000; 16 (3):205-8; Hayashi N et al., Spine. 1998; 23 (8):877-85); chemotherapy induced neuropathic pain (see, Aley, K. O., et al., Neuroscience. 1996; 73 (1):259-65); radiotherapy-induced neuropathic pain; post-mastectomy pain (see, Devers & Galer, Clin J Pain. 2000; 16 (3):205-8; central pain (Cahana, A., et al., Anesth Analg. 2004; 98 (6):1581-4), spinal cord injury pain (see, Hains, B. C., et al., Exp Neurol. 2000; 164 (2):426-37); post-stroke pain; thalamic pain (see, LaBuda, C. J., et al., Neurosci Lett. 2000; 290 (1):79-83); complex regional pain syndrome (see, Wallace, M. S., et al., Anesthesiology. 2000; 92 (1):75-83; Xantos D et al., J Pain. 2004; 5 (3 Suppl 2):S1); phantom pain (see, Weber, W. E., Ned Tijdschr Geneeskd. 2001; 145 (17):813-7; Levitt & Heyback, Pain. 1981; 10 (1):67-73); intractable pain (see, Yokoyama, M., et al., Can J Anaesth. 2002; 49 (8):810-3); acute pain, acute post-operative pain (see, Koppert, W., et al., Anesth Analg. 2004; 98 (4):1050-5; Brennan, T. J., et al., Pain. 1996; 64 (3):493-501); acute musculoskeletal pain; joint pain (see, Gotoh, S., et al., Ann Rheum Dis. 1993; 52 (11):817-22); mechanical low back pain (see, Kehl, L. J., et al., Pain. 2000; 85 (3):333-43); neck pain; tendonitis; injury/exercise pain (see, Sesay, M., et al., Can J Anaesth. 2002; 49 (2):137-43); acute visceral pain, including, abdominal pain; pyelonephritis; appendicitis; cholecystitis; intestinal obstruction; hernias; etc (see, Giambernardino, M. A., et al., Pain. 1995; 61 (3):459-69); chest pain, including, cardiac Pain (see, Vergona, R. A., et al., Life Sci. 1984; 35 (18):1877-84); pelvic pain, renal colic pain, acute obstetric pain, including, labor pain (see, Segal, S., et al., Anesth Analg. 1998; 87 (4):864-9); cesarean section pain; acute inflammatory, burn and trauma pain; acute intermittent pain, including, endometriosis (see, Cason, A. M., et al., Horm Behav. 2003; 44 (2):123-31); acute herpes zoster pain; sickle cell anemia; acute pancreatitis (see, Toma, H; Gastroenterology. 2000; 119 (5):1373-81); breakthrough pain; orofacial pain, including, sinusitis pain, dental pain (see, Nusstein, J., et al., J Endod. 1998; 24 (7):487-91; Chidiac, J. J., et al., Eur J Pain. 2002; 6 (1):55-67); multiple sclerosis (MS) pain (see, Sakurai & Kanazawa, J Neurol Sci. 1999; 162 (2):162-8); pain in depression (see, Greene B, Curr Med Res Opin. 2003; 19 (4):272-7); leprosy pain; behcet's disease pain; adiposis dolorosa (see, Devillers & Oranje, Clin Exp Dermatol. 1999; 24 (3):240-1); phlebitic pain; Guillain-Barre pain; painful legs and moving toes; Haglund syndrome; erythromelalgia pain (see, Legroux-Crespel, E., et al., Ann Dermatol Venereol. 2003; 130 (4):429-33); Fabry's disease pain (see, Germain, D. P., J Soc Biol. 2002; 196 (2):183-90); Bladder and urogenital disease, including, urinary incontinence (see, Berggren, T., et al., J Urol. 1993; 150 (5 Pt 1):1540-3); hyperactivity bladder (see, Chuang, Y. C., et al., Urology. 2003; 61 (3):664-70); painful bladder syndrome (see, Yoshimura, N., et al., J Neurosci. 2001; 21 (21):8690-6); interstitial cyctitis (IC) (see, Giannakopoulos & Campilomatos, Arch Ital Urol Nefrol Androl. 1992; 64 (4):337-9; Boucher, M., et al., J Urol. 2000; 164 (1):203-8); and prostatitis (see, Mayersak, J. S., Int Surg. 1998; 83 (4):347-9; Keith, I. M., et al., J Urol. 2001; 166 (1):323-8).

Voltage-gated calcium channels are membrane-spanning, multi-subunit proteins that open in response to membrane depolarization, allowing Ca entry from the extracellular milieu. Calcium channels were initially classified based on the time and voltage-dependence of channel opening and on the sensitivity to pharmacological block. The categories were low-voltage activated (primarily T-type) and high-voltage activated (L, N, P, Q or R-type). This classification scheme was replaced by a nomenclature based upon the molecular subunit composition, as summarized in Table I (Hockerman, G. H., et. al. (1997) *Annu. Rev. Pharmacol. Toxicol.* 37: 361-96; Striessnig, J. (1999) *Cell. Physiol. Biochem.* 9: 242-69). There are four primary subunit types that make up calcium channels—$\alpha_1$, $\alpha_2\delta$, $\beta$ and $\gamma$ (See, e.g., De Waard et al. Structural and functional diversity of voltage-activated calcium channels. In Ion Channels, (ed. T. Narahashi) 41-87, (Plenum Press, New York, 1996)). The $\alpha_1$ subunit is the primary determinant of the pharmacological properties and contains the channel pore and voltage sensor (Hockerman, G. H., et. al. (1997) *Annu. Rev. Pharmacol. Toxicol.* 37: 361-96; Striessnig, J. (1999) *Cell. Physiol. Biochem.* 9: 242-69). Ten isoforms of the $\alpha_1$ subunit are known, as indicated in Table I. The $\alpha_2\delta$ subunit consists of two disulfide linked subunits, $\alpha_2$, which is primarily extracellular and a transmembrane $\delta$ subunit. Four isoforms of $\alpha_2\delta$ are known, $\alpha_2\delta$-1, $\alpha_2\delta$-2, $\alpha_2\delta$-3 and $\alpha_2\delta$-4. The $\beta$ subunit is a non-glycosylated cytoplasmic protein that binds to the $\alpha_1$ subunit. Four isoforms are known, termed $\beta_1$ to $\beta_4$. The $\gamma$ subunit is a transmembrane protein that has been biochemically isolated as a component of $Ca_v1$ and $Ca_v2$ channels. At least 8 isoforms are known ($\gamma_1$ to $\gamma_8$) (Kang, M. G. and K. P. Campbell (2003) *J. Biol. Chem.* 278: 21315-8). The nomenclature for voltage-gated calcium channels is based upon the content of the $\alpha_1$ subunit, as indicated in Table I. Each type of $\alpha_1$ subunit can associate with a variety of $\beta$, $\alpha_2\delta$ or $\gamma$ subunits, so that each $Ca_v$ type corresponds to many different combinations of subunits.

| Cav Nomenclature | $\alpha_1$ subunit | Pharmacological name |
|---|---|---|
| $Ca_v1.1$ | $\alpha_{1S}$ | L-type |
| $Ca_v1.2$ | $\alpha_{1C}$ | L-type |
| $Ca_v1.3$ | $\alpha_{1D}$ | L-type |
| $Ca_v1.4$ | $\alpha_{1F}$ | |
| $Ca_v2.1$ | $\alpha_{1A}$ | P- or Q-type |
| $Ca_v2.2$ | $\alpha_{1B}$ | N-type |
| $Ca_v2.3$ | $\alpha_{1E}$ | R-type |
| $Ca_v3.1$ | $\alpha_{1G}$ | T-type |
| $Ca_v3.2$ | $\alpha_{1H}$ | T-type |
| $Ca_v3.3$ | $\alpha_{1I}$ | T-type |

$Ca_v2$ currents are found almost exclusively in the central and peripheral nervous system and in neuroendocrine cells and constitute the predominant forms of presynaptic voltage-gated calcium current. Presynaptic action potentials cause channel opening and neurotransmitter release is steeply dependent upon the subsequent calcium entry. Thus, $Ca_v2$ channels play a central role in mediating neurotransmitter release.

$Ca_v2.1$ and $Ca_v2.2$ contain high affinity binding sites for the peptide toxins ω-conotoxin-MVIIC and ω-conotoxin-GVIA, respectively, and these peptides have been used to determine the distribution and function of each channel type. $Ca_v2.2$ is highly expressed at the presynaptic nerve terminals of neurons from the dorsal root ganglion and neurons of lamina I and II of the dorsal horn (Westenbroek, R. E., et al. (1998) *J. Neurosci.* 18: 6319-30; Cizkova, D, et al. (2002) *Exp. Brain Res.* 147: 456-63). $Ca_v2.2$ channels are also found in presynaptic terminals between second and third order interneurons in the spinal cord. Both sites of neurotransmission are very important in relaying pain information to the brain.

Pain can be roughly divided into three different types: acute, inflammatory, and neuropathic. Acute pain serves an important protective function in keeping the organism safe from stimuli that may produce tissue damage. Severe thermal, mechanical, or chemical inputs have the potential to cause severe damage to the organism if unheeded. Acute pain serves to quickly remove the individual from the damaging environment. Acute pain by its very nature generally is short lasting and intense. Inflammatory pain, on the other hand, may last for much longer periods of time and its intensity is more graded. Inflammation may occur for many reasons including tissue damage, autoimmune response, and pathogen invasion. Inflammatory pain is mediated by a variety of agents that are released during inflammation, including substance P, histamines, acid, prostaglandin, bradykinin, CGRP, cytokines, ATP, and other agents (Julius, D. and A. I. Basbaum (2001) *Nature* 413 (6852): 203-10). The third class of pain is neuropathic and involves nerve damage arising from nerve injury or viral infection and results in reorganization of neuronal proteins and circuits yielding a pathologic "sensitized" state that can produce chronic pain lasting for years. This type of pain provides no adaptive benefit and is particularly difficult to treat with existing therapies.

Pain, particularly neuropathic and intractable pain is a large unmet medical need. Millions of individuals suffer from severe pain that is not well controlled by current therapeutics. The current drugs used to treat pain include NSAIDS, COX-2 inhibitors, opioids, tricyclic antidepressants, and anticonvulsants. Neuropathic pain has been particularly difficult to treat as it does not respond well to opioids until high doses are reached. Gabapentin is currently the most widely used therapeutic for the treatment of neuropathic pain, although it works in only 60% of patients and has modest efficacy. The drug is generally safe, although sedation is an issue at higher doses.

Validation of Cav2.2 as a target for the treatment of neuropathic pain is provided by studies with ziconotide (also known as ω-conotoxin-MVIIA), a selective peptide blocker of this channel (Bowersox, S. S., et al. (1996) *J. Pharmacol. Exp. Ther.* 279: 1243-9; Jain, K. K. (2000) *Exp. Opin. Invest. Drugs* 9: 2403-10; Vanegas, H. and H. Schaible (2000) *Pain* 85: 9-18). In man, intrathecal infusion of Ziconotide is effective for the treatment of intractable pain, cancer pain, opioid resistant pain, and neuropathic pain. The toxin has an 85% success rate for the treatment of pain in humans with a greater potency than morphine. An orally available antagonist of $Ca_v2.2$ should have similar efficacy without the need for intrathecal infusion. $Ca_v2.1$ and $Ca_v2.3$ are also in neurons of nociceptive pathways and antagonists of these channels could be used to treat pain.

Antagonists of $Ca_V2.1$, $Ca_V2.2$ or $Ca_V2.3$ should also be useful for treating other pathologies of the central nervous system that apparently involve excessive calcium entry. Cerebral ischaemia and stroke are associated with excessive calcium entry due to depolarization of neurons. The $Ca_V2.2$ antagonist ziconotide is effective in reducing infarct size in a focal ischemia model using laboratory animals, suggesting that $Ca_V2.2$ antagonists could be used for the treatment of stroke. Likewise, reducing excessive calcium influx into neurons may be useful for the treatment of epilepsy, traumatic brain injury, Alzheimer's disease, multi-infarct dementia and other classes of dementia, amyotrophic lateral sclerosis, amnesia, or neuronal damage caused by poison or other toxic substances.

$Ca_V2.2$ also mediates release of neurotransmitters from neurons of the sympathetic nervous system and antagonists could be used to treat cardiovascular diseases such as hypertension, cardiac arrhythmia, angina pectoris, myocardial infarction, and congestive heart failure.

However, as described above, the efficacy of currently used sodium channel blockers and calcium channel blockers for the disease states described above has been to a large extent limited by a number of side effects. These side effects include various CNS disturbances such as blurred vision, dizziness, nausea, and sedation as well more potentially life threatening cardiac arrhythmias and cardiac failure. Accordingly, there remains a need to develop additional Na channel antagonists, and Ca channel antagonists preferably those with higher potency and fewer side effects.

SUMMARY OF THE INVENTION

It has now been found that compounds of this invention, and pharmaceutically acceptable compositions thereof, are useful as inhibitors of voltage-gated sodium channels. These compounds have the structure of Formula I:

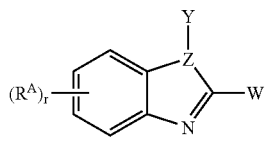

I or a pharmaceutically acceptable salt thereof, wherein $R^A$, Z, Y, r, and W are as defined below.

These compounds and pharmaceutically acceptable compositions are useful for treating or lessening the severity of a variety of diseases, disorders, or conditions, including, but not limited to, acute, chronic, neuropathic, or inflammatory pain such as femur cancer pain; non-malignant chronic bone pain; rheumatoid arthritis; osteoarthritis; spinal stenosis; neuropathic low back pain; neuropathic low back pain; myofascial pain syndrome; fibromyalgia; temporomandibular joint pain; chronic visceral pain, including, abdominal; pancreatic; IBS pain; chronic headache pain; migraine; tension headache, including, cluster headaches; chronic neuropathic pain, including, post-herpetic neuralgia; diabetic neuropathy; HIV-associated neuropathy; trigeminal neuralgia; Charcot-Marie Tooth neuropathy; hereditary sensory neuropathies; peripheral nerve injury; painful neuromas;

ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome; phantom pain; intractable pain; acute pain, acute post-operative pain; acute musculoskeletal pain; joint pain; mechanical low back pain; neck pain; tendonitis; injury/exercise pain; acute visceral pain, including, abdominal pain; pyelonephritis; appendicitis; cholecystitis; intestinal obstruction; hernias; etc; chest pain, including, cardiac Pain; pelvic pain, renal colic pain, acute obstetric pain, including, labor pain; cesarean section pain; acute inflammatory, burn and trauma pain; acute intermittent pain, including, endometriosis; acute herpes zoster pain; sickle cell anemia; acute pancreatitis; breakthrough pain; orofacial pain, including, sinusitis pain, dental pain; multiple sclerosis (MS) pain; pain in depression; leprosy pain; behcet's disease pain; adiposis dolorosa; phlebitic pain; Guillain-Barre pain; painful legs and moving toes; Haglund syndrome; erythromelalgia pain; Fabry's disease pain; bladder and urogenital disease, including, urinary incontinence; hyperactivity bladder; painful bladder syndrome; interstitial cyctitis (IC); or prostatitis, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, and incontinence.

DETAILED DESCRIPTION OF THE INVENTION

1. General Description of Compounds of the Invention

The present invention provides a compound of Formula I:

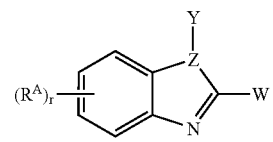

I or a pharmaceutically acceptable salt thereof, wherein:

r is 0 to 4;

Z is O, N or CH;

Y and W are independently selected from hydrogen, Formula Ia:

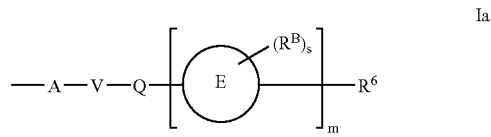

Ia wherein:

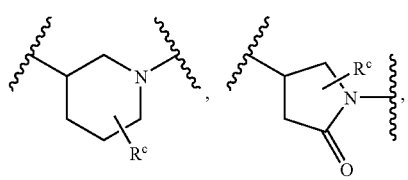

-continued

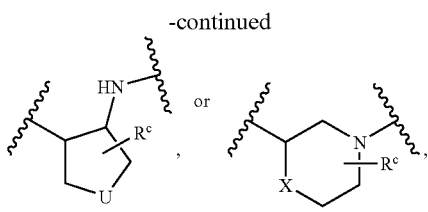

A is -T-NH—,
wherein:
T is a bond or a $C_{1-6}$ straight or branched aliphatic chain wherein a methylene unit of T is optionally replaced by a $C_{3-8}$ cycloaliphatic group;
U is —$CH_2$— or —$CH_2$—$CH_2$—;
X is N—$C_{1-4}$alkyl, NH, O, S, S(O), or $SO_2$; and
each occurrence of $R^C$ is independently M-$R^X$;
wherein:
M is a bond or is a $C_{1-6}$ alkylidene chain wherein up to two non-adjacent methylene units of M are optionally replaced by C(O), $CO_2$, C(O)C(O), C(O)NR, OC(O)NR, NRNR, NRNRC(O), NRC(O), $NRCO_2$, NRC(O)NR, S(O), $SO_2$, $NRSO_2$, $SO_2NR$, $NRSO_2NR$, O, S, or NR, and
$R^X$ is R', halogen, $NO_2$, or CN; wherein:
each occurrence of R' is independently selected from hydrogen or an optionally substituted group selected from $C_{1-8}$ aliphatic, $C_{6-10}$ aryl, a heteroaryl ring having 5-10 ring atoms, or a heterocyclyl ring having 3-10 ring atoms, or R and R' taken together with the atom(s) to which they are bound, or two occurrences of R' taken together with the atom(s) to which they are bound, form a 5-8 membered cycloalkyl, heterocyclyl, aryl, or heteroaryl ring having 0-3 heteroatoms independently selected from nitrogen, oxygen, or sulfur;
V is a bond, —C(O)—, or —$S(O)_2$—;
Q is a bond or a $C_{1-4}$ alkylidene chain wherein up to two non-adjacent methylene units of Q are optionally replaced by —O—, —NH—, or —S—;
m is 0 or 1;
Ring E is $C_{6-10}$ aryl, a 5-10 membered heteroaryl ring having 1-4 heteroatoms independently selected from nitrogen, oxygen, or sulfur, or a 3-10 membered heterocyclyl ring having 1-4 heteroatoms independently selected from nitrogen, oxygen, or sulfur; and
s is 0 to 8;
or Formula Ib:

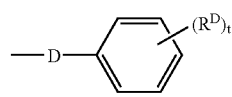

Ib wherein:
D is —$C_{1-6}$alkyl- or a bond; and
t is 0 to 5;
each occurrence of R is independently selected from hydrogen or an optionally substituted $C_{1-6}$ aliphatic group; and
each occurrence of $R^A$, $R^B$ and $R^D$ are independently selected from $R^1$, $R^2$, $R^3$, $R^4$, or $R^5$, wherein:

$R^1$ is oxo, $R^6$ or $(C_{1-4}aliphatic)_n$-J, wherein:
n is 0 or 1;
J is halo, CN, $NO_2$, $CF_3$, $OCF_3$, OH, $SR^6$, $S(O)R^6$, $SO_2R^6$, $NH_2$, $NHR^6$, $N(R^6)_2$, $NR^6R^8$, C(O)OH, C(O)OR$^6$ or OR$^6$; or:
two $R^1$ on adjacent ring atoms, taken together, form 1,2-methylenedioxy or 1,2-ethylenedioxy;
$R^2$ is $C_{1-6}$aliphatic, optionally substituted with up to two substituents independently selected from $R^1$, $R^4$, or $R^5$;
$R^3$ is $C_{3-8}$cycloaliphatic, $C_{6-10}$ aryl, a 5-10 membered heteroaryl ring having 1-4 heteroatoms independently selected from nitrogen, oxygen, or sulfur, or a 3-10 membered heterocyclyl ring having 1-4 heteroatoms independently selected from nitrogen, oxygen, or sulfur, wherein $R^3$ is optionally substituted with up to three substituents independently selected from $R^1$, $R^2$, $R^4$ or $R^5$;
$R^4$ is $OR^5$, $OR^6$, $OC(O)R^6$, $OC(O)R^5$, $OC(O)OR^6$, $OC(O)OR^5$, $OC(O)N(R^6)_2$, $OC(O)N(R^5)_2$, $OC(O)N(R^6R^5)$, $SR^6$, $SR^5$, $S(O)R^6$, $S(O)R^5$, $SO_2R^6$, $SO_2R^5$, $SO_2N(R^6)_2$, $SO_2N(R^5)_2$, $SO_2NR^5R^6$, $SO_3R^6$, $SO_3R^5$, $C(O)R^5$, $C(O)OR^5$, $C(O)R^6$, $C(O)OR^6$, $C(O)N(R^6)_2$, $C(O)N(R^5)_2$, $C(O)N(R^5R^6)$, $C(O)N(OR^6)R^6$, $C(O)N(OR^5)R^6$, $C(O)N(OR^6)R^5$, $C(O)N(OR^5)R^5$, $C(NOR^6)R^6$, $C(NOR^6)R^5$, $C(NOR^5)R^6$, $C(NOR^5)R^5$, $N(R^6)_2$, $N(R^5)_2$, $N(R^5R^6)$, $NR^5C(O)R^5$, $NR^6C(O)R^6$, $NR^6C(O)R^5$, $NR^6C(O)R^6$, $NR^5C(O)OR^6$, $NR^6C(O)OR^5$, $NR^5C(O)OR^5$, $NR^6C(O)N(R^6)_2$, $NR^6C(O)NR^5R^6$, $NR^6C(O)N(R^5)_2$, $NR^5C(O)N(R^6)_2$, $NR^5C(O)NR^5R^6$, $NR^5C(O)N(R^5)_2$, $NR^6SO_2R^6$, $NR^6SO_2R^5$, $NR^5SO_2R^5$, $NR^6SO_2N(R^6)_2$, $NR^6SO_2NR^5R^6$, $NR^6SO_2N(R^5)_2$, $NR^5SO_2NR^5R^6$, $NR^5SO_2N(R^5)_2$, $N(OR^6)R^6$, $N(OR^6)R^5$, $N(OR^5)R^5$, or $N(OR^5)R^6$;
$R^5$ is a $C_{3-8}$cycloaliphatic, $C_{6-10}$ aryl, a 5-10 membered heteroaryl ring having 1-4 heteroatoms independently selected from nitrogen, oxygen, or sulfur, or a 3-10 membered heterocyclyl ring having 1-4 heteroatoms independently selected from nitrogen, oxygen, or sulfur, wherein $R^5$ is optionally substituted with up to three $R^1$ substituents;
$R^6$ is R optionally substituted with $R^7$, wherein:
$R^7$ is a $C_{3-8}$cycloaliphatic, $C_{6-10}$ aryl, a 5-10 membered heteroaryl ring having 1-4 heteroatoms independently selected from nitrogen, oxygen, or sulfur, or a 3-10 membered heterocyclyl ring having 1-4 heteroatoms independently selected from nitrogen, oxygen, or sulfur, wherein $R^7$ is optionally substituted with up to two substituents independently selected from R, 1,2-methylenedioxy, 1,2-ethylenedioxy, or $(CH_2)_n$-G, wherein G is selected from halo, CN, $NO_2$, $CF_3$, $OCF_3$, OH, S-aliphatic, S(O)-aliphatic, $SO_2$-aliphatic, $NH_2$, N-aliphatic, N(aliphatic)$_2$, N(aliphatic)$R^8$, COOH, C(O)O(-aliphatic, or O-aliphatic; and
$R^8$ is an amino protecting group;

provided that only one of Y and W is formula Ia or Ib and the other of Y and W is hydrogen.
In certain other embodiments, for compounds of Formula I as described generally above and herein:
a) when Z is N, W is Formula Ia, A is —$C_2$alkyl-NH—, V is —C(O)—, Q is —$C_1$alkyl-O—, and Ring E is phenyl, then $R^A$ is not hydrogen, —Cl, —Br, $C_{1-4}$alkyl, methoxy, or nitro, either singly or in combination;
b) when Z is N, W is Formula Ia, A is —$C_2$alkyl-NH—, V is —C(O)—, Q is a bond, and Ring E is phenyl, then $R^A$ is not hydrogen, —Cl, —Br, $C_{1-4}$alkyl, methoxy, or nitro, either singly or in combination;

c) when Z is N, W is Formula Ia, A is —C₃alkyl-NH—, V is —C(O)—, Q is a bond, and Ring E is phenyl, then R$^A$ is not 4-amino, or 4-methoxycarbonyl;

d) when Z is N, W is Formula Ia, A is —C₃alkyl-NH—, V is —C(O)—, and Q is a bond, then Ring E is not -2(2,3-dihydro-benzo[1,4]dioxine);

e) when Z is N, W is Formula Ia, A is —C₃alkyl-NH—, V is —C(O)—, and Q is a —C₁alkyl-O—, then Ring E is not -6(4-dimethyl-2H-chromen-2-one);

f) when Z is N, W is Formula Ia, A is —C₂alkyl-NH—, V is —C(O)—, and Q is a —C₂alkyl-O—, then Ring E is not unsubstituted phenyl;

g) when Z is N, W is Formula Ia, A is —C₂alkyl-NH—, V is —C(O)—, and B is a bond, then Ring E is not unsubstituted thienyl;

h) when Z is N, W is Formula Ia, A is —C₂alkyl-NH—, V is —C(O)—, and Q is a —C₁alkyl-O—, and Ring E is phenyl, then R$^A$ is not phenyl at the 4 position;

i) when Z is N, W is Formula Ia, A is —C₂alkyl-NH—, V is —C(O)—, and Q is a —C₂alkyl, then Ring E is not 2-isoindoline-1,3-dione;

j) when Z is N, W is Formula Ia, A is —C₂alkyl-NH—, V is —C(O)—, and Q is a —C₂alkyl-O—, and Ring E is phenyl, then R$^A$ is not phenyl at the 4 position; and k) when Z is N, W is Formula Ia, A is —C₂alkyl-NH—, V is —C(O)—, and Q is a bond, then Ring E is not unsubstituted adamantyl.

According to another embodiment, the present invention provides a compound of formula Ia, as defined generally above, wherein:

(a) when Z is N, Y is hydrogen, W is formula Ia, A is

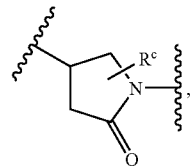

and V and Q are each a bond, then:

(i) when r is 1 and R$^A$ is methyl in the C-5 or C-6 position of the benzimidazole ring, then E is not:
  unsubstituted phenyl;
  phenyl substituted in the ortho position with methyl, OMe, or OEt; or
  phenyl substituted in the para position with OMe or methyl; and (ii) when r is 0, then E is not:
  unsubstituted phenyl;
  unsubstituted naphthyl;
  phenyl substituted in the para position with OEt, Br, OH, or OMe;
  phenyl substituted in the meta position with chloro; or
  phenyl substituted in the ortho position with methyl;

(b) when Z is N, Y is hydrogen, W is formula Ia, Q is —NHCH₂—, r is 0, and V is C(O), then:

(i) when A is —CH₂CH₂NH—, then E is not

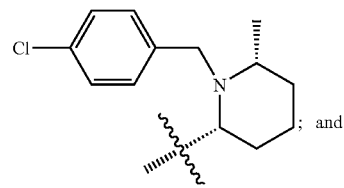

; and (ii) when A is —CH₂NH—, then E is not

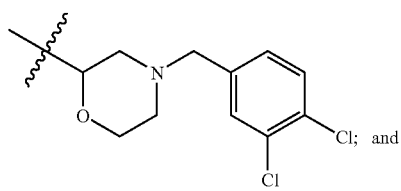

; and (c) when Z is C, W is hydrogen, Y is formula Ia, r is 0, A is —CH₂CH₂NH—, V is C(O), Q is —CH₂O— and E is phenyl, then:

(i) s is not 0;

(ii) when s is 1, R$^B$ is not:
  unsubstituted phenyl, chloro, OMe, methyl, bromo,

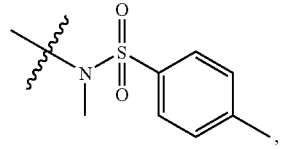

, or

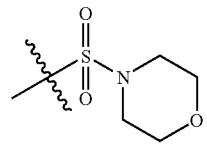

in the para position;
  cyano or OMe in the ortho position; or
  methyl in the meta position;

(iii) when s is 2, R$^B$ is not dichloro in the ortho/para positions; and (iv) when s is 3, R$^B$ is not 2,3,4-trimethoxy or 2,4,5-trichloro.

In certain other embodiments, for compounds of Formula I as described generally above and herein:

a) when Z is N, W is Formula Ia, A is —CH₂CH₂NH—, V is —C(O)—, Q is —CH₂O—, and Ring E is phenyl, then R$^A$ is not —Cl, —Br, C$_{1-4}$alkyl, methoxy, or nitro, either singly or in combination;

b) when Z is N, W is Formula Ia, A is —CH₂CH₂NH—, V is —C(O)—, Q is a bond, and Ring E is phenyl, then R$^A$ is not —Cl, —Br, C$_{1-4}$alkyl, methoxy, or nitro, either singly or in combination;

c) when Z is N, W is Formula Ia, A is —CH$_2$CH$_2$CH$_2$NH—, V is —C(O)—, Q is a bond, and Ring E is phenyl, then R$^A$ is not 4-amino, or 4-methoxycarbonyl;
d) when Z is N, W is Formula Ia, A is —CH$_2$CH$_2$CH$_2$NH—, V is —C(O)—, and Q is a bond, then Ring E is not -2(2,3-dihydro-benzo[1,4]dioxine);
e) when Z is N, W is Formula Ia, A is —CH$_2$CH$_2$CH$_2$NH—, V is —C(O)—, and Q is a —CH$_2$O—, then Ring E is not -6(4-dimethyl-2H-chromen-2-one);
f) when Z is N, W is Formula Ia, A is —CH$_2$CH$_2$NH—, V is —C(O)—, and Q is a —CH$_2$CH$_2$O—, then Ring E is not unsubstituted phenyl;
g) when Z is N, W is Formula Ia, A is —CH$_2$CH$_2$NH—, V is —C(O)—, and Q is a bond, then Ring E is not unsubstituted thienyl;
h) when Z is N, W is Formula Ia, A is —CH$_2$CH$_2$NH—, V is —C(O)—, and Q is a —CH$_2$O—, and Ring E is phenyl, then R$^A$ is not phenyl at the 4 position;
i) when Z is N, W is Formula Ia, A is —CH$_2$CH$_2$NH—, V is —C(O)—, and Q is —CH$_2$CH$_2$—, then Ring E is not 2-isoindoline-1,3-dione;
j) when Z is N, W is Formula Ia, A is —CH$_2$CH$_2$NH—, V is —C(O)—, and Q is —CH$_2$CH$_2$O—, and Ring E is phenyl, then R$^A$ is not phenyl at the 4 position; and
k) when Z is N, W is Formula Ia, A is —CH$_2$CH$_2$NH—, V is —C(O)—, and Q is a bond, then Ring E is not unsubstituted adamantyl.
l) when Z is N, W is Formula Ia, A is —CH$_2$CH$_2$NH—, V is —C(O)—, Q is —CH$_2$CH$_2$O—, and Ring E is phenyl, then R$^B$ is not —Cl, —Br, C$_{1-4}$alkyl, methoxy, unsubstituted phenyl, —C(CH$_3$)$_2$phenyl, or nitro, either singly or in combination;
m) when Z is N, W is Formula Ia, A is —CH$_2$CH$_2$NH—, V is —C(O)—, Q is —CH═CH$_2$—, and Ring E is phenyl, then R$^B$ is not —Cl in the ortho position; and
n) when Z is N, W is Formula Ia, A is —CH$_2$CH$_2$NH—, V is —SO$_2$—, Q is a bond, and Ring E is phenyl, then R$^B$ is not chloro.

Another embodiment of the present invention provides a method of treating or lessening the severity of a disease, disorder, or condition selected from acute, chronic, neuropathic, or inflammatory pain, including femur cancer pain; non-malignant chronic bone pain; rheumatoid arthritis; osteoarthritis; spinal stenosis; neuropathic low back pain; neuropathic low back pain; myofascial pain syndrome; fibromyalgia; temporomandibular joint pain; chronic visceral pain, including, abdominal; pancreatic; IBS pain; chronic headache pain; migraine; tension headache, including, cluster headaches; chronic neuropathic pain, including, post-herpetic neuralgia; diabetic neuropathy; HIV-associated neuropathy; trigeminal neuralgia; Charcot-Marie Tooth neuropathy; hereditary sensory neuropathies; peripheral nerve injury; painful neuromas; ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome; phantom pain; intractable pain; acute pain, acute post-operative pain; acute musculoskeletal pain; joint pain; mechanical low back pain; neck pain; tendonitis; injury/exercise pain; acute visceral pain, including, abdominal pain; pyelonephritis; appendicitis; cholecystitis; intestinal obstruction; hernias; etc; chest pain, including, cardiac Pain; pelvic pain, renal colic pain, acute obstetric pain, including, labor pain; cesarean section pain; acute inflammatory, burn and trauma pain; acute intermittent pain, including, endometriosis; acute herpes zoster pain; sickle cell anemia; acute pancreatitis; breakthrough pain; orofacial pain, including, sinusitis pain, dental pain; multiple sclerosis (MS) pain; pain in depression; leprosy pain; behcet's disease pain; adiposis dolorosa; phlebitic pain; Guillain-Barre pain; painful legs and moving toes; Haglund syndrome; erythromelalgia pain; Fabry's disease pain; bladder and urogenital disease, including, urinary incontinence; hyperactivity bladder; painful bladder syndrome; interstitial cyctitis (IC); or prostatitis; arthritis, migraine, cluster headaches, trigeminal neuralgia, herpetic neuralgia, general neuralgias, epilepsy or an epilepsy condition, a neurodegenerative disorder, a psychiatric disorder such as anxiety and depression, myotonia, arrhythmia, a movement disorder, a neuroendocrine disorder, ataxia, multiple sclerosis, irritable bowel syndrome, or incontinence comprising the step of administering to said patient an effective amount of a compound of Formula I:

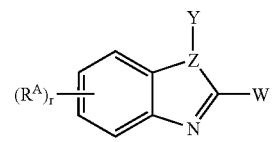

or a pharmaceutically acceptable salt thereof, wherein R$^A$, Z, Y, r, and W are as defined above and in classes and subclasses as described herein.

A preferred aspect of the present embodiment is where the disease, condition, or disorder is acute, chronic, neuropathic, or inflammatory pain.

Another embodiment of the present invention provides a method for treating or lessening the severity of a disease, condition or disorder wherein the disease, condition, or disorder is implicated in the activation of voltage-gated sodium channels comprising administering an effective amount of a compound of Formula I:

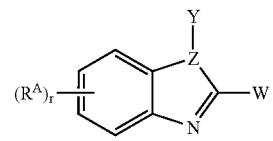

or a pharmaceutically acceptable salt thereof, wherein R$^A$, Z, Y, r, and W are as defined above and in classes and subclasses as described herein.

A preferred aspect of the present embodiment is where the disease, condition, or disorder is acute, chronic, neuropathic, or inflammatory pain, epilepsy or an epilepsy condition, a neurodegenerative disorder, a psychiatric disorder such as anxiety and depression, myotonia, arrhythmia, a movement disorder, a neuroendocrine disorder, ataxia, multiple sclerosis, irritable bowel syndrome, or incontinence.

A particularly preferred aspect of the present embodiment is where the disease, condition, or disorder is acute, chronic, neuropathic, or inflammatory pain.

Another preferred aspect of the present embodiment is where the method comprises an additional therapeutic agent.

Yet another embodiment of the present invention provides a method of inhibiting NaV1.1, NaV1.2, NaV1.3, NaV1.4, NaV1.5, NaV1.6, NaV1.7, NaV1.8, NaV1.9, or CaV2.2 activity in:
(a) a patient; or
(b) a biological sample;

which method comprises administering to said patient, or contacting said biological sample with a compound of Formula I:

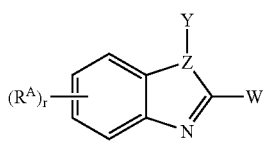

I or a pharmaceutically acceptable salt thereof, wherein $R^A$, Z, Y, r, and W are as defined above and in classes and subclasses as described herein.

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The present invention provides compounds of Formula I with substituents that are monovalent, such as $R^A$, $R^B$, $R^C$ and $R^D$; or divalent, such as A, B, and D. Those skilled in the art will appreciate that for asymmetric divalent substituent groups, such as —$C_{1-6}$alkyl-NH—, and —$C_{1-4}$alkyl-O—, there are two possible orientations relative to the parent structure. As used within the present specification, the orientation of a divalent substituent is set by its left/right orientation relative Formula I as taught in the present specification. Those skilled in the art will also appreciate that this orientation convention is not relevant to symmetrical divalent substituents, such as —C(O)—, or —$C_{1-6}$alkyl-.

For example for Formula I, where Z is N, W is present as Ia, $R^A$ is hydrogen, V is —C(O)—, Ring E is phenyl, $R^B$ is hydrogen; and A and Q are divalent substituents (A is —$C_3$alkyl-NH—, and Q is —$C_1$alkyl-O—), the following is the described compound.

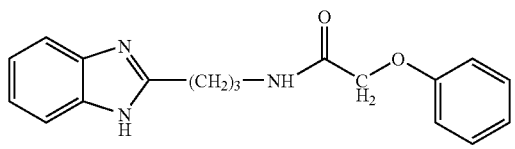

For example for Formula I, where Z is N, W is present as Ia, $R^A$ is hydrogen, V is —C(O)—, Ring E is phenyl, $R^B$ is hydrogen; and A and Q are divalent substituents (A is —$C_2$alkyl-NH— and Q is —O—$C_1$alkyl-), the following is the described compound.

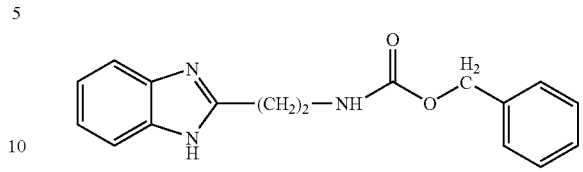

For example for Formula I, where Z is N, W is present as Ia, U is —$CH_2$—, $R^A$ is hydrogen, V is —C(O)—, Ring E is phenyl, $R^B$ is hydrogen; and A and Q are divalent substituents (A is

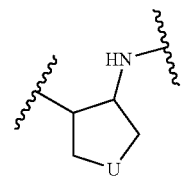

and Q is —$C_1$alkyl-O—), the following is the described compound.

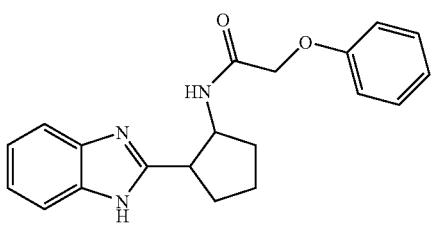

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The terms "aliphatic", "aliphatic group" or "alkyl" as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-20 aliphatic carbon atoms, i.e., $C_{1-20}$alkyl. In some embodiments, aliphatic groups contain 1-10 aliphatic carbon atoms, i.e., $C_{1-10}$alkyl. In other embodiments, aliphatic groups contain 1-8 aliphatic carbon atoms, i.e., $C_{1-8}$alkyl. In still other embodiments, aliphatic groups contain 1-6 aliphatic carbon atoms, i.e., $C_{1-6}$alkyl, and in yet other embodiments aliphatic groups contain 1-4 aliphatic carbon atoms, i.e., $C_{1-4}$alkyl. In some embodiments, "cycloaliphatic" (or "carbocycle" or "cycloalkyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroaliphatic", "heterocycle", "heterocyclyl", "heterocycloaliphatic", or "heterocyclic" as used herein means non-aromatic, monocyclic, bicyclic, or tricyclic ring systems in which one or more ring members is an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom, for example $C_{1-4}$alkoxy refers to the alkoxyl group, methoxy, ethyoxy, propoxy, and butoxy, including for propoxy and butoxy, the straight and branched structures, that is i-propoxy and n-propoxy; and n-butoxy, i-butoxy and sec-butoxy.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroalkyl and heteroarylalkoxy and the like) group may contain one or more substituents. Suitable substituents on the unsaturated carbon atom of an aryl or heteroaryl group are selected from halogen; —$R^o$; —$OR^o$; —$SR^o$; 1,2-methylene-dioxy; 1,2-ethylenedioxy; phenyl (Ph) optionally substituted with $R^o$; —O(Ph) optionally substituted with $R^o$; —$(CH_2)_{1-2}$(Ph), optionally substituted with $R^o$; —CH=CH(Ph), optionally substituted with $R^o$; —$NO_2$; —CN; —$N(R^o)_2$; —$NR^oC(O)R^o$; —$NR^oC(O)N(R^o)_2$; —$NR^oCO_2R^o$; —$NR^oNR^oC(O)R^o$; —$NR^oNR^oC(O)N(R^o)_2$; —$NR^oNR^oCO_2R^o$; —$C(O)C(O)R^o$; —$C(O)CH_2C(O)R^o$; —$CO_2R^o$; —$C(O)R^o$; —$C(O)N(R^o)_2$; —$OC(O)N(R^o)_2$; —$S(O)_2R^o$; —$SO_2N(R^o)_2$; —$S(O)R^o$; —$NR^oSO_2N(R^o)_2$; —$NR^oSO_2R^o$; —C(=S)N$(R^o)_2$; —C(=NH)—N$(R^o)_2$; or —$(CH_2)_{0-2}NHC(O)R^o$ wherein each independent occurrence of $R^o$ is selected from hydrogen, optionally substituted $C_{1-6}$ aliphatic, an unsubstituted 5-6 membered heteroaryl or heterocyclic ring, phenyl, —O(Ph), or —$CH_2$(Ph), or, notwithstanding the definition above, two independent occurrences of $R^o$, on the same substituent or different substituents, taken together with the atom(s) to which each $R^o$ group is bound, form a 3-8-membered cycloalkyl, heterocyclyl, aryl, or heteroaryl ring having 0-3 heteroatoms independently selected from nitrogen, oxygen, or sulfur. Optional substituents on the aliphatic group of $R^o$ are selected from $NH_2$, NH($C_{1-4}$aliphatic), N($C_{1-4}$aliphatic)$_2$, halogen, $C_{1-4}$aliphatic, OH, O($C_{1-4}$aliphatic), $NO_2$, CN, $CO_2H$, $CO_2$($C_{1-4}$aliphatic), O(halo$C_{1-4}$ aliphatic), or halo$C_{1-4}$aliphatic, wherein each of the foregoing $C_{1-4}$aliphatic groups of $R^o$ is unsubstituted.

An aliphatic or heteroaliphatic group, or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHCO$_2$(alkyl), =NNHSO$_2$(alkyl), or =NR*, where each R* is independently selected from hydrogen or an optionally substituted $C_{1-6}$ aliphatic. Optional substituents on the aliphatic group of R* are selected from $NH_2$, NH($C_{1-4}$ aliphatic), N($C_{1-4}$ aliphatic)$_2$, halogen, $C_{1-4}$ aliphatic, OH, O($C_{1-4}$ aliphatic), $NO_2$, CN, $CO_2H$, $CO_2$($C_{1-4}$ aliphatic), O(halo $C_{1-4}$ aliphatic), or halo($C_{1-4}$ aliphatic), wherein each of the foregoing $C_{1-4}$aliphatic groups of R* is unsubstituted.

Optional substituents on the nitrogen of a non-aromatic heterocyclic ring are selected from —$R^+$, —$N(R^+)_2$, —C(O)$R^+$, —$CO_2R^+$, —$C(O)C(O)R^+$, —$C(O)CH_2C(O)R^+$, —$SO_2R^+$, —$SO_2N(R^+)_2$, —C(=S)N$(R^+)_2$, —C(=NH)—N$(R^+)_2$, or —$NR^+SO_2R^+$; wherein $R^+$ is hydrogen, an optionally substituted $C_{1-6}$ aliphatic, optionally substituted phenyl, optionally substituted —O(Ph), optionally substituted —$CH_2$(Ph), optionally substituted —$(CH_2)_{1-2}$(Ph); optionally substituted —CH=CH(Ph); or an unsubstituted 5-6 membered heteroaryl or heterocyclic ring having one to four heteroatoms independently selected from oxygen, nitrogen, or sulfur, or, notwithstanding the definition above, two independent occurrences of $R^+$, on the same substituent or different substituents, taken together with the atom(s) to which each $R^+$ group is bound, form a 3-8-membered cycloalkyl, heterocyclyl, aryl, or heteroaryl ring having 0-3 heteroatoms independently selected from nitrogen, oxygen, or sulfur. Optional substituents on the aliphatic group or the phenyl ring of $R^+$ are selected from $NH_2$, $NH(C_{1-4}$ aliphatic), $N(C_{1-4}$ aliphatic)$_2$, halogen, $C_{1-4}$ aliphatic, OH, $O(C_{1-4}$ aliphatic), $NO_2$, CN, $CO_2H$, $CO_2(C_{1-4}$ aliphatic), O(halo $C_{1-4}$ aliphatic), or halo ($C_{1-4}$ aliphatic), wherein each of the foregoing $C_{1-4}$ aliphatic groups of $R^+$ is unsubstituted.

The term "$C_{1-20}$ alkylidene chain" refers to a straight or branched carbon chain of twenty carbon atoms or less that may be fully saturated or have one or more units of unsaturation and has two points of attachment to the rest of the molecule.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. For example, for compounds of formula I:

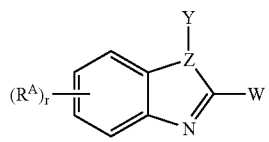

wherein Z is N or O, one of ordinary skill would recognize that a suitable tautomer is as depicted above. When the Z group of formula I is CH, one of ordinary skill would recognize that a suitable tautomer is as depicted below:

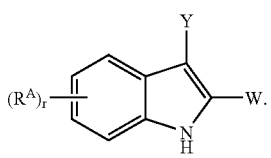

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

3. Description of Exemplary Compounds

In certain embodiments, the present invention provides a compound of formula I wherein V is —$S(O)_2$—.

In other embodiments, the present invention provides a compound of formula I wherein V is —C(O)—.

In one embodiment, T is a $C_{1-6}$ straight or branched aliphatic chain wherein a methylene unit of T is optionally replaced by a $C_{3-6}$ cycloaliphatic group.

Also preferred is a compound of formula I wherein Ring E is phenyl.

Also preferred is a compound of formula I wherein Ring E is naphthyl.

Also preferred is a compound of formula I wherein Ring E is pyridinyl.

Also preferred is a compound of formula I wherein Ring E is thienyl.

Also preferred is a compound of formula I wherein Ring E is furanyl.

Also preferred is a compound of formula I wherein Ring E is quinolinyl.

Also preferred is a compound of formula I wherein Ring E is benzofuranyl.

Also preferred is a compound of formula I wherein Ring E is 3,4-dihydro-2H-chromene.

Also preferred is a compound of formula I wherein Ring E is 2,3-dihydrobenzo[b][1,4]dioxine.

According to one aspect, the present invention provides a compound of formula I, wherein Ring E is a preferred group as described above and said group is in combination with the remaining variables of formula I as set forth in the classes and subclasses described herein.

In certain embodiments, each $R^A$ of formula I, when present, is independently $R^6$, $OR^6$, CN, or halo. In other embodiments, each $R^B$ of formula I, when present, is independently $OR^6$, $N(R^6)_2$, $NR^6C(O)R^6$, halo, $R^6$, $C(O)R^6$, or $NO_2$.

In other embodiments, the A moiety of formula I, when present, is -T-$NR^6$—, wherein T is a $C_{1-6}$ straight or branched aliphatic chain. Such A moieties include —$CH_2CH_2N$($CH_3$)—, —$CH_2CH_2NH$—, —$CH_2NH$—, and —$CH_2CH$($CH_3$)NH—.

In certain embodiments, the present invention provides a compound of formula I wherein A is -T-NH— wherein T is a $C_{1-6}$ straight or branched aliphatic chain wherein a methylene unit of T is replaced by a $C_{3-6}$ cycloaliphatic group. Such cycloaliphatic groups include cyclopropyl, cyclobutyl, cyclopentyl, cyclohexyl, cycloheptyl, or cyclooctyl groups. In other embodiments, the Q moiety of formula I is a $C_{1-4}$ alkylidene chain wherein one methylene unit of Q is replaced by —O—, —NH—, or —S—. Such Q moieties of formula I include —$CH_2CH_2O$—, —$CH_2O$—, —$OCH_2$—, —$OCH_2CH_2$—, —$CH(CH_3)O$—, —$NHCH_2$—, —$C(CH_3)_2O$—, and —$CH_2S$—.

As described above, for compounds of the invention of Formula I, Z is O, N or C. Accordingly, in certain embodiments, where Z is N, the corresponding compounds have the structure of Formula II:

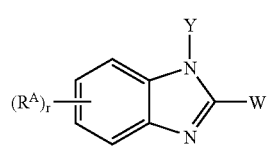

In certain embodiments of Formula II, Y is hydrogen, Ring E is phenyl, and W is formula Ia, wherein V is —C(O)— as shown in Formula IIa:

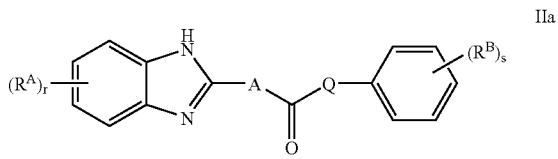

or a pharmaceutically acceptable salt thereof, wherein $R^A$, r, A, Q, $R^B$, and s are as defined above and herein.

Preferred is a compound of Formula IIa, wherein Q is a bond or a $C_{1-4}$ alkylidene chain wherein one methylene unit of Q is replaced by —O—, —NH—, or —S—. Such Q moieties of formula IIa include —CH$_2$CH$_2$O—, —CH$_2$O—, —OCH$_2$—, —OCH$_2$CH$_2$—, —CH(CH$_3$)O—, —NHCH$_2$—, —C(CH$_3$)$_2$O—, and —CH$_2$S—.

Particularly preferred is a compound of Formula IIa, wherein Q is —CH$_2$O—.

Also particularly preferred is a compound of Formula IIa, wherein Q is —OCH$_2$—.

Also particularly preferred is a compound of Formula IIa, wherein Q is —NHCH$_2$—.

Also preferred is a compound of Formula IIa, wherein A is —C$_{1-6}$alkyl —NH—.

Particularly preferred is a compound of Formula IIa, wherein A is —CH$_2$CH$_2$NH—.

Also particularly preferred is a compound Formula IIa, wherein A is —CH$_2$NH—.

In certain embodiments, the present invention provides a compound of formula IIa, wherein A is —CH$_2$CH$_2$NH—, Q is —CH$_2$O—, and each $R^B$ is independently $C_{1-6}$ aliphatic, —CHO, or halogen. In other embodiments, the present invention provides a compound of formula IIb, wherein A is —CH$_2$CH$_2$NH—, Q is —CH$_2$O—, and each $R^B$ is independently methyl, —CHO, fluoro, or chloro.

In other embodiments, the present invention provides a compound of formula IIa, wherein A is —CH$_2$CH$_2$NH—, Q is —CH=CH—, —CH$_2$O— or —NHCH$_2$ and each $R^B$ is independently CN, $C_{1-6}$ aliphatic, —N($R^6$)$_2$, or halogen. Such $R^B$ groups include methyl, ethyl, butyl, isopropyl, chloro, fluoro, bromo, N(Me)$_2$, CF$_3$ and —CH$_2$-phenyl. According to another embodiment, the present invention provides a compound of formula IIa wherein the benzo ring is substituted at one of, or both of, the C-4- and C-5 positions with tert-butyl, fluoro, or methyl.

According to another embodiment, the present invention provides a compound of formula IIa, wherein A is —CH$_2$CH$_2$NH— or —CH(CH$_3$)NH—, Q is —CH$_2$O— and each $R^B$ is independently $C_{1-6}$ aliphatic, —N($R^6$)$_2$, —C(O)$R^6$, or halogen. Such $R^B$ groups include methyl, chloro, bromo, ethyl, N(Me)$_2$, —C≡CH and C(O)CH$_3$.

Yet another embodiment of the present invention relates to a compound of formula IIa, wherein A is —CH$_2$CH$_2$NH—, Q is —CH$_2$O—, —NHCH$_2$—, or —CH(CH$_3$)O—, and each $R^B$ is independently $C_{1-6}$ aliphatic, —OR$^6$, or halogen. Such $R^B$ groups include methyl, ethyl, —OMe, chloro, bromo, and fluoro.

According to still another embodiment, the present invention provides a compound of formula IIa, wherein A is —CH$_2$CH$_2$NH— or —CH$_2$CH(CH$_3$)NH—, Q is —CH$_2$O—, —NHCH$_2$—, —NH—, —CH(CH$_3$)O—, or —C(CH$_3$)$_2$O—, and each $R^B$ is independently $C_{1-6}$ aliphatic, —OR$^6$, or halogen. Such $R^B$ groups include methyl, ethyl, —OMe, chloro, bromo, and fluoro. According to another embodiment, the present invention provides a compound of formula IIa wherein r is 2, each $R^A$ is fluoro, and is present at the C-4- and C-5 positions.

In certain embodiments, the present invention provides a compound of formula IIa, wherein A is —CH$_2$CH$_2$NH—, Q is —CH$_2$O—, and each $R^B$ is independently $C_{1-6}$ aliphatic or halogen. In other embodiments, the present invention provides a compound of formula IIa, wherein A is —CH$_2$CH$_2$NH—, Q is —CH$_2$O—, and each $R^B$ is independently methyl, isopropyl, fluoro, bromo, or chloro. In still other embodiments, the present invention provides a compound of formula IIa, wherein A is —CH$_2$CH$_2$NH—, Q is —CH$_2$O—, and each $R^B$ is independently methyl, fluoro, or chloro. In yet other embodiments, the present invention provides a compound of formula IIa, wherein A is —CH$_2$CH$_2$NH—, Q is —CH$_2$O—, and each $R^B$ is independently methyl, bromo, or chloro.

Also preferred is a compound of Formula IIa, wherein A is

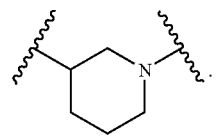

Also preferred is a compound of Formula IIa, wherein A is

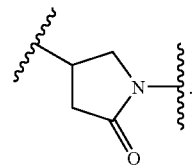

Also preferred is a compound of Formula IIa, wherein A is

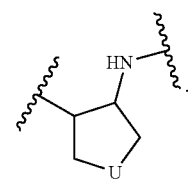

wherein U is —CH$_2$— or —CH$_2$CH$_2$—.

In certain embodiments of Formula II, Y is hydrogen, Ring E is phenyl, W is Formula Ib and D is a bond, as shown below as formula IIb.

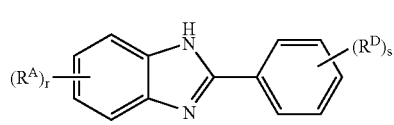

or a pharmaceutically acceptable salt thereof, wherein $R^A$, r, $R^D$, and s are as defined above and herein.

Preferred is a compound of Formula IIb, wherein $R^A$ is $R^6$ or halo. In certain embodiments, $R^A$ is methyl, chloro or bromo.

Particularly preferred is a compound of Formula IIb, wherein $R^A$ is methyl.

Also preferred is a compound of Formula IIb wherein $R^D$ is halo, $OR^6$, $N(R^6)_2$, $NR^6C(O)R^6$, or two $R^D$ are taken together to form a methylenedioxy or ethylenedioxy group. In certain embodiments, $R^D$ is —OH, —N(Et)$_2$, —OMe, —NHC(O)CH$_3$, fluoro, or chloro.

According to another embodiment, the present invention provides a compound of formula III:

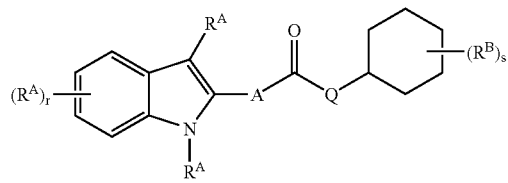

III or a pharmaceutically acceptable salt thereof, wherein A, Q, $R^A$, r, $R^B$, and s are as defined above and herein.

In certain embodiments, each $R^A$ of formula III, when present, is independently $R^6$, $OR^6$, CN, or halo. In other embodiments, each $R^B$ of formula III, when present, is independently $OR^6$, $N(R^6)_2$, $NR^6C(O)R^6$, halo, $R^6$, $C(O)R^6$, or $NO_2$. In other embodiments, the Q moiety of formula III is a $C_{1-4}$ alkylidene chain wherein one methylene unit of Q is replaced by —O—, —NH—, or —S—. Such Q moieties of formula III include —CH$_2$CH$_2$O—, —CH$_2$O—, —OCH$_2$—, —OCH$_2$CH$_2$—, —CH(CH$_3$)O—, —NHCH$_2$—, —C(CH$_3$)$_2$O—, and —CH$_2$S—.

In other embodiments, the A moiety of formula III, when present, is -T-NR$^6$—, wherein T is a $C_{1-6}$ straight or branched aliphatic chain. Such A moieties include —CH$_2$CH$_2$N(CH$_3$)—, —CH$_2$CH$_2$NH—, —CH$_2$NH—, and —CH$_2$CH(CH$_3$)NH—.

In certain embodiments, the present invention provides a compound of formula III wherein A is -T-NH— wherein T is a $C_{1-6}$ straight or branched aliphatic chain wherein a methylene unit of T is replaced by a $C_{3-6}$ cycloaliphatic group. Such cycloaliphatic groups include cyclobutyl, cyclopentyl, and cyclohexyl groups.

According to another embodiment, the present invention provides a compound of formula IV:

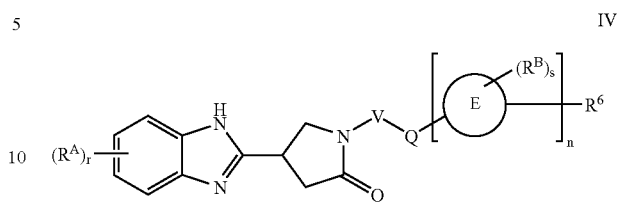

IV or a pharmaceutically acceptable salt thereof, wherein V, Q, $R^A$, r, $R^B$, n, and s are as defined above and herein.

In certain embodiments, each $R^A$ of formula IV, when present, is independently $R^6$, $OR^6$, CN, or halo. In other embodiments, each $R^B$ of formula IV, when present, is independently $OR^6$, $N(R^6)_2$, $NR^6C(O)R^6$, halo, $R^6$, $C(O)R^6$, or $NO_2$.

In other embodiments, the Ring E group of formula IV is phenyl or a 5-6 membered heteroaryl ring having 1-4 heteroatoms independently selected from nitrogen, oxygen, or sulfur, or a 3-7 membered monocyclic heterocyclyl ring having 1-4 heteroatoms independently selected from nitrogen, oxygen, or sulfur. Such Ring E groups of formula IV include pyridyl, thienyl, furyl, and pyrazolyl.

In still other embodiments, the Ring E group of formula IV is an 8-10 membered bicyclic aryl ring or an 8-10 membered bicyclic heteroaryl ring having 1-4 heteroatoms independently selected from nitrogen, oxygen, or sulfur. Such Ring E groups of formula IV include naphthyl, quinolinyl, 3,4-dihydro-2H-chromene, and 2,3-dihydrobenzo[b][1,4]dioxine.

In other embodiments, the Q moiety of formula IV is a $C_{1-4}$ alkylidene chain wherein one methylene unit of Q is replaced by —O—, —NH—, or —S—. Such Q moieties of formula IV include —CH$_2$CH$_2$O—, —CH$_2$O—, —OCH$_2$—, —OCH$_2$CH$_2$—, —CH(CH$_3$)O—, —NHCH$_2$—, —C(CH$_3$)$_2$O—, and —CH$_2$S—.

According to another aspect of the present invention, one of V and Q is a bond. According to yet another aspect of the present invention, both of V and Q are a bond.

Representative compounds of formula I are set forth in Table 2 below.

TABLE 2

Representative Compounds of Formula I

| Cmpd # | Compound |
|---|---|
| 1 | ![compound 1: 5-chloro-2-(4-hydroxyphenyl)benzimidazole] |
| 2 | ![compound 2: N-(4-(4-methyl-1H-benzimidazol-2-yl)phenyl)acetamide] |

TABLE 2-continued

Representative Compounds of Formula I

| Cmpd # | Compound |
|---|---|
| 3 | N-(2-(1H-benzimidazol-2-yl)ethyl)furan-2-carboxamide |
| 4 | 2-ethoxy-N-(2-(1H-benzimidazol-2-yl)ethyl)benzamide |
| 5 | N-(2-(1H-benzimidazol-2-yl)ethyl)-3,4-dimethoxybenzamide |
| 6 | N-(2-(1H-benzimidazol-2-yl)ethyl)-3,4-dichlorobenzamide |
| 7 | N-(2-(1H-benzimidazol-2-yl)ethyl)-3-methylbenzamide |
| 9 | N-(2-(1H-benzimidazol-2-yl)ethyl)-2-phenylacetamide |
| 12 | N-(2-(1H-benzimidazol-2-yl)ethyl)propanamide |

TABLE 2-continued

Representative Compounds of Formula I

| Cmpd # | Compound |
|---|---|
| 13 | 3,4,5-trimethoxy-N-(2-(1H-benzimidazol-2-yl)ethyl)benzamide |
| 14 | 4-chloro-N-(2-(1H-benzimidazol-2-yl)ethyl)benzenesulfonamide |
| 15 | N-(2-(1H-benzimidazol-2-yl)ethyl)-2,3-dihydro-1,4-benzodioxine-2-carboxamide |
| 16 | N-(2-(1H-benzimidazol-2-yl)ethyl)-2-(2-methoxyphenoxy)acetamide |
| 17 | N-(2-(1H-benzimidazol-2-yl)ethyl)-2-(2-methylphenoxy)acetamide |
| 19 | N-(3-(1H-benzimidazol-2-yl)propyl)acetamide |

TABLE 2-continued

Representative Compounds of Formula I

| Cmpd # | Compound |
|---|---|
| 20 | *N-(2-(1H-benzimidazol-2-yl)ethyl)thiophene-2-carboxamide* |
| 21 | *N-(2-(1H-benzimidazol-2-yl)ethyl)-4-methylbenzamide* |
| 22 | *N-(2-(1H-benzimidazol-2-yl)ethyl)-2-(3,5-dimethylphenoxy)acetamide* |
| 23 | *N-(2-(1H-benzimidazol-2-yl)ethyl)-2-(3,4-dimethylphenoxy)acetamide* |
| 24 | *N-(2-(1H-benzimidazol-2-yl)ethyl)-[1,1'-biphenyl]-4-carboxamide* |
| 25 | *N-(2-(1H-benzimidazol-2-yl)ethyl)-3-chlorobenzamide* |

TABLE 2-continued

Representative Compounds of Formula I

| Cmpd # | Compound |
|---|---|
| 26 | *N-(2-(1H-benzimidazol-2-yl)ethyl)benzamide structure* |
| 28 | *4-chloro-N-(2-(1H-benzimidazol-2-yl)ethyl)benzamide structure* |
| 29 | *N-(2-(1H-benzimidazol-2-yl)ethyl)-3-phenoxypropanamide structure* |
| 30 | *N-(2-(1H-benzimidazol-2-yl)ethyl)-2-(3-chlorophenoxy)acetamide structure* |
| 35 | *5-chloro-2-(2-chlorophenyl)-1H-benzimidazole structure* |
| 36 | *N-(4-(5-chloro-1H-benzimidazol-2-yl)phenyl)acetamide structure* |

TABLE 2-continued

Representative Compounds of Formula I

| Cmpd # | Compound |
|---|---|
| 37 | 3-methoxy-N-(2-(1H-benzimidazol-2-yl)ethyl)benzamide |
| 40 | N-(2-(1H-benzimidazol-2-yl)ethyl)pentanamide |
| 45 | 2-(2-bromophenoxy)-N-(2-(1H-benzimidazol-2-yl)ethyl)acetamide |
| 46 | 4-(1H-benzimidazol-2-yl)-1-phenylpyrrolidin-2-one |
| 47 | 3-(1,3-dioxoisoindolin-2-yl)-N-(2-(1H-indol-2-yl)ethyl)propanamide |
| 48 | N-(2-(1H-benzimidazol-2-yl)ethyl)-2-phenoxyacetamide |

TABLE 2-continued
Representative Compounds of Formula I
| Cmpd # | Compound |
|---|---|
| 49 | 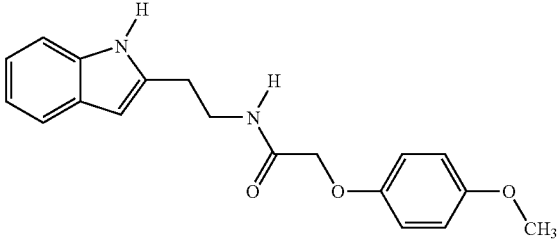 |
| 51 | 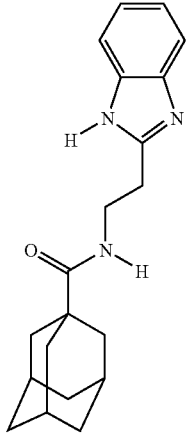 |
| 52 | 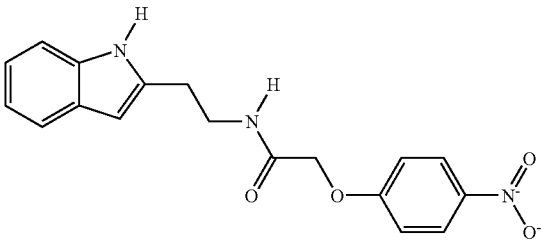 |
| 53 | 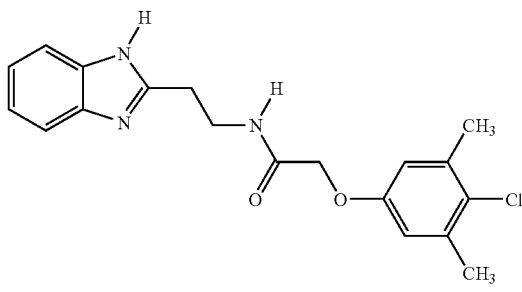 |

TABLE 2-continued
Representative Compounds of Formula I
| Cmpd # | Compound |
|---|---|
| 54 | 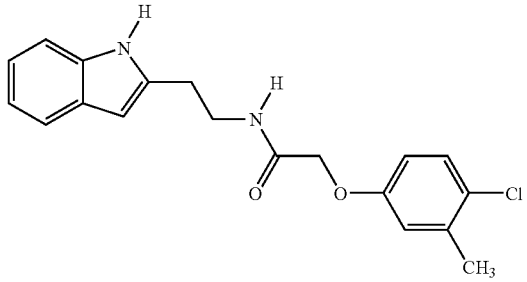 |
| 55 | 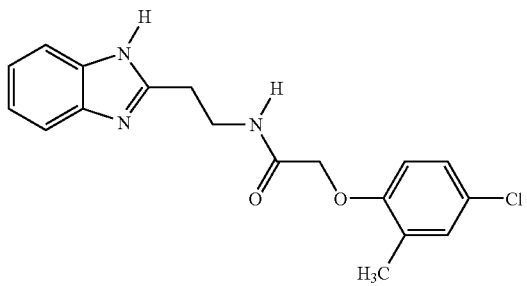 |
| 56 | 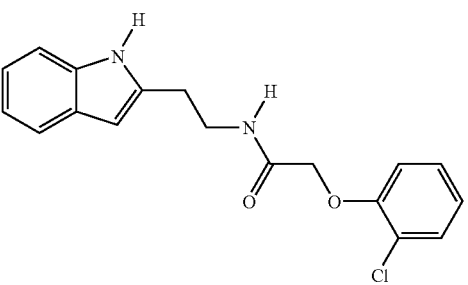 |
| 57 | 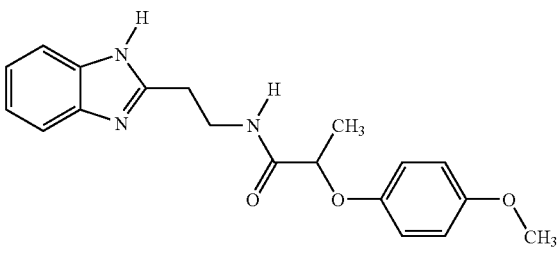 |
| 58 | 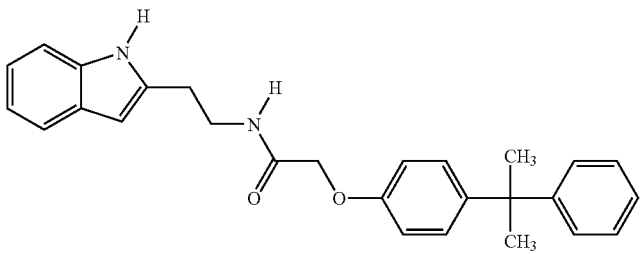 |

TABLE 2-continued

Representative Compounds of Formula I

| Cmpd # | Compound |
|---|---|
| 59 | 2-(1H-benzimidazol-2-yl)ethyl-N-[2-(5-methyl-2-isopropylphenoxy)acetamide] |
| 60 | 4-methyl-2-(2,6-difluorophenyl)-1H-benzimidazole |
| 61 | 5-chloro-2-(2,6-difluorophenyl)-1H-benzimidazole |
| 62 | 5,6-dichloro-2-(2,6-difluorophenyl)-1H-benzimidazole |
| 63 | 2-(1H-benzimidazol-2-yl)ethyl-N-[2-(2-nitrophenoxy)acetamide] |
| 64 | 2-(1H-indol-2-yl)ethyl-N-[2-(2-bromo-4-methylphenoxy)acetamide] |

TABLE 2-continued

Representative Compounds of Formula I

| Cmpd # | Compound |
|---|---|
| 65 | 2-(2-isopropylphenoxy)-N-(2-(1H-benzimidazol-2-yl)ethyl)acetamide |
| 66 | 2-(biphenyl-4-yloxy)-N-(2-(1H-indol-2-yl)ethyl)acetamide |
| 67 | 2-(2,6-dimethylphenoxy)-N-(2-(1H-benzimidazol-2-yl)ethyl)acetamide |
| 68 | 2-(4-isopropyl-3-methylphenoxy)-N-(2-(1H-indol-2-yl)ethyl)acetamide |
| 69 | 2-(2,3,6-trimethylphenoxy)-N-(2-(1H-benzimidazol-2-yl)ethyl)acetamide |

TABLE 2-continued

Representative Compounds of Formula I

| Cmpd # | Compound |
|---|---|
| 70 | 1H-indol-2-ylmethyl-NH-C(=O)-CH₂-O-(4-methoxyphenyl) |
| 71 | 1H-benzimidazol-2-ylmethyl-NH-C(=O)-CH(CH₃)-O-(2-chlorophenyl) |
| 72 | 1H-indol-2-ylmethyl-NH-C(=O)-CH₂-O-(4-bromophenyl) |
| 73 | 1H-benzimidazol-2-ylmethyl-NH-C(=O)-CH₂-O-(4-iodophenyl) |

TABLE 2-continued

Representative Compounds of Formula I

| Cmpd # | Compound |
|---|---|
| 74 | N-((1H-indol-2-yl)methyl)benzofuran-2-carboxamide |
| 75 | N-((1H-benzo[d]imidazol-2-yl)methyl)-2-(o-tolyloxy)acetamide |
| 76 | N-((1H-indol-2-yl)methyl)-2-(p-tolyloxy)acetamide |
| 77 | N-((1H-benzo[d]imidazol-2-yl)methyl)-2-(2-hydroxyphenoxy)acetamide |
| 78 | N-((1H-indol-2-yl)methyl)-2-(4-hydroxyphenoxy)acetamide |

TABLE 2-continued

Representative Compounds of Formula I

| Cmpd # | Compound |
|---|---|
| 79 | benzimidazol-2-ylmethyl-NH-C(O)-CH$_2$-O-(2-formylphenyl) |
| 80 | benzimidazol-2-ylmethyl-NH-C(O)-CH$_2$-O-(2-methoxyphenyl) |
| 81 | benzimidazol-2-ylmethyl-NH-C(O)-CH(CH$_3$)-O-(4-hydroxyphenyl) |
| 82 | benzimidazol-2-ylmethyl-NH-C(O)-CH$_2$-O-(4-chlorophenyl) |

TABLE 2-continued

Representative Compounds of Formula I

| Cmpd # | Compound |
|---|---|
| 83 | (structure) |
| 84 | (structure) |
| 85 | (structure) |
| 86 | (structure) |
| 87 | (structure) |

TABLE 2-continued
Representative Compounds of Formula I
| Cmpd # | Compound |
|---|---|
| 88 | 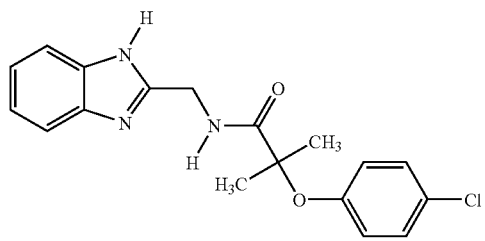 |
| 89 | 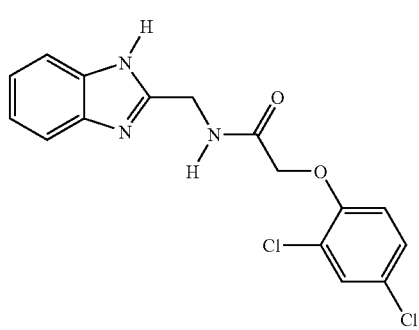 |
| 90 | 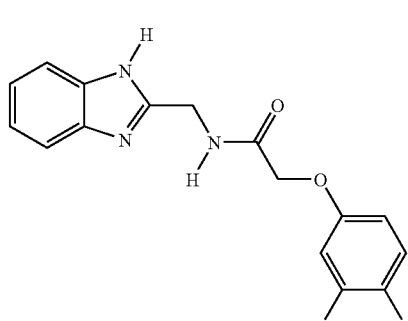 |
| 91 | 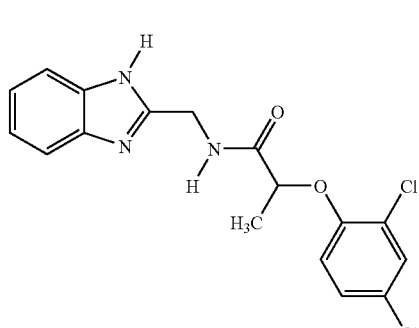 |

TABLE 2-continued

Representative Compounds of Formula I

| Cmpd # | Compound |
|---|---|
| 92 | 2-((1H-benzo[d]imidazol-2-yl)methylamino)-N-(perfluorophenoxy)acetamide structure |
| 93 | N-((1H-benzo[d]imidazol-2-yl)methyl)-2-(2-chlorophenoxy)-2-methylpropanamide structure |
| 94 | 2-(2,3-dichloro-4-(2-methylenebutanoyl)phenoxy)-N-((1H-benzo[d]imidazol-2-yl)methyl)acetamide structure |
| 95 | N-((1H-benzo[d]imidazol-2-yl)methyl)-2-(4-(2-(4-chlorobenzamido)ethyl)phenoxy)-2-methylpropanamide structure |

TABLE 2-continued

Representative Compounds of Formula I

| Cmpd # | Compound |
|---|---|
| 96 | *N-((1H-benzimidazol-2-yl)methyl)-2,5-dimethoxybenzamide* |
| 97 | *N-((1H-benzimidazol-2-yl)methyl)-2-(3,5-dimethylphenoxy)acetamide* |
| 98 | *N-((1H-benzimidazol-2-yl)methyl)-2-(2,6-dimethylphenoxy)acetamide* |
| 99 | *N-((1H-benzimidazol-2-yl)methyl)-2-(2-isopropyl-5-methylphenoxy)acetamide* |
| 100 | *N-((1H-benzimidazol-2-yl)methyl)-naphtho[2,3-d][1,3]dioxole-2-carboxamide* |

TABLE 2-continued

Representative Compounds of Formula I

| Cmpd # | Compound |
|---|---|
| 101 | |
| 102 | |
| 103 | |
| 104 | |
| 105 | |

TABLE 2-continued

Representative Compounds of Formula I

| Cmpd # | Compound |
|---|---|
| 106 | 7-methyl-2-(2-chlorophenyl)-1H-benzimidazole |
| 107 | 7-methyl-2-(2-bromophenyl)-1H-benzimidazole |
| 108 | 7-methyl-2-(2-methylphenyl)-1H-benzimidazole |
| 109 | 7-methyl-2-(2-hydroxyphenyl)-1H-benzimidazole |
| 110 | 7-methyl-2-(3-methoxyphenyl)-1H-benzimidazole |
| 111 | 7-methyl-2-(4-chlorophenyl)-1H-benzimidazole |
| 112 | 7-methyl-2-(4-hydroxyphenyl)-1H-benzimidazole |

TABLE 2-continued

Representative Compounds of Formula I

| Cmpd # | Compound |
|---|---|
| 113 | [structure: 7-methyl-2-(2,6-dimethoxyphenyl)-1H-benzimidazole] |
| 114 | [structure: 7-methyl-2-(2,6-dichlorophenyl)-1H-benzimidazole] |
| 115 | [structure: N-((1H-benzimidazol-2-yl)methyl)-2-(2,4-di-tert-pentylphenoxy)butanamide] |
| 116 | [structure: N-((1H-benzimidazol-2-yl)methyl)-2-phenoxybutanamide] |
| 117 | [structure: N-((1H-benzimidazol-2-yl)methyl)-2-(3,4-dimethylphenoxy)acetamide] |

TABLE 2-continued
Representative Compounds of Formula I
| Cmpd # | Compound |
|---|---|
| 118 | 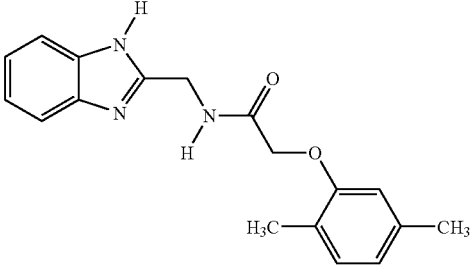 |
| 119 | 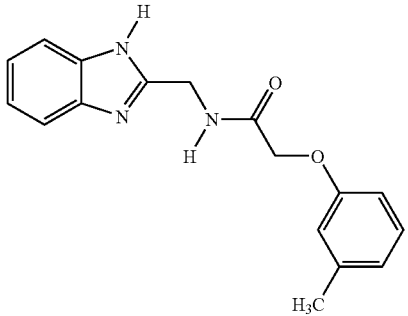 |
| 120 | 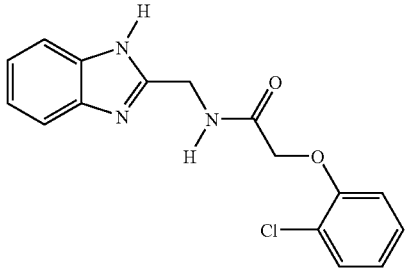 |
| 121 | 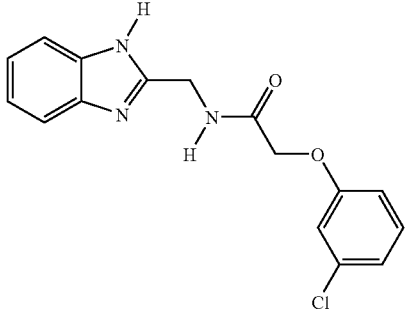 |

TABLE 2-continued
Representative Compounds of Formula I
| Cmpd # | Compound |
|---|---|
| 122 | 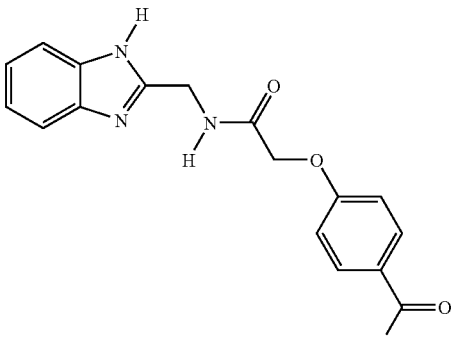 |
| 123 | 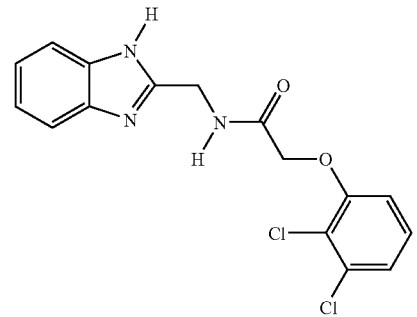 |
| 124 | 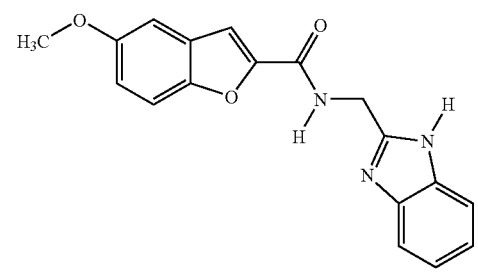 |
| 126 | 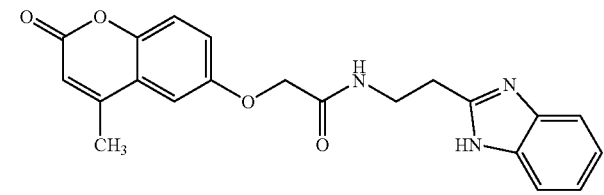 |
| 127 | 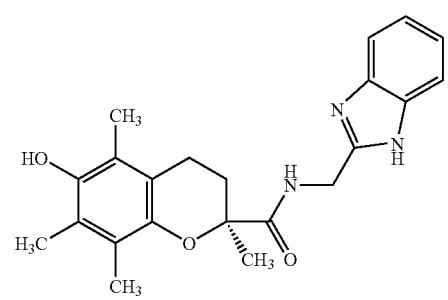 |

TABLE 2-continued

Representative Compounds of Formula I

| Cmpd # | Compound |
|---|---|
| 128 | *(structure: 6-hydroxy-2,5,7,8-tetramethylchroman-2-carboxamide linked via NH-CH₂ to benzimidazole)* |
| 129 | *(structure: benzimidazol-2-ylmethyl-NH-C(O)-CH₂-O-(3-nitrophenyl))* |
| 130 | *(structure: benzimidazol-2-ylmethyl-NH-C(O)-CH₂-O-(4-benzyloxyphenyl))* |
| 131 | *(structure: benzimidazol-2-ylmethyl-NH-C(O)-CH₂-O-(2,3-dimethylphenyl))* |
| 132 | *(structure: benzimidazol-2-ylmethyl-NH-C(O)-CH₂-O-(2,4-dimethylphenyl))* |

TABLE 2-continued

Representative Compounds of Formula I

| Cmpd # | Compound |
|---|---|
| 133 | 5-chlorobenzofuran-2-carboxylic acid ((1H-benzimidazol-2-yl)methyl)amide |
| 134 | 5-nitrobenzofuran-2-carboxylic acid ((1H-benzimidazol-2-yl)methyl)amide |
| 136 | 4-(7-methyl-1H-benzimidazol-2-yl)-3-hydroxy-N,N-diethylaniline |
| 137 | 2-(3,4-dichlorophenyl)-7-methyl-1H-benzimidazole |
| 138 | 2-(2,4-dimethoxyphenyl)-7-methyl-1H-benzimidazole |
| 139 | 2-(2,5-dimethylphenyl)-7-methyl-1H-benzimidazole |

TABLE 2-continued

Representative Compounds of Formula I

| Cmpd # | Compound |
|---|---|
| 144 | 5-chloro-2-(2-fluorophenyl)-1H-benzimidazole |
| 145 | 5-chloro-2-(2,6-dichlorophenyl)-1H-benzimidazole |
| 146 | 5-chloro-2-(3,4-dichlorophenyl)-1H-benzimidazole |
| 147 | 5-chloro-2-(1,3-benzodioxol-5-yl)-1H-benzimidazole |
| 148 | 5-chloro-2-(2,4-dimethoxyphenyl)-1H-benzimidazole |
| 149 | 5-chloro-2-(2,5-dimethylphenyl)-1H-benzimidazole |
| 154 | N-[2-(1H-benzimidazol-2-yl)ethyl]-3-(2-chlorophenyl)acrylamide |
| 155 | N-[2-(1H-benzimidazol-2-yl)ethyl]-4-chloro-3-nitrobenzamide |

TABLE 2-continued

Representative Compounds of Formula I

| Cmpd # | Compound |
|---|---|
| 159 | 2-(1H-benzimidazol-2-yl)ethyl tert-butyl carbamate |
| 160 | N-[2-(1H-benzimidazol-2-yl)ethyl]-2-(2-chlorophenoxy)propanamide |
| 161 | N-[2-(1H-benzimidazol-2-yl)ethyl]-2-(4-bromophenoxy)acetamide |
| 162 | N-[2-(1H-benzimidazol-2-yl)ethyl]-2-(4-iodophenoxy)acetamide |
| 163 | N-[2-(1H-benzimidazol-2-yl)ethyl]-1-benzofuran-2-carboxamide |
| 164 | N-[2-(1H-benzimidazol-2-yl)ethyl]-2-(4-methylphenoxy)acetamide |

TABLE 2-continued
Representative Compounds of Formula I
| Cmpd # | Compound |
|---|---|
| 165 | 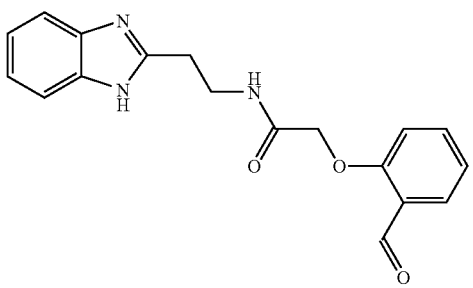 |
| 166 | 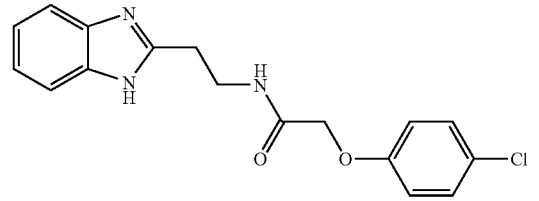 |
| 167 | 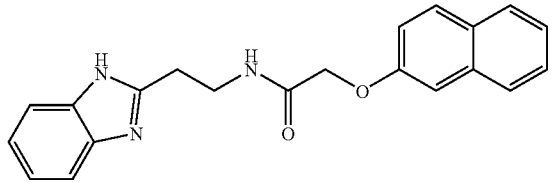 |
| 168 | 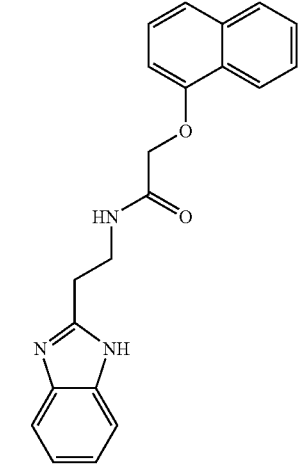 |
| 169 | 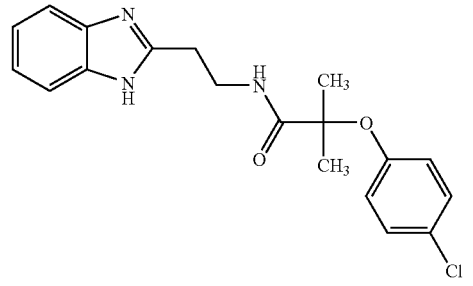 |

TABLE 2-continued
Representative Compounds of Formula I
| Cmpd # | Compound |
|---|---|
| 170 | 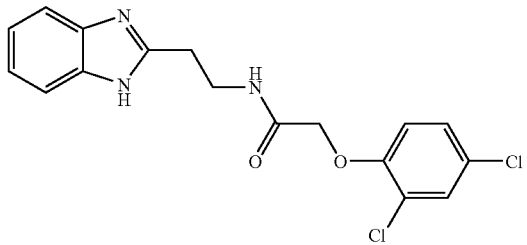 |
| 171 | 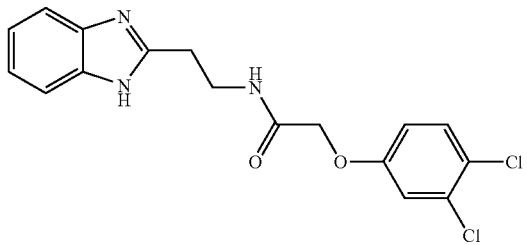 |
| 172 | 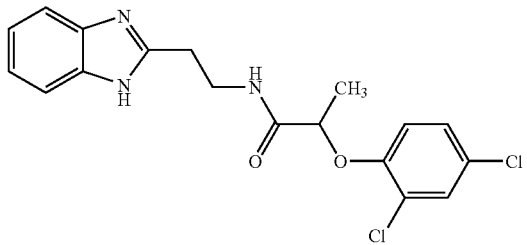 |
| 173 | 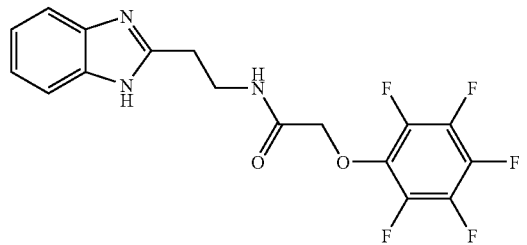 |
| 174 | 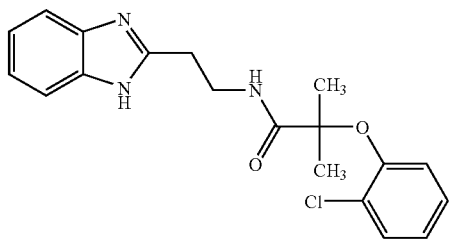 |
| 175 | 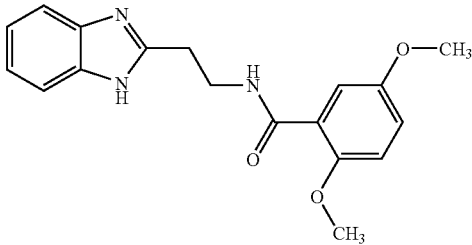 |

TABLE 2-continued

Representative Compounds of Formula I

| Cmpd # | Compound |
|---|---|
| 176 | *structure: naphtho[2,3-d][1,3]dioxole-2-carboxamide linked via NH-CH2CH2- to 1H-benzimidazol-2-yl* |
| 177 | *structure: 2-(biphenyl-4-yloxy)-N-[2-(1H-benzimidazol-2-yl)ethyl]propanamide* |
| 178 | *structure: 2-[(7-bromonaphthalen-2-yl)oxy]-N-[2-(1H-benzimidazol-2-yl)ethyl]propanamide* |
| 179 | *structure: 2-(2,4-dibromophenoxy)-N-[2-(1H-benzimidazol-2-yl)ethyl]propanamide* |
| 180 | *structure: N-[2-(1H-benzimidazol-2-yl)ethyl]-2-[2,4-bis(2-methylbutan-2-yl)phenoxy]butanamide* |
| 181 | *structure: N-[2-(4-methyl-1H-benzimidazol-2-yl)ethyl]-2-(3,4-dimethylphenoxy)acetamide* |

TABLE 2-continued
Representative Compounds of Formula I
| Cmpd # | Compound |
|---|---|
| 182 | 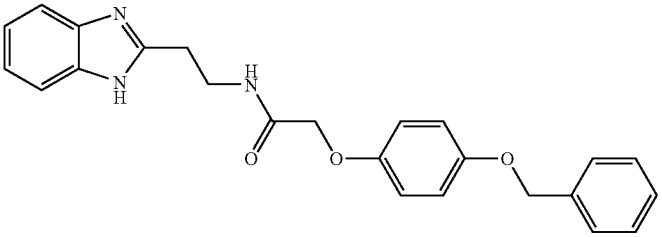 |
| 183 | 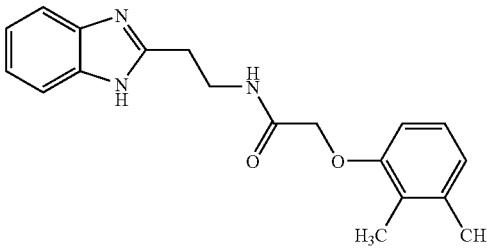 |
| 184 | 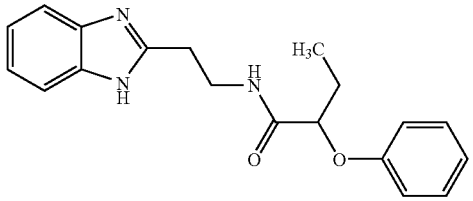 |
| 185 | 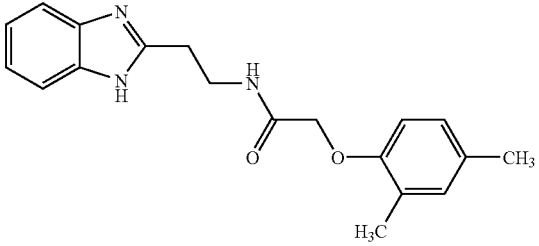 |
| 186 | 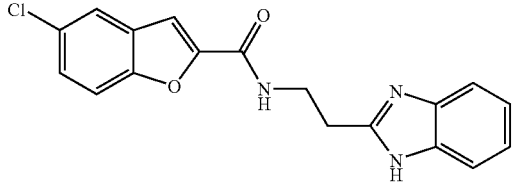 |
| 187 | 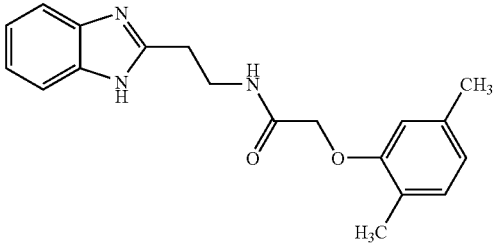 |

TABLE 2-continued

Representative Compounds of Formula I

| Cmpd # | Compound |
|---|---|
| 188 | benzimidazole-CH₂CH₂-NH-C(=O)-CH₂-O-(3-methylphenyl) |
| 189 | benzimidazole-CH₂CH₂-NH-C(=O)-CH₂-O-(4-formylphenyl) |
| 190 | benzimidazole-CH₂CH₂-NH-C(=O)-CH₂-O-(2,3-dichlorophenyl) |
| 191 | 5-methoxybenzofuran-2-C(=O)-NH-CH₂CH₂-benzimidazole |
| 192 | benzimidazole-CH₂CH₂-NH-C(=O)-CH₂-O-(3-formylphenyl) |
| 193 | benzimidazole-CH₂CH₂-NH-C(=O)-CH₂-O-(2-fluorophenyl) |

TABLE 2-continued
Representative Compounds of Formula I
| Cmpd # | Compound |
|---|---|
| 194 | 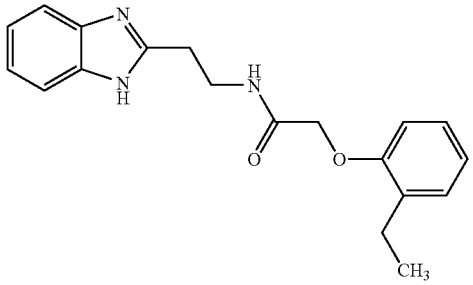 |
| 195 | 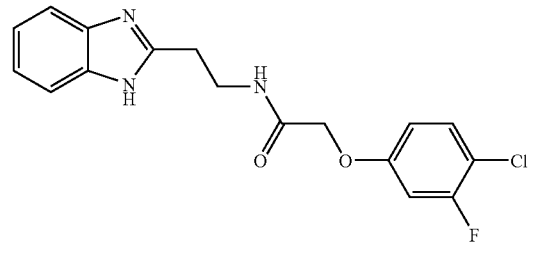 |
| 196 | 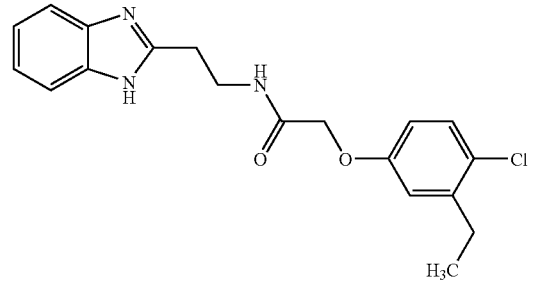 |
| 197 | 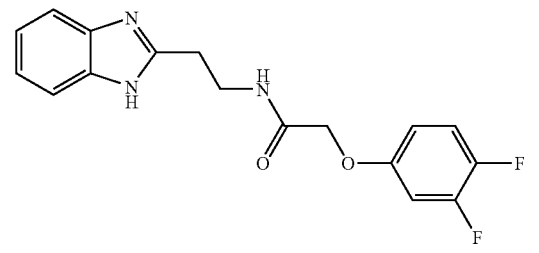 |
| 198 | 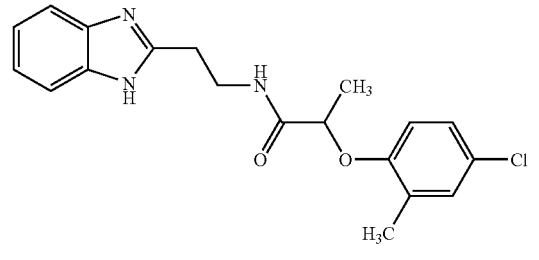 |

TABLE 2-continued
Representative Compounds of Formula I
| Cmpd # | Compound |
|---|---|
| 199 | 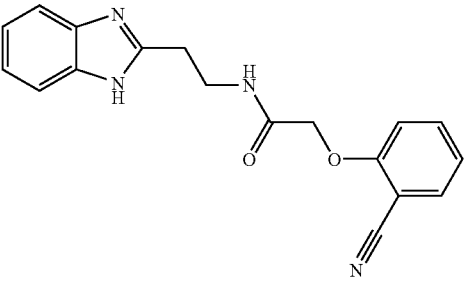 |
| 200 | 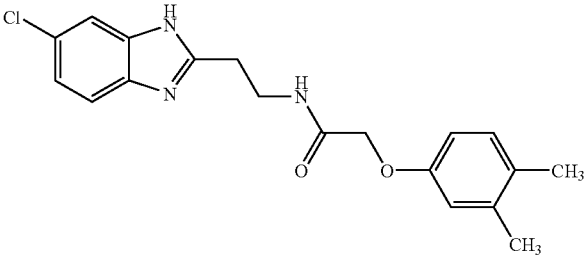 |
| 201 | 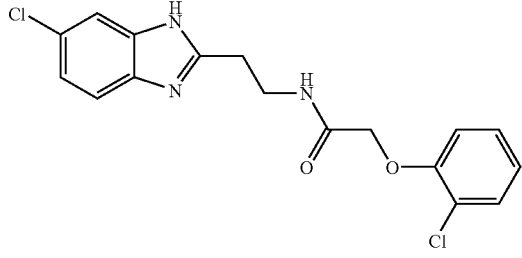 |
| 202 | 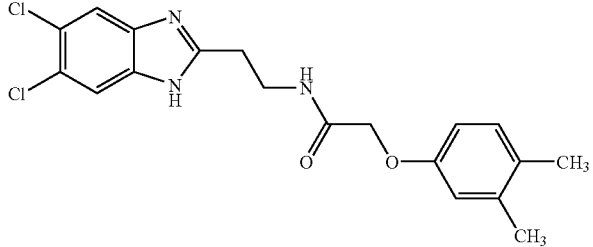 |
| 203 | 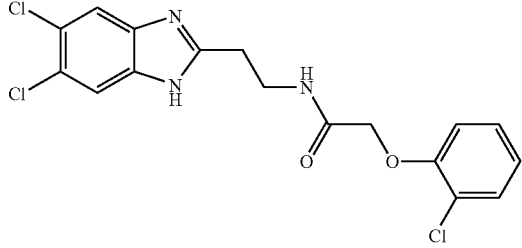 |

TABLE 2-continued

Representative Compounds of Formula I

| Cmpd # | Compound |
|---|---|
| 204 | 2-(5,6-dimethyl-1H-benzimidazol-2-yl)ethyl-N-[2-(3,4-dimethylphenoxy)acetamide] structure |
| 205 | 2-(5,6-dimethyl-1H-benzimidazol-2-yl)ethyl-N-[2-(2-chlorophenoxy)acetamide] structure |
| 206 | 2-(5-methyl-1H-benzimidazol-2-yl)ethyl-N-[2-(3,4-dimethylphenoxy)acetamide] structure |
| 207 | 2-(5-methyl-1H-benzimidazol-2-yl)ethyl-N-[2-(2-chlorophenoxy)acetamide] structure |
| 208 | 2-(7-nitro-1H-benzimidazol-2-yl)ethyl-N-[2-(3,4-dimethylphenoxy)acetamide] structure |

TABLE 2-continued

Representative Compounds of Formula I

| Cmpd # | Compound |
|---|---|
| 209 | (4-nitro-1H-benzimidazol-2-yl)ethyl-NH-C(O)-CH₂-O-(2-chlorophenyl) |
| 210 | (5-nitro-1H-benzimidazol-2-yl)ethyl-NH-C(O)-CH₂-O-(3,4-dimethylphenyl) |
| 211 | (5-nitro-1H-benzimidazol-2-yl)ethyl-NH-C(O)-CH₂-O-(2-chlorophenyl) |
| 212 | (1-methyl-1H-benzimidazol-2-yl)ethyl-NH-C(O)-CH₂-O-(3,4-dimethylphenyl) |
| 213 | (1-methyl-1H-benzimidazol-2-yl)ethyl-NH-C(O)-CH₂-O-(3,4-dichlorophenyl) |

TABLE 2-continued
Representative Compounds of Formula I
| Cmpd # | Compound |
|---|---|
| 214 | 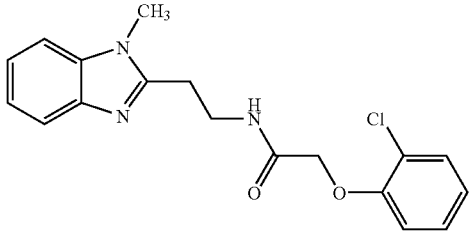 |
| 215 | 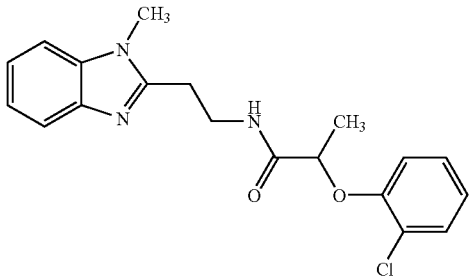 |
| 216 | 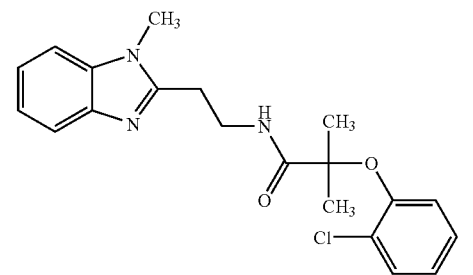 |
| 217 | 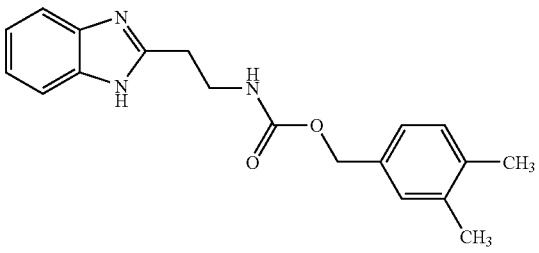 |
| 218 | 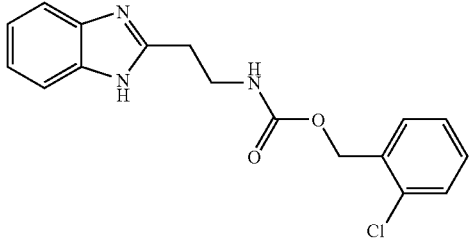 |

TABLE 2-continued

Representative Compounds of Formula I

| Cmpd # | Compound |
|---|---|
| 219 | benzimidazole-CH₂CH₂-NH-C(=O)-O-CH₂-(3,4-difluorophenyl) |
| 220 | benzimidazole-CH₂CH₂-NH-C(=O)-O-CH₂-(3,4-dichlorophenyl) |
| 221 | benzimidazole-CH₂CH₂-NH-C(=O)-O-CH₂-(2,6-dichlorophenyl) |
| 223 | benzimidazole-CH₂CH₂-NH-C(=O)-(2-methylphenyl) |
| 224 | benzimidazole-CH₂CH₂-NH-C(=O)-(4-methyl-3-nitrophenyl) |
| 225 | benzimidazole-CH₂CH₂-NH-C(=O)-(3-bromophenyl) |

TABLE 2-continued
Representative Compounds of Formula I
| Cmpd # | Compound |
|---|---|
| 227 | 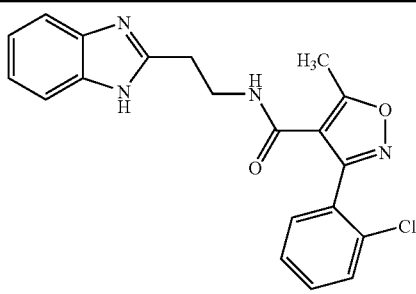 |
| 228 | 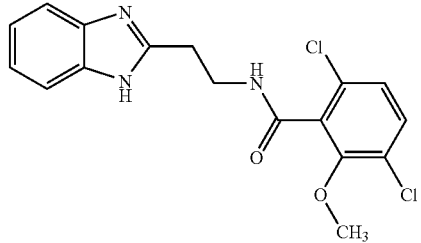 |
| 230 | 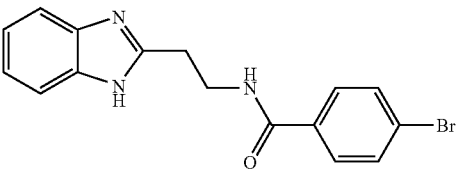 |
| 233 | 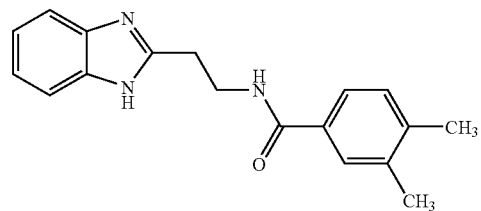 |
| 234 | 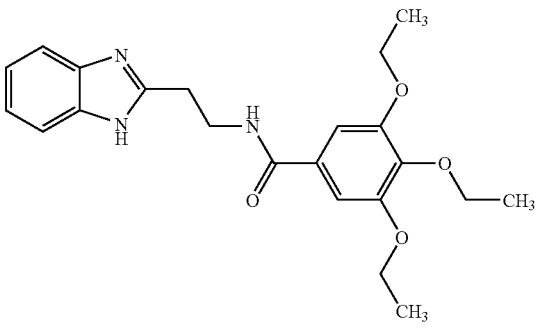 |
| 235 | 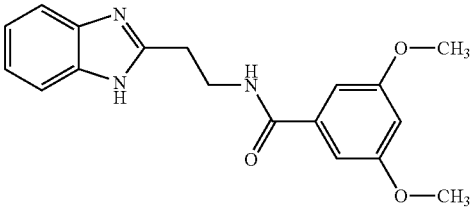 |

TABLE 2-continued

Representative Compounds of Formula I

| Cmpd # | Compound |
|---|---|
| 236 | |
| 237 | |
| 238 | |
| 239 | |
| 240 | |

TABLE 2-continued
Representative Compounds of Formula I
| Cmpd # | Compound |
|---|---|
| 241 | 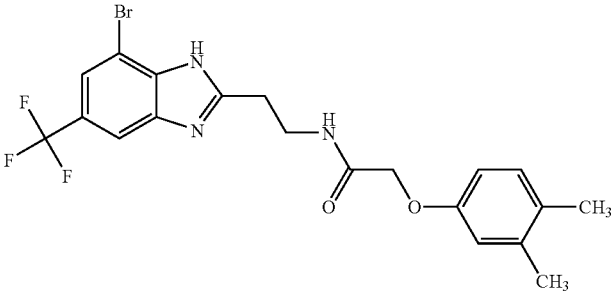 |
| 242 | 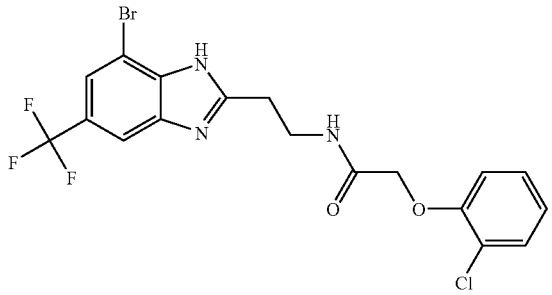 |
| 243 | 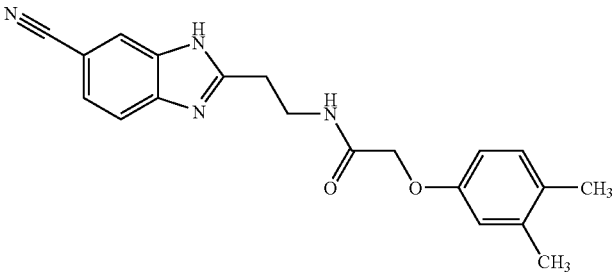 |
| 244 | 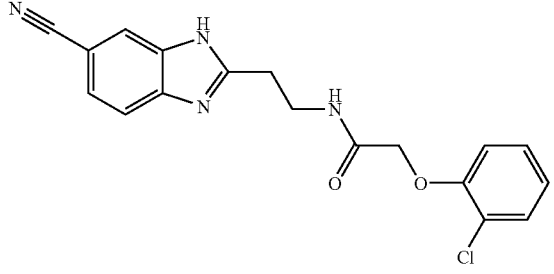 |
| 245 | 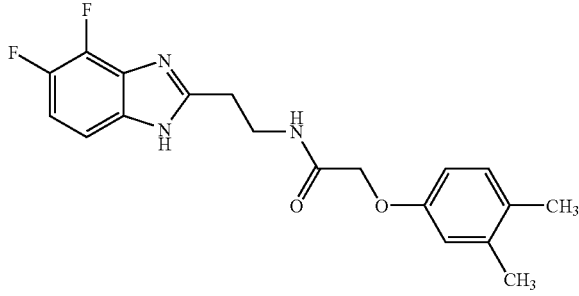 |

TABLE 2-continued

Representative Compounds of Formula I

| Cmpd # | Compound |
|---|---|
| 246 | 4,5-difluoro-benzimidazol-2-yl-ethyl-NH-C(O)-CH2-O-(2-chlorophenyl) |
| 247 | benzimidazol-2-yl-ethyl-NH-C(O)-CH2CH2-(2-chlorophenyl) |
| 249 | benzimidazol-2-yl-ethyl-NH-C(O)-NH-(3,4-dimethylphenyl) |
| 250 | benzimidazol-2-yl-ethyl-NH-C(O)-CH2-(2-chlorophenyl) |
| 251 | benzimidazol-2-yl-ethyl-NH-C(O)-NH-CH2-(2-fluorophenyl) |

TABLE 2-continued

Representative Compounds of Formula I

| Cmpd # | Compound |
|---|---|
| 252 | benzimidazole-CH₂CH₂-NH-C(O)-NH-CH₂-(2-chlorophenyl) |
| 253 | benzimidazole-CH₂CH₂-NH-C(O)-NH-CH₂-(2-methylphenyl) |
| 254 | benzimidazole-CH₂CH₂-NH-C(O)-NH-CH₂-(3,4-dichlorophenyl) |
| 255 | 2-(piperidin-3-yl)benzimidazole, N-piperidinyl-C(O)-CH₂-O-(3,4-dimethylphenyl) |
| 256 | 2-(pyrrolidin-2-ylmethyl)benzimidazole, N-pyrrolidinyl-C(O)-CH₂-O-(3,4-dimethylphenyl) |

TABLE 2-continued
Representative Compounds of Formula I
| Cmpd # | Compound |
|---|---|
| 257 | 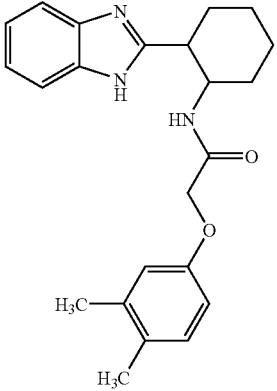 |
| 258 | 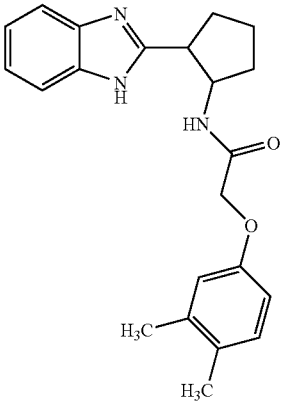 |
| 259 | 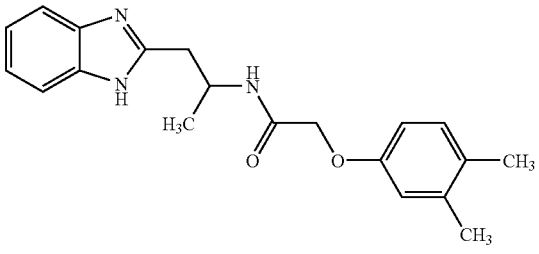 |
| 260 | 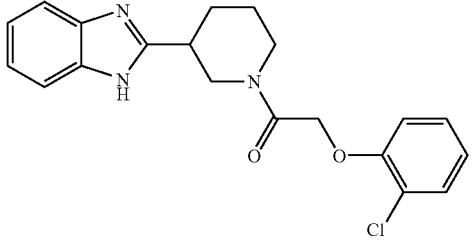 |
| 261 | 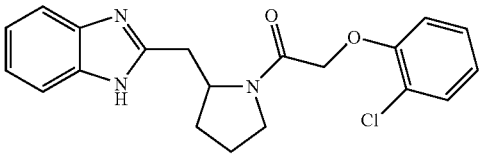 |

TABLE 2-continued
Representative Compounds of Formula I
| Cmpd # | Compound |
|---|---|
| 262 | 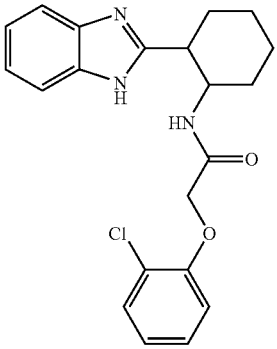 |
| 263 | 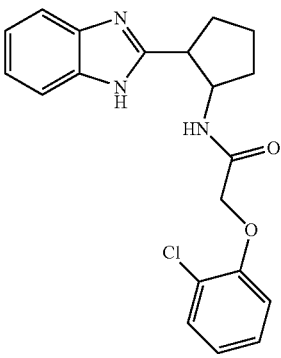 |
| 264 | 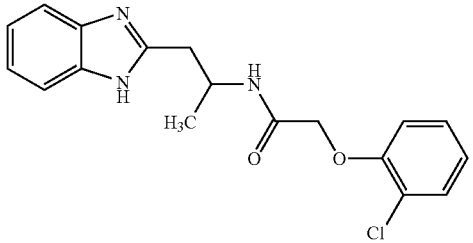 |
| 265 | 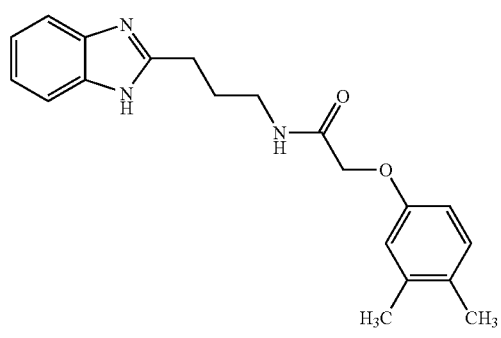 |

TABLE 2-continued
Representative Compounds of Formula I
| Cmpd # | Compound |
|---|---|
| 266 | 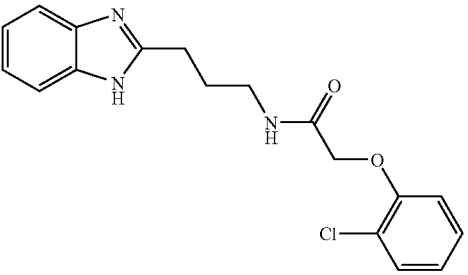 |
| 267 | 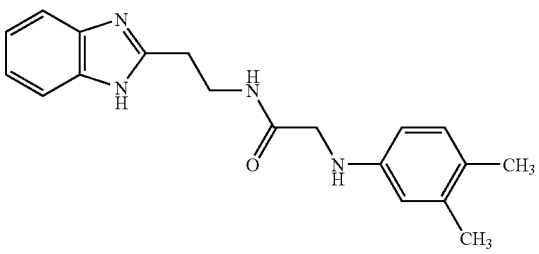 |
| 268 | 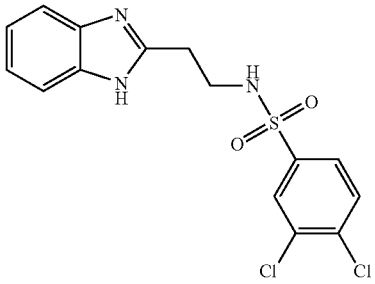 |
| 269 | 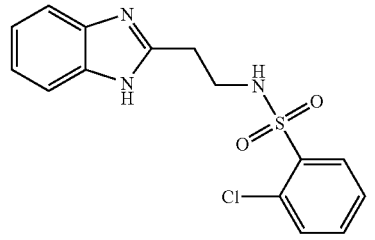 |
| 270 | 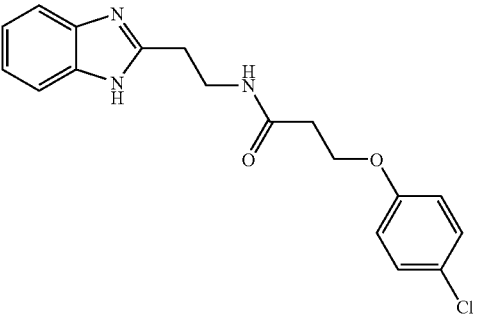 |

TABLE 2-continued

Representative Compounds of Formula I

| Cmpd # | Compound |
|---|---|
| 271 | benzimidazole-CH₂CH₂-NH-C(O)-CH₂CH₂-O-(2,4-difluorophenyl) |
| 272 | benzimidazole-CH₂CH₂-NH-C(O)-CH₂CH₂-O-(4-methoxyphenyl) |
| 273 | benzimidazole-CH₂CH₂-NH-C(O)-CH₂CH₂-O-(4-methylphenyl) |
| 275 | benzimidazole-CH₂CH₂-NH-C(O)-[5-(4-chlorophenyl)furan-2-yl] |
| 276 | benzimidazole-CH₂CH₂-NH-C(O)-(5-bromopyridin-3-yl) |

TABLE 2-continued
Representative Compounds of Formula I
| Cmpd # | Compound |
|---|---|
| 277 | 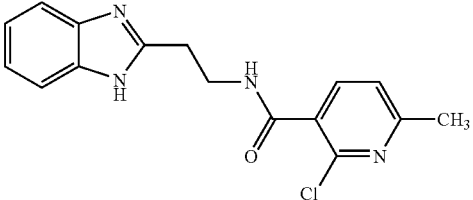 |
| 278 | 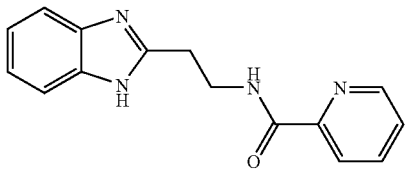 |
| 279 | 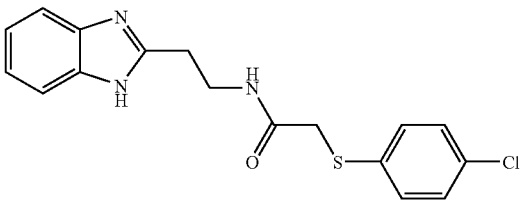 |
| 280 | 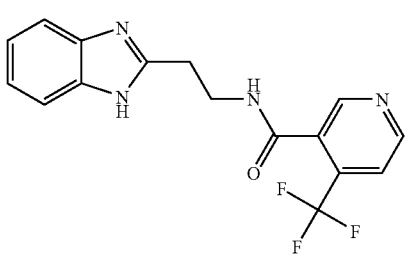 |
| 281 | 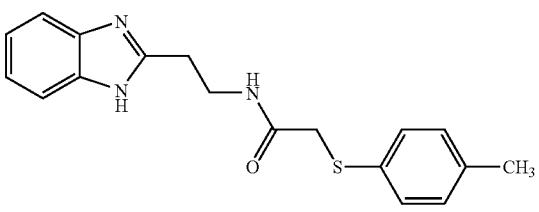 |
| 282 | 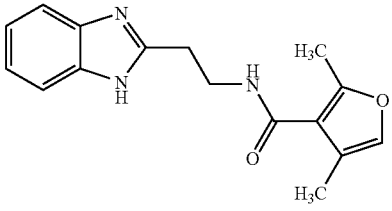 |
| 283 | 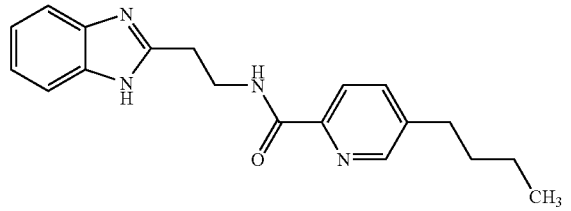 |

TABLE 2-continued

Representative Compounds of Formula I

| Cmpd # | Compound |
|---|---|
| 284 | |
| 285 | |
| 286 | |
| 287 | |
| 288 | |

TABLE 2-continued
Representative Compounds of Formula I
| Cmpd # | Compound |
|---|---|
| 289 | 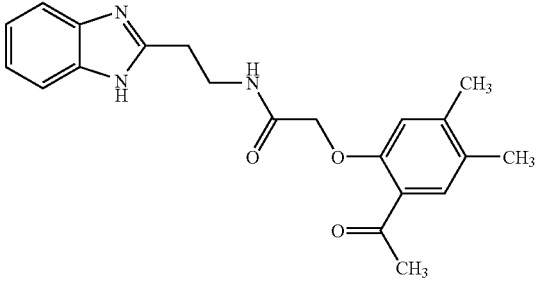 |
| 290 | 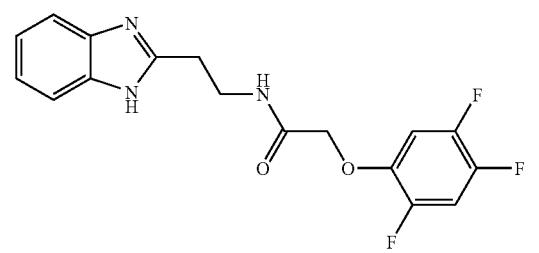 |
| 291 | 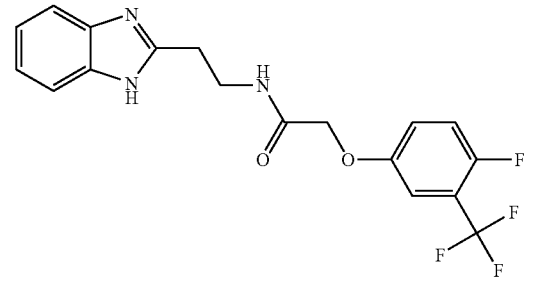 |
| 292 | 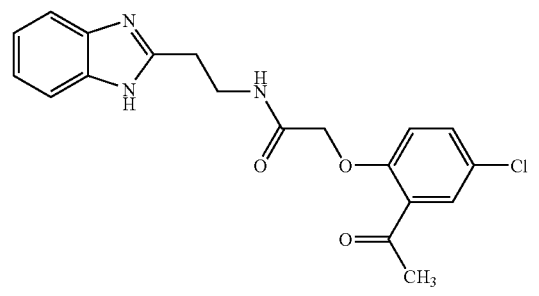 |
| 293 | 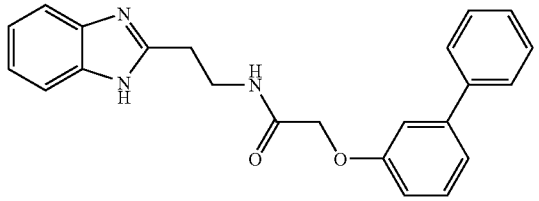 |

TABLE 2-continued
Representative Compounds of Formula I
| Cmpd # | Compound |
|---|---|
| 294 | 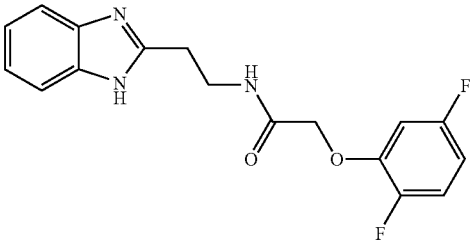 |
| 295 | 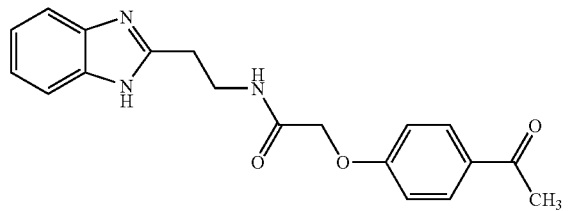 |
| 296 | 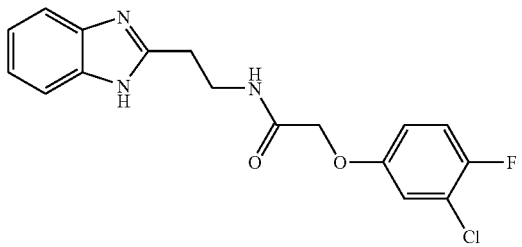 |
| 297 | 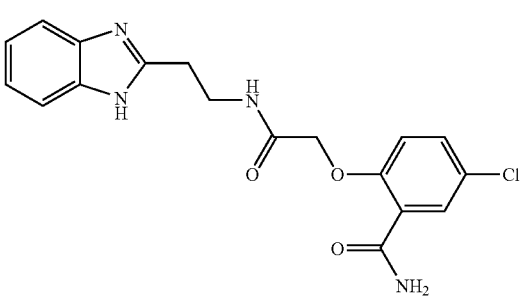 |
| 298 | 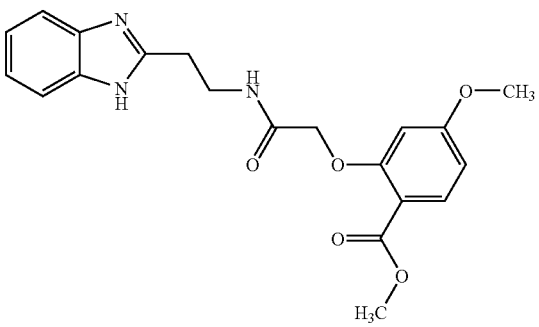 |

TABLE 2-continued

Representative Compounds of Formula I

| Cmpd # | Compound |
|---|---|
| 299 | |
| 300 | |
| 301 | |
| 302 | |

TABLE 2-continued
Representative Compounds of Formula I
| Cmpd # | Compound |
|---|---|
| 303 | 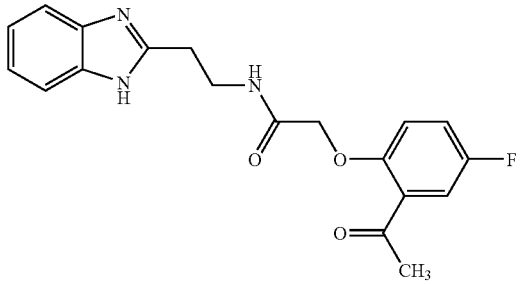 |
| 304 | 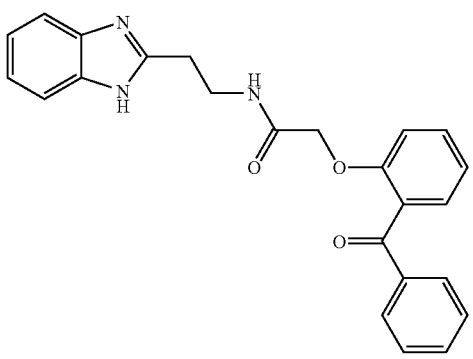 |
| 305 | 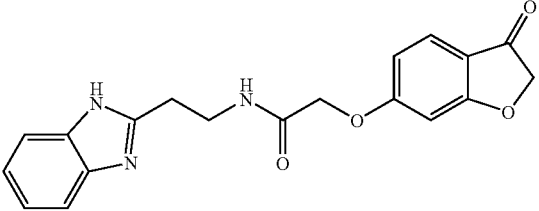 |
| 306 | 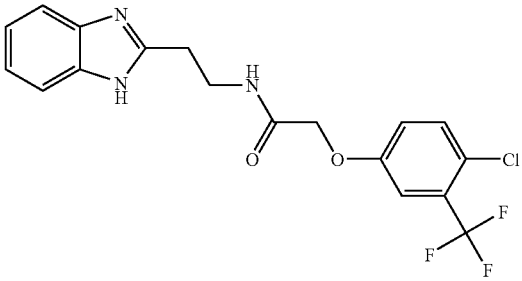 |
| 307 | 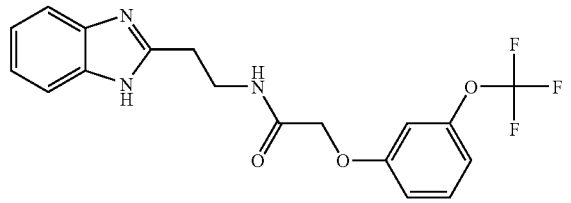 |

TABLE 2-continued

Representative Compounds of Formula I

| Cmpd # | Compound |
|---|---|
| 308 | |
| 309 | |
| 310 | |
| 311 | |
| 312 | |

TABLE 2-continued
Representative Compounds of Formula I
| Cmpd # | Compound |
|---|---|
| 313 | 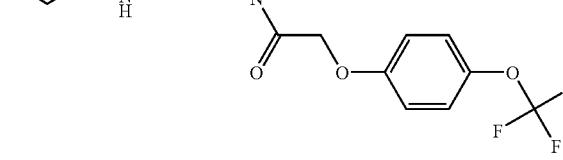 |
| 314 | 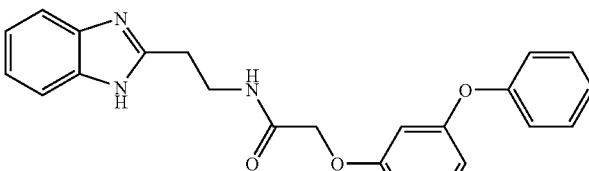 |
| 315 | 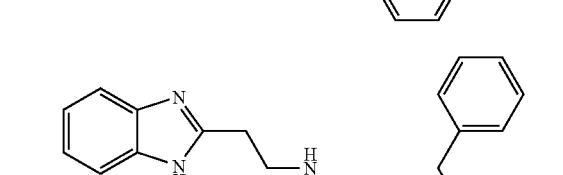 |
| 316 | 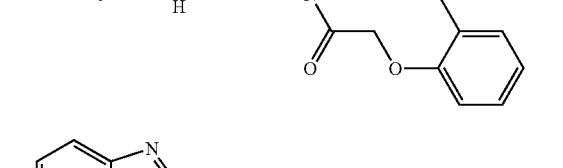 |
| 317 | 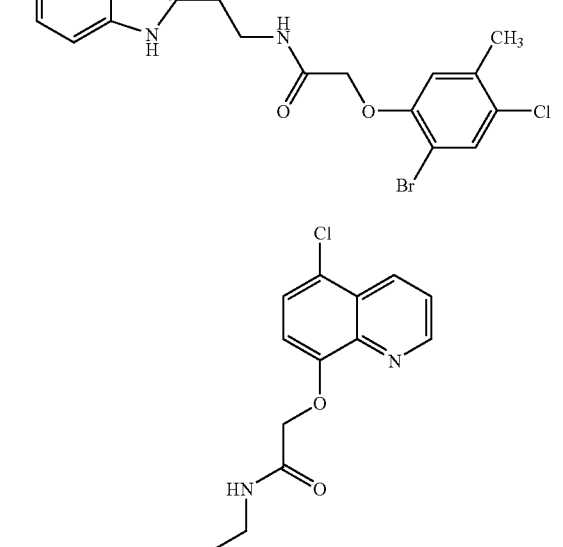 |

TABLE 2-continued
Representative Compounds of Formula I
| Cmpd # | Compound |
|---|---|
| 318 | 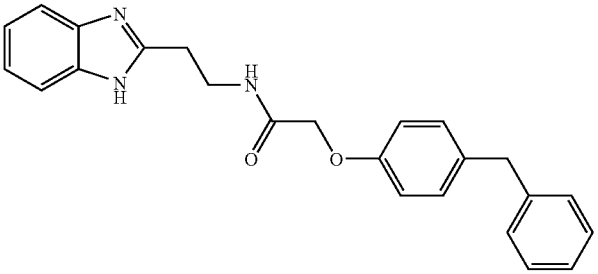 |
| 319 | 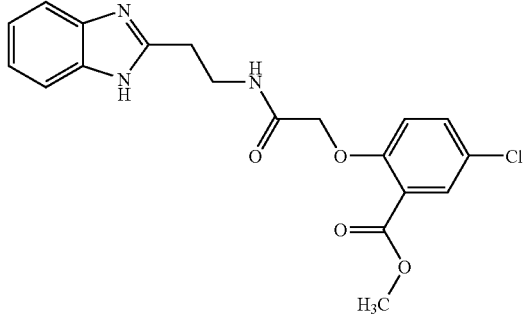 |
| 320 | 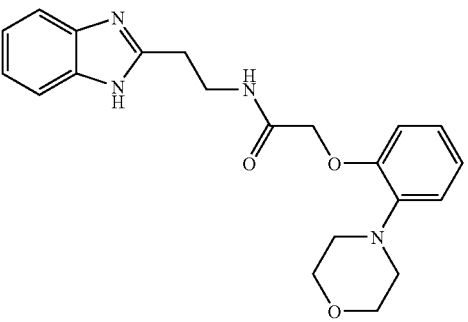 |
| 321 | 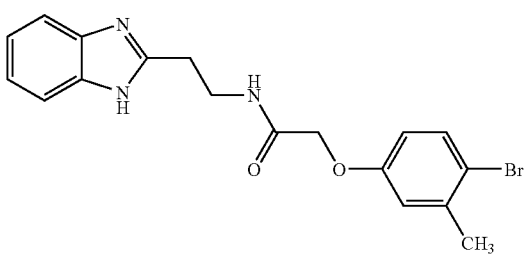 |
| 322 | 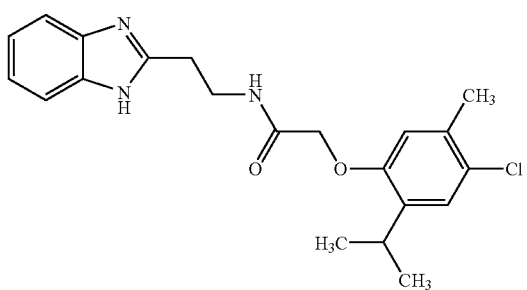 |

TABLE 2-continued
Representative Compounds of Formula I
| Cmpd # | Compound |
|---|---|
| 323 | 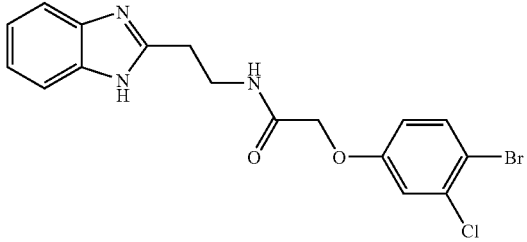 |
| 324 | 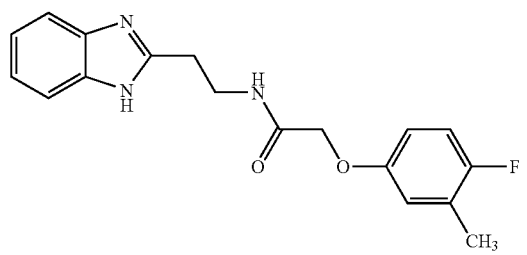 |
| 325 | 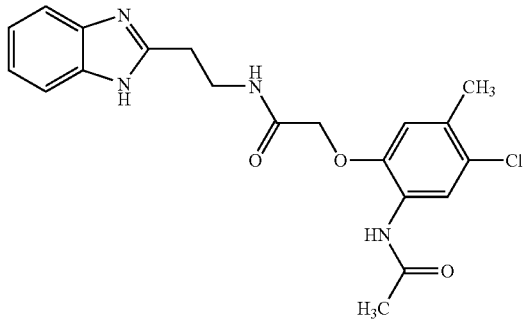 |
| 326 | 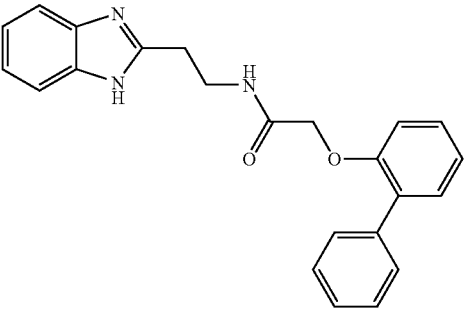 |
| 327 | 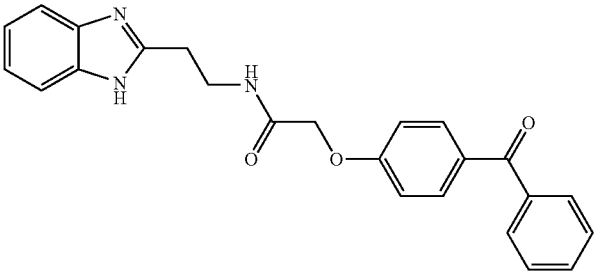 |

TABLE 2-continued

Representative Compounds of Formula I

| Cmpd # | Compound |
|---|---|
| 328 | benzimidazole-CH₂CH₂-NH-C(O)-CH₂-O-(2,4,5-trichlorophenyl) |
| 329 | quinolin-5-yl-O-CH₂-C(O)-NH-CH₂CH₂-benzimidazole |
| 330 | benzimidazole-CH₂CH₂-NH-C(O)-CH₂-O-(3-acetylphenyl) |
| 331 | benzimidazole-CH₂CH₂-NH-C(O)-CH₂-O-quinolin-6-yl |
| 332 | benzimidazole-CH₂CH₂-NH-C(O)-CH₂-O-(3-morpholinophenyl) |

TABLE 2-continued
Representative Compounds of Formula I
| Cmpd # | Compound |
|---|---|
| 333 | 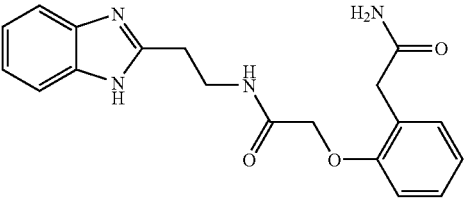 |
| 334 | 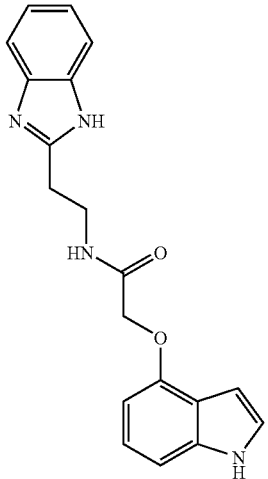 |
| 335 | 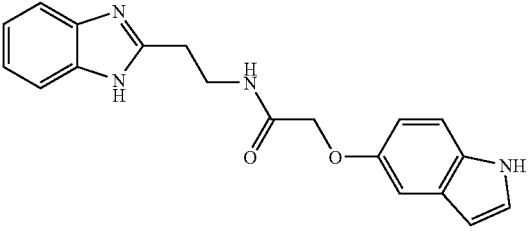 |
| 336 | 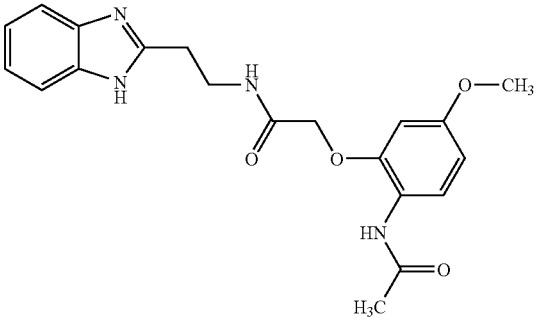 |
| 337 | 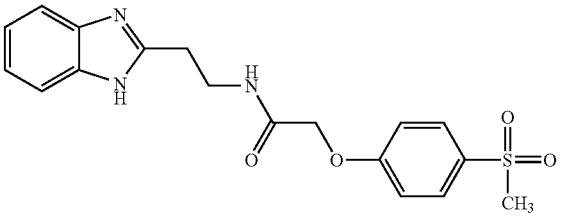 |

TABLE 2-continued

Representative Compounds of Formula I

| Cmpd # | Compound |
|---|---|
| 338 | |
| 339 | |
| 340 | |
| 341 | |
| 342 | |

US 7,705,031 B2
TABLE 2-continued
Representative Compounds of Formula I
| Cmpd # | Compound |
|---|---|
| 343 | 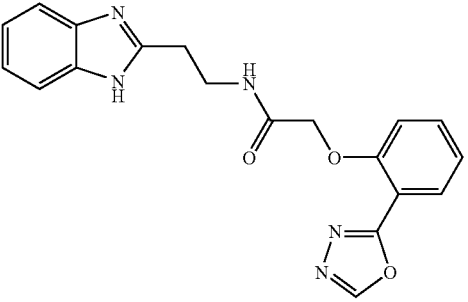 |
| 344 | 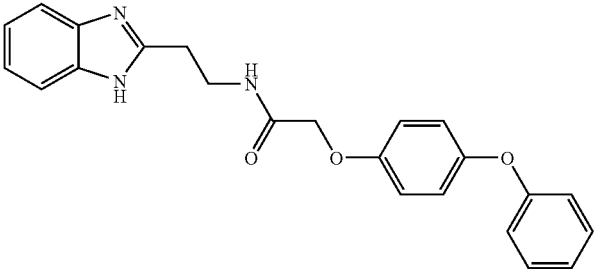 |
| 345 | 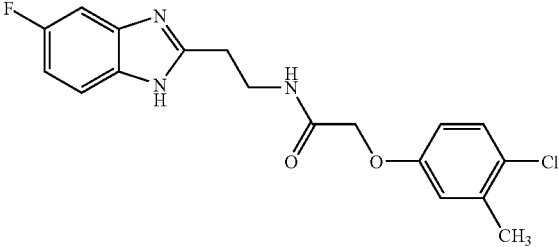 |
| 346 | 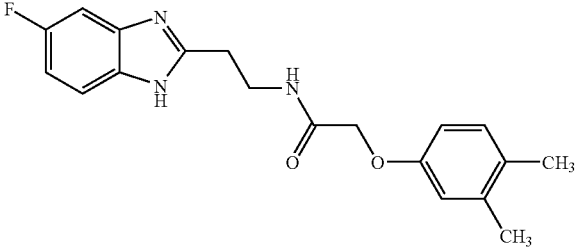 |
| 347 | 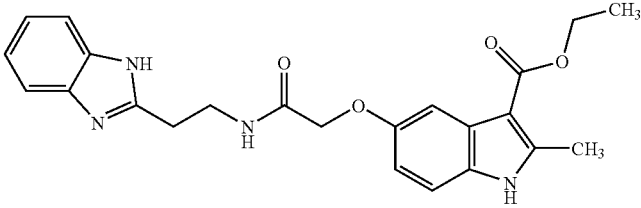 |

US 7,705,031 B2
145	146
TABLE 2-continued
Representative Compounds of Formula I
| Cmpd # | Compound |
|---|---|
| 348 | 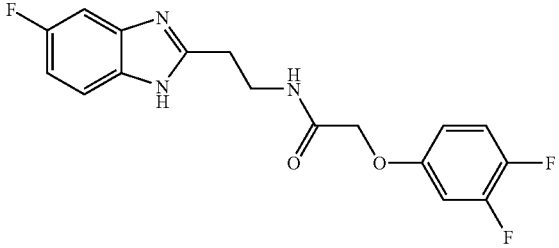 |
| 349 | 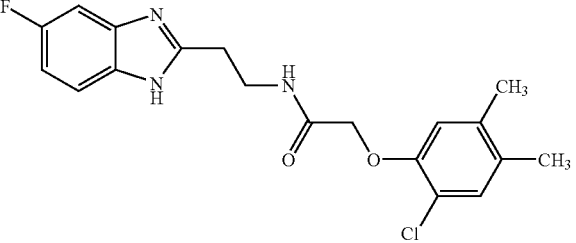 |
| 350 | 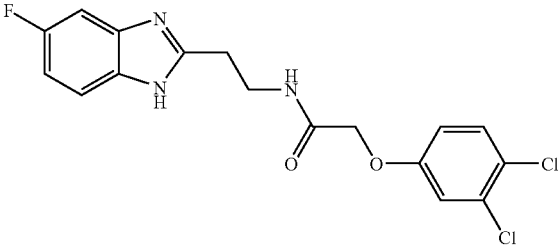 |
| 351 | 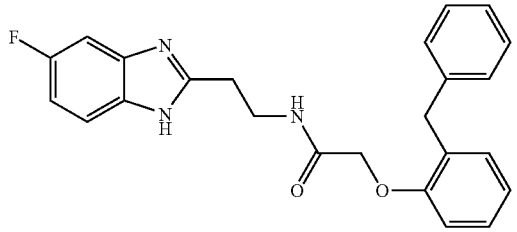 |
| 352 | 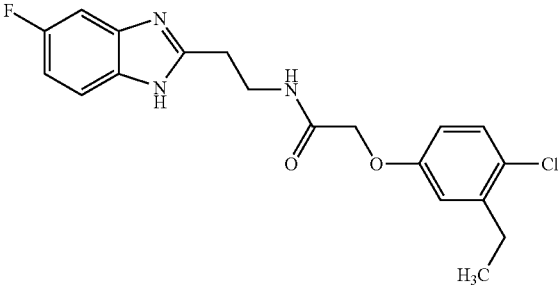 |

TABLE 2-continued
Representative Compounds of Formula I
| Cmpd # | Compound |
|---|---|
| 353 | 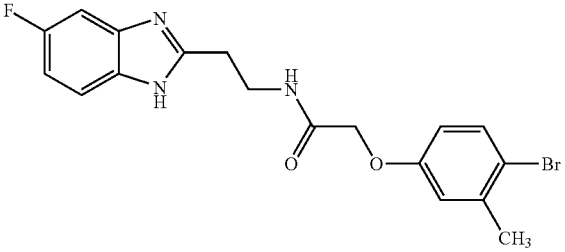 |
| 354 | 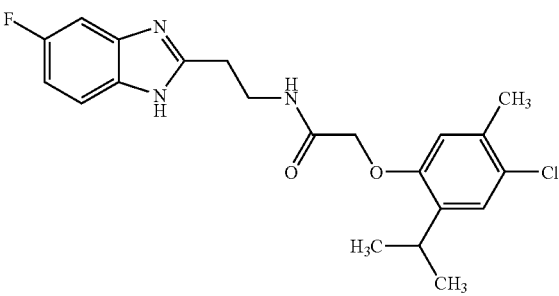 |
| 355 | 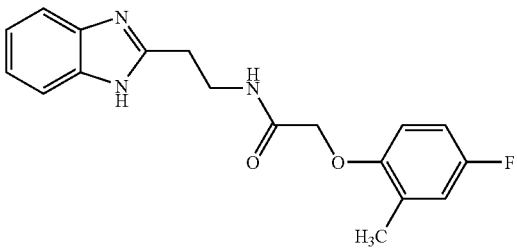 |
| 356 | 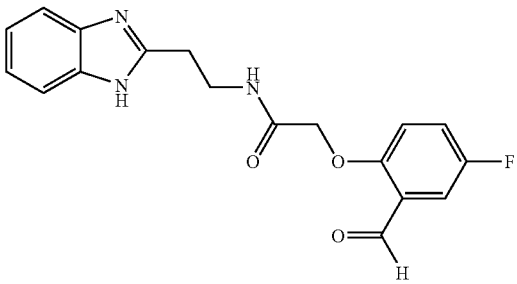 |
| 357 | 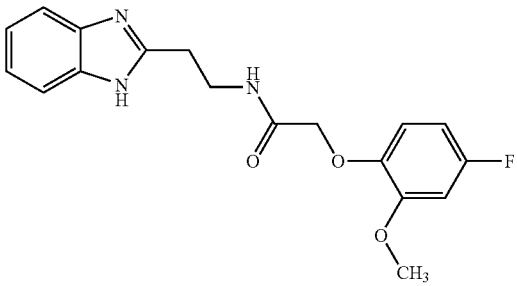 |

TABLE 2-continued
Representative Compounds of Formula I
| Cmpd # | Compound |
|---|---|
| 358 | 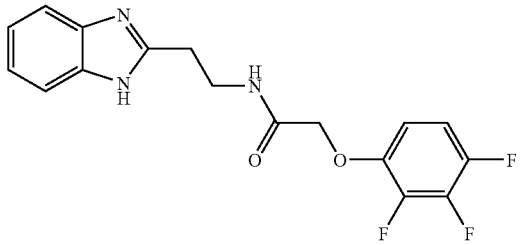 |
| 359 | 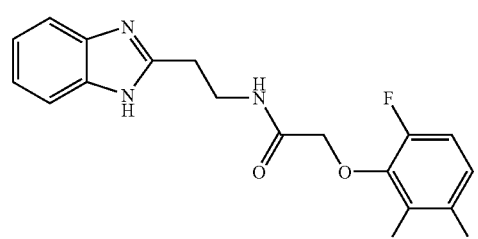 |
| 360 | 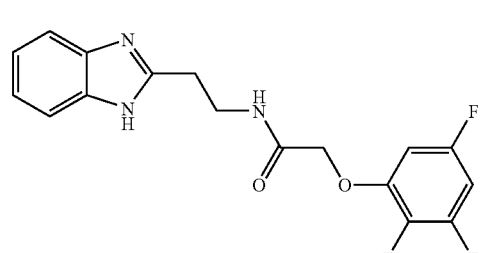 |
| 361 | 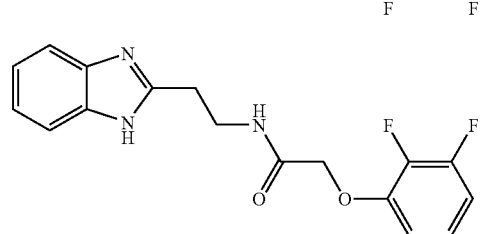 |
| 362 | 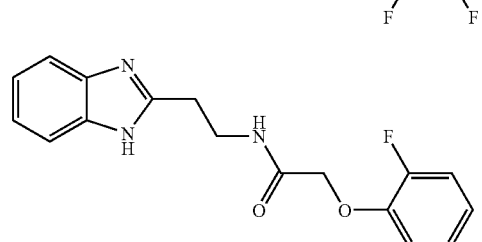 |
| 363 | 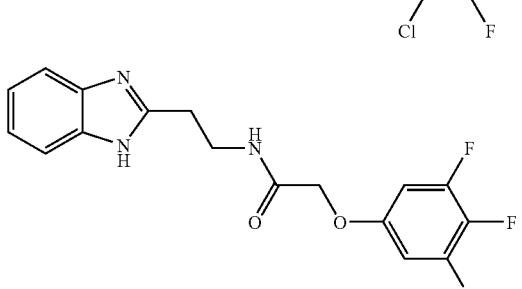 |

TABLE 2-continued

Representative Compounds of Formula I

| Cmpd # | Compound |
|---|---|
| 366 | 5-fluoro-1H-indole-2-carboxylic acid (3-sulfamoyl-phenyl)-amide |
| 367 | 5-chloro-1H-indole-2-carboxylic acid (3-sulfamoyl-phenyl)-amide |
| 368 | 1H-indole-2-carboxylic acid (3-sulfamoyl-phenyl)-amide |
| 369 | 1-methyl-1H-indole-2-carboxylic acid (3-sulfamoyl-phenyl)-amide |
| 370 | 3,5-dimethyl-1H-indole-2-carboxylic acid (3-sulfamoyl-phenyl)-amide |

Although certain exemplary embodiments are depicted and described above and herein, it will be appreciated that a compounds of the invention can be prepared according to the methods described generally above using appropriate starting materials by methods generally available to one of ordinary skill in the art.

4. General Synthetic Methodology

The compounds of this invention may be prepared in general by methods known to those skilled in the art for analogous compounds, as illustrated by the general schemes below, and the preparative examples that follow. Starting materials are commercially available from typical chemical reagent supply companies, such as, Aldrich Chemicals Co., Sigma Chemical Company and the like. Compounds that are not commercially available can be prepared by one of ordinary skill in art following procedures set forth in references such as, "Fieser and Fieser's Reagents for Organic Synthesis", Volumes 1-15, John Wiley and Sons, 1991; "Rodd's Chemistry of Carbon Compounds", Volumes 1-5 and Supplementals, Elsevier Science Publishers, 1989; and "Organic Reactions", Volumes 1-40, John Wiley and Sons, 1991.

Scheme 1

Scheme 1 teaches the general preparation of compounds of Formula I. Typically compounds of Formula I, where Y or W is

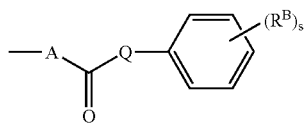

wherein A is —NH—, or —N($C_{1-6}$alkyl)- are prepared by the coupling of optionally substituted compounds of Formula A, which has a nucleophilic function with optionally substituted compounds of Formula B, which have a terminal electrophilic functionality, such as a carboxylic acid, sulfonyl halide, isocyanate, or the like, as defined previously. These methods are also applicable to compounds of Formulas II and III as defined previously.

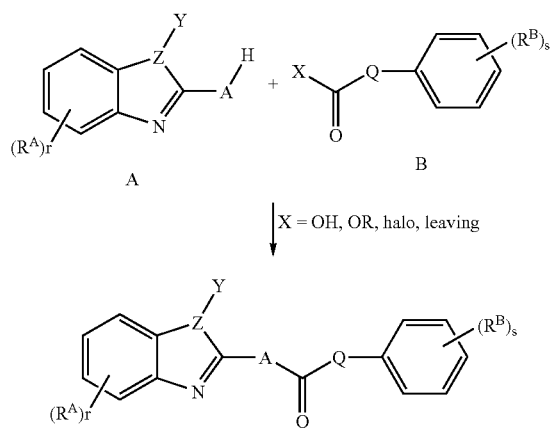

Synthetic Scheme 2a, 2b:

Scheme 2a teaches the preparation of optionally substituted benzimidazole compounds of Formula II. Scheme 2b teaches the preparation of additional optionally substituted benzimidazole compounds of formula II.

Scheme 2a

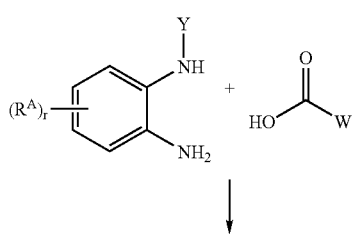

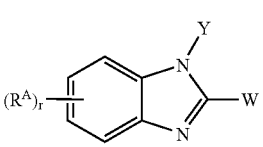

Scheme 2b

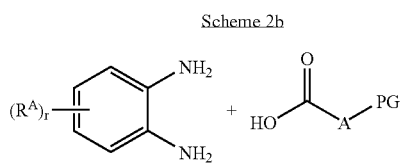

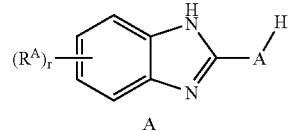

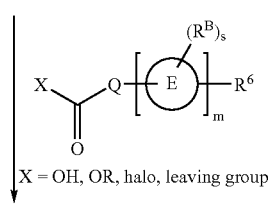

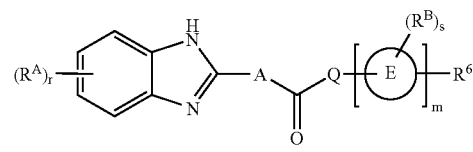

An optionally substituted 1,2-diaminobenzene is reacted with an optionally substituted carboxylic acid with a protected nucleophilic group to provide the benzimidazole intermediate, which is then cyclized to form the benzimidazole moiety. The nucleophilic group is deprotected and acylated, sulfonylated, carbamoylated, or alkylated to provide compounds of Formula II.

Synthetic Scheme 3a, 3b, 3c:

Scheme 3a teaches the preparation of optionally substituted aryloxy acids. Optionally substituted aryloxy acids are prepared by reacting optionally substituted phenolic compounds with optionally substituted halo-substituted alkyl esters (X is Cl, Br or I) to obtain the corresponding ester.

Scheme 3a

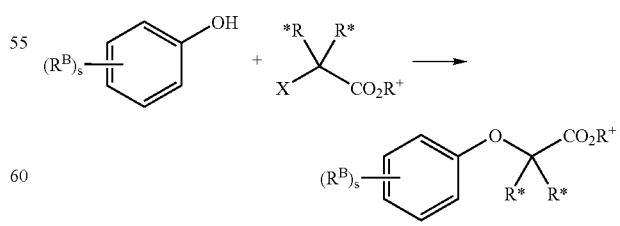

The ester compound is then hydrolyzed to obtain a desired optionally substituted compound of Formula B.

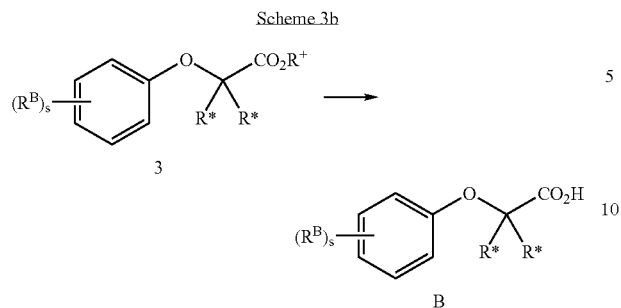

As taught in Schemes 1, 2a, and 2b, compounds of Formula A and B are reacted together to obtain compounds of Formula I. For example, Formula A as taught in Scheme 2b and Formula B as taught in the present Scheme 3b can be reacted to form the corresponding compound of Formula I (Scheme 3c).

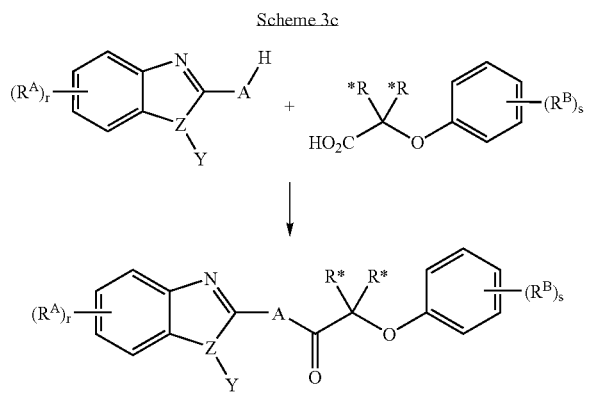

Synthetic Scheme 4:

Following the procedures taught in Schemes 1, 2a, 2b, 3a, 3b, and 3c, and using an optionally substituted aryl isocyanate compound of Formula B,

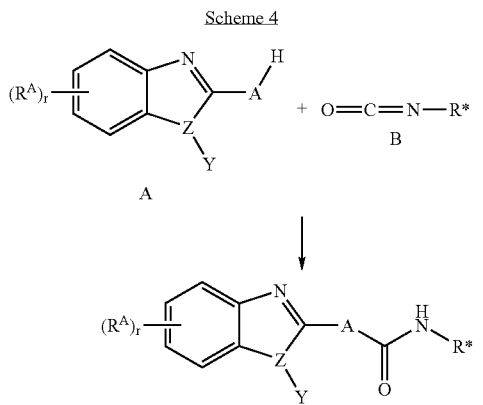

optionally substituted compounds of Formula I are obtained.

Synthetic Scheme 5:

Following the procedures taught in Schemes 1, 2a, 2b, 3a, 3b, and 3c, and using an optionally substituted aryl sulfonyl chloride compound of Formula B,

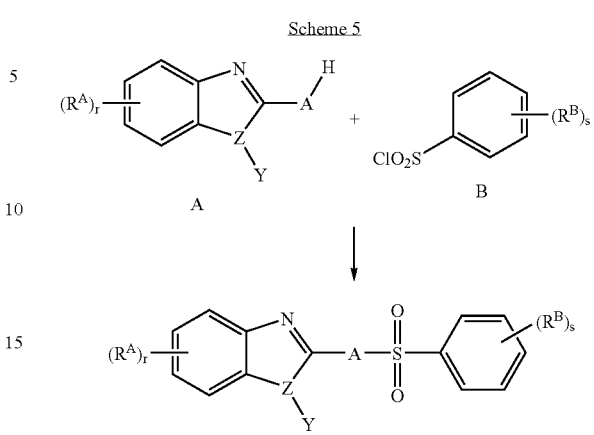

optionally substituted compounds of Formula I are obtained.

Synthetic Scheme 6:

Protected optionally substituted benzimidazoles of Formula A are prepared by reacting a starting cyano substituted benzimidazole with $(Boc)_2O$ followed by reduction of the cyano group (Raney-Nickel/$H_2$ or the like) to provide the desired compound of Formula A.

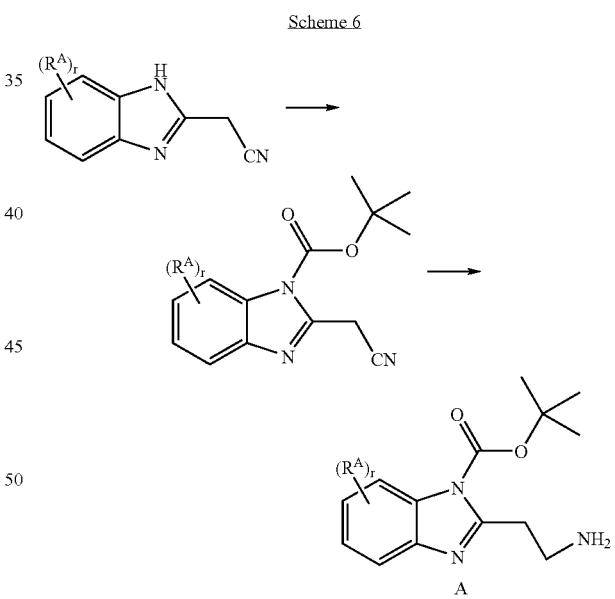

As taught previously in Schemes 1, 2a, 2b, 3a, 3b, 3c, 4 and 5, compounds of Formula A from the present Scheme 6 are derivatized to provide the corresponding compounds of Formula I.

Synthetic Schemes 7a, 7b:

An optionally substituted benzyl alcohol is reacted with phosgene to provide an optionally substituted compound of Formula B2.

Scheme 7a

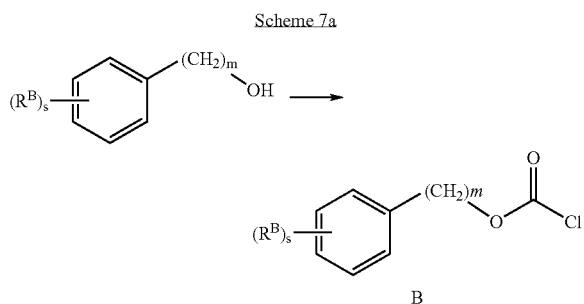

This compound is then reacted with a compound of Formula A to provide the corresponding compound of Formula I. For example, where the compound of Formula A is a benzimidazole taught in Scheme 2, the following compounds of Formula I, where s is 0 to 4, and m is 1 or 4, as it corresponds to Q where Q is —O—C$_{1-4}$alkyl are obtained.

Scheme 7b

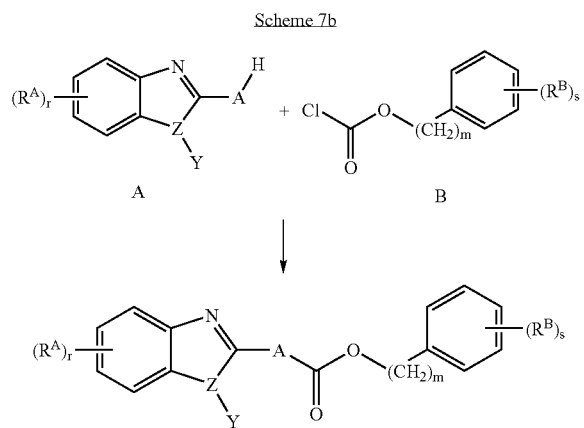

Synthetic Scheme 8:

A compound of Formula I, where W is

is prepared by reacting an optionally substituted di-amino benzene with an optionally substituted benzaldehyde or benzoic acid to obtain the corresponding optionally substituted compound of Formula I, where $R^A$, $R^D$, r and t are as taught for Formula I, in a manner analogous to Schemes 2a and 2b.

Although certain exemplary embodiments are depicted and described above and herein, it will be appreciated that a compounds of the invention can be prepared according to the methods described generally above using appropriate starting materials by methods generally available to one of ordinary skill in the art.

5. Uses, Formulation and Administration

In yet another aspect, a method for the treatment or lessening the severity of acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, or incontinence is provided comprising administering an effective amount of a compound, or a pharmaceutically acceptable composition comprising a compound to a subject in need thereof. In certain preferred embodiments, a method for the treatment or lessening the severity of acute, chronic, neuropathic, or inflammatory pain is provided comprising administering an effective amount of a compound or a pharmaceutically acceptable composition to a subject in need thereof. In certain embodiments of the present invention an "effective amount" of the compound or pharmaceutically acceptable composition is that amount effective for treating or lessening the severity of one or more of acute, chronic, neuropathic, or inflammatory pain, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, or incontinence.

As described generally above, the compounds of the invention are useful as inhibitors of voltage-gated sodium ion channels or calcium channels, preferably N-type calcium channels. In one embodiment, the compounds and compositions of the invention are inhibitors of one or more of NaV1.1, NaV1.2, NaV1.3, NaV1.4, NaV1.5, NaV1.6, NaV1.7, NaV1.8, NaV1.9, or CaV2.2, and thus, without wishing to be bound by any particular theory, the compounds and compositions are particularly useful for treating or lessening the severity of a disease, condition, or disorder where activation or hyperactivity of one or more of NaV1.1, NaV1.2, NaV1.3, NaV1.4, NaV1.5, NaV1.6, NaV1.7, NaV1.8, NaV1.9, or CaV2.2 is implicated in the disease, condition, or disorder. When activation or hyperactivity of NaV1.1, NaV1.2, NaV1.3, NaV1.4, NaV1.5, NaV1.6, NaV1.7, NaV1.8, NaV1.9, or CaV2.2, is implicated in a particular disease, condition, or disorder, the disease, condition, or disorder may also be referred to as a "NaV1.1, NaV1.2, NaV1.3, NaV1.4, NaV1.5, NaV1.6, NaV1.7, NaV1.8, NaV1.9, or CaV2.2-mediated disease, condition or disorder" or a "CaV2.2-mediated condition or disorder". Accordingly, in another aspect, the present invention provides a method for treating or lessening the severity of a disease, condition, or disorder where activation or hyperactivity of one or more of NaV1.1, NaV1.2, NaV1.3, NaV1.4, NaV1.5, NaV1.6, NaV1.7, NaV1.8, NaV1.9, or CaV2.2 is implicated in the disease state.

The activity of a compound utilized in this invention as an inhibitor of NaV1.1, NaV1.2, NaV1.3, NaV1.4, NaV1.5, NaV1.6, NaV1.7, NaV1.8, NaV1.9, or CaV2.2 may be assayed according to methods described generally in the Examples herein, or according to methods available to one of ordinary skill in the art.

In certain exemplary embodiments, compounds of the invention are useful as inhibitors of NaV1.8. In other embodiments, compounds of the invention are useful as inhibitors of NaV1.8 and CaV2.2. In still other embodiments, compounds of the invention are useful as inhibitors of CaV2.2.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of a voltage-gated sodium ion channel.

Pharmaceutically acceptable salts are well known in the art. For example, S. M. Berge, et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Pharmaceutically Acceptable Compositions

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, a method for the treatment or lessening the severity of acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, or incontinence is provided comprising administering an effective amount of a compound, or a pharmaceutically acceptable composition comprising a compound to a subject in need thereof. In certain preferred embodiments, a method for the treatment or lessening the severity of acute, chronic, neuropathic, or inflammatory pain is provided comprising administering an effective amount of a compound or a pharmaceutically acceptable composition to a subject in need thereof. In certain embodiments of the present invention an "effective amount" of the compound or pharmaceutically acceptable composition is that amount effective for treating or lessening the severity of one or more of acute, chronic, neuropathic, or inflammatory pain, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, or incontinence.

The compounds and compositions, according to the method of the present invention, may be administered using any amount and any route of administration effective for treating or lessening the severity of one or more of acute, chronic, neuropathic, or inflammatory pain, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, or incontinence. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of voltage-gated sodium ion channels. In one embodiment, the compounds and compositions of the invention are inhibitors of one or more of NaV1.1, NaV1.2, NaV1.3, NaV1.4, NaV1.5, NaV1.6, NaV1.7, NaV1.8, NaV1.9, or CaV2.2 and thus, without wishing to be bound by any particular theory, the compounds and compositions are particularly useful for treating or lessening the severity of a disease, condition, or disorder where activation or hyperactivity of one or more of NaV1.1, NaV1.2, NaV1.3, NaV1.4, NaV1.5, NaV1.6, NaV1.7, NaV1.8, NaV1.9, or CaV2.2 is implicated in the disease, condition, or disorder. When activation or hyperactivity of NaV1.1, NaV1.2, NaV1.3, NaV1.4, NaV1.5, NaV1.6, NaV1.7, NaV1.8, NaV1.9, or CaV2.2 is implicated in a particular disease, condition, or disorder, the disease, condition, or disorder may also be referred to as a "NaV1.1, NaV1.2, NaV1.3, NaV1.4, NaV1.5, NaV1.6, NaV1.7, NaV1.8, NaV1.9, or CaV2.2-mediated disease, condition or disorder". Accordingly, in another aspect, the present invention provides a method for treating or lessening the severity of a disease, condition, or disorder where activation or hyperactivity of one or more of NaV1.1, NaV1.2, NaV1.3, NaV1.4, NaV1.5, NaV1.6, NaV1.7, NaV1.8 or NaV1.9 is implicated in the disease state.

The activity of a compound utilized in this invention as an inhibitor of NaV1.1, NaV1.2, NaV1.3, NaV1.4, NaV1.5, NaV1.6, NaV1.7, NaV1.8, NaV1.9, or CaV2.2 may be assayed according to methods described generally in the Examples herein.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to inhibiting NaV1.1, NaV1.2, NaV1.3, NaV1.4, NaV1.5, NaV1.6, NaV1.7, NaV1.8, NaV1.9, or CaV2.2 activity in a biological sample or a patient, which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof, and blood, saliva, urine, feces, semen, tears, or other body fluids or extracts thereof.

Inhibition of NaV1.1, NaV1.2, NaV1.3, NaV1.4, NaV1.5, NaV1.6, NaV1.7, NaV1.8, NaV1.9, or CaV2.2 activity in a biological sample is useful for a variety of purposes that are known to one of skill in the art. Examples of such purposes include, but are not limited to, the study of sodium ion channels in biological and pathological phenomena; and the comparative evaluation of new sodium ion channel inhibitors.

In order that the invention described herein may be more fully understood, the following examples are set forth. It should be understood that these examples are for illustrative purposes only and are not to be construed as limiting this invention in any manner.

EXAMPLES

Synthesis of Exemplary Compounds of the Invention

Example 1

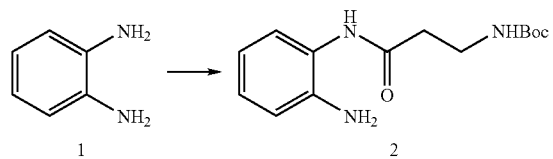

This example teaches the preparation of [2-(1-methyl-1H-benzoimidazol-2-yl)-ethyl]-carbamic acid tert-butyl ester (6). To a solution of beta-alanine (3.5 g, 18.5 mmol) and pyridine (3 mL, 37 mmol) in dichloromethane (20 mL) was added PFP ester (3.2 mL, 18.5 mmol). After stirring at room temperature for 1 hour, 1,2-phenyleneamine 1 (2 g, 18.5 mmol) in dichloromethane (20 mL) was added to the reaction mixture. After stirring overnight, the reaction was quenched with water, extracted with dichloromethane (150 mL*2), dried and removed the solvent. Then the crude mixture was triturated with dichloromethane (20 mL), filtered to give white solid 2 as the desired product (4.8 g) at 90% yield. LC/MS (10-99%) M+1/Z 280.3 retention time 2.03 min.

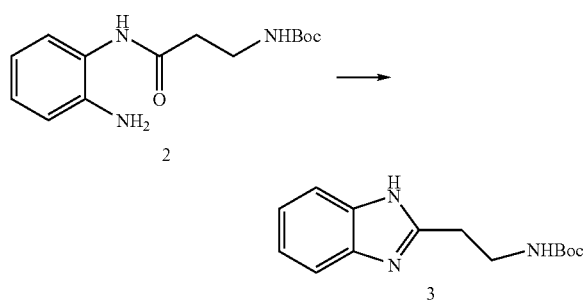

Compound 2 (4 g) was dissolved in acetic acid (50 mL) and heated to 65° C. for 1 h, then cooled down to room temperature, removed the solvent in vacuo. The residue was taken up with dichloromethane, quenched with sat NaHCO$_3$, extracted with dichloromethane (150 mL) (pH=10), concentrated to afford 3 as light yellow solid (3.7 g) at 100% yield. LC/MS (10-99%) M+1/Z 262.2 retention time 2.30 min.

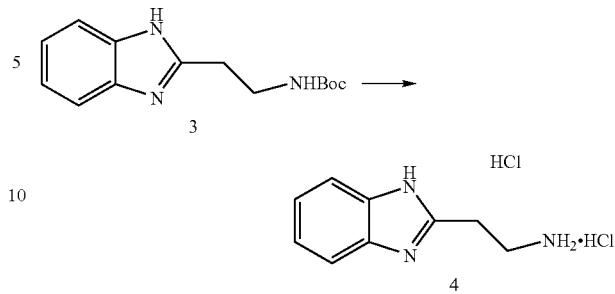

Compound 3 (3 g) was dissolved in 3 N HCl/EtOAC (50 mL/25 mL) and stirred at room temperature overnight. The solvent was in vacuo and dried in high vacuum to give compound 4 as pink solid (2.4 g) at greater than 95% yield. LC/MS (10-99%) M+1/Z 162.4 retention time 0.62 min.

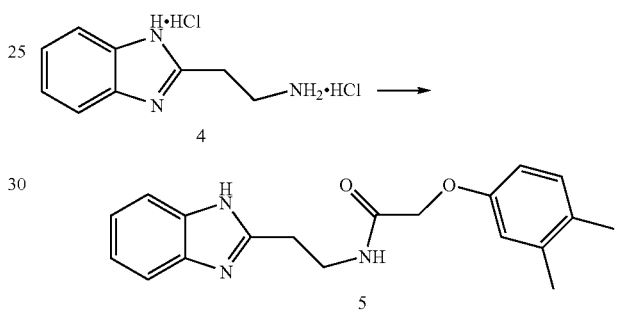

To a solution of benzimidazole ethylene amine dihydrochloride (100 mg, 0.43 mmol), 3,4-dimethylphenoxyacetic acid (77 mg, 0.43 mmol), and BOP reagent (190 mg, 0.43 mmol) in acetonitrile (5 mL) was added triethylamine (0.23 mL, 1.72 mmol). After stirring at room temperature overnight, the solvent was removed under vacuum. The residue was taken up with water and saturated sodium bicarbonate (20 mL), extracted with dichloromethane (30 mL×2), dried and removed the solvent. The crude mixture was purified by using Gilson HPLC to give white solid 5 as a TFA salt (170 mg) at 93% yield. MUX LC/MS (10-99%) M+1/Z 324.163 retention time 2.62 min; $^1$H NMR (DMSO) δ 2.12 (s, 3H), δ 2.15 (s, 3H), δ 2.99 (t, 2H, J=5.88 Hz), δ 3.59 (m, 2H), δ 4.40 (s, 2H), δ 6.64 (dd, 1H, J=2 Hz, 6.5 Hz), δ 6.75 (d, 1H, J=1.8 Hz), δ 6.98 (6, 1H, J=6.6 Hz), δ 7.12 (m, 2H), 7.40 (d, 1H, J=5.76 Hz), 7.53 (m, 1H), 8.30 (t, 1H, J=4.56 Hz), 12.24 (s, 1H); $^{13}$C NMR (DMSO) δ 18.4, δ 19.57, δ 28.58, δ 36.74, δ 67.07, δ 110.8, δ 111.58, δ 116.13, δ 118.12, δ 120.86, δ 121.52, δ 128.70, δ 130.12, δ 134.21, δ 137.25, δ 143.24, δ 152.74, δ 155.73, δ 167.85.

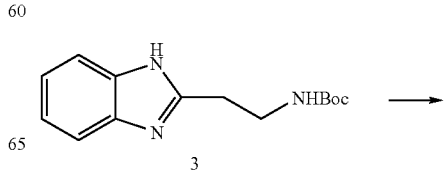

-continued

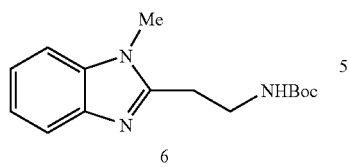

Boc-protected benzimidazole ethyl amine 3 (400 mg, 1.53 mmol) was dissolved in THF (50 mL) and cooled to 0° C. under nitrogen, followed by dropwise addition of LiHMDS (535 mg, 3.37 mmol) in THF (10 mL) via syringe. The mixture was warmed to room temperature and stirred for 20 min. Methyl iodide (0.1 mL, 1.68 mmol) was added dropwise to the reaction mixture. After stirring for 5 h at room temperature, the reaction was quenched with water (20 mL) and extracted with EtOAc (30 mL×2), dried, concentrated and purified by ISCO flash chromatography.

Example 2

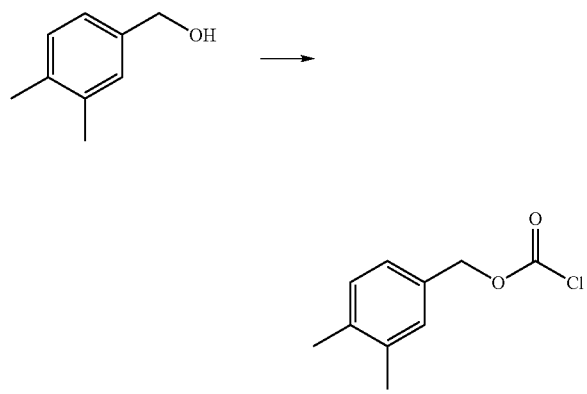

This example teaches the preparation of [2-(1H-benzoimidazol-2-yl)-ethyl]-carbamic acid 3,4-dimethyl-benzyl ester. To a solution of 3,4-dimethylbenzyl alcohol (1.5 g, 11.0 mmol) in toluene (20 mL) was added phosgene (13 mL, 24.3 mmol, 20% in toluene). After stirring at room temperature overnight, excess phosgene and toluene was removed in vacuo, and dried under high vacuum for 2 h. providing 3,4-dimethylbenzylchloroformate (1.8 g) as an oil at 80% yield. (reference: Nägele, E.; Schelhaas, M.; Kuder, N.; Waldmann, H. *J. Am. Chem. Soc.* 1998, 120, 6889)

Example 3

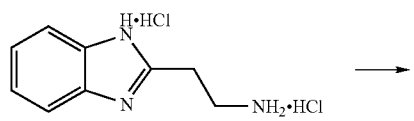

-continued

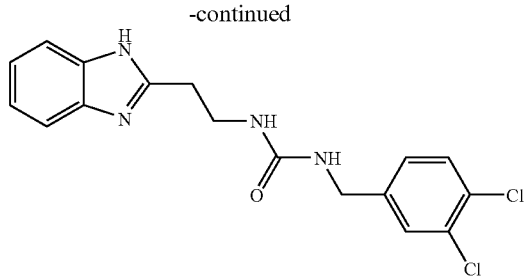

This example teaches the preparation of 1-[2-(1H-benzoimidazol-2-yl)-ethyl]-3-(3,4-dichloro-benzyl)-urea. To a solution of benzimidazole ethyl amine dihydrochloride (50 mg, 0.21 mmol) in pyridine (1.5 mL) was added 3,4-dichlorobenzylisocyanate (43 µL, 0.21 mmol). After stirring overnight at room temperature, the crude mixture was purified by Gilson HPLC to afford white solid (50 mg) as a TFA salt at 92% yield. LC/MS (10-99%) M+1/Z 324.2 retention time 2.97 min.

Example 4

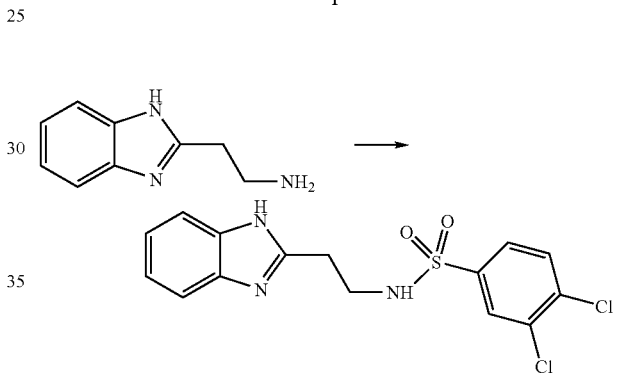

This example teaches the preparation of N-[2-(1H-Benzoimidazol-2-yl)-ethyl]-3,4-dichloro-benzenesulfonamide. To a solution of benzimidazole ethyl amine dihydrochloride (50 mg, 0.21 mmol) in pyridine (1.5 mL) was added 3,4-dichlorobenzylisocyanate (58 µL, 0.21 mmol). After stirring overnight at room temperature, the crude mixture was purified by Gilson HPLC to afford white solid (55 mg) as TFA salt at 92% yield.

Example 5

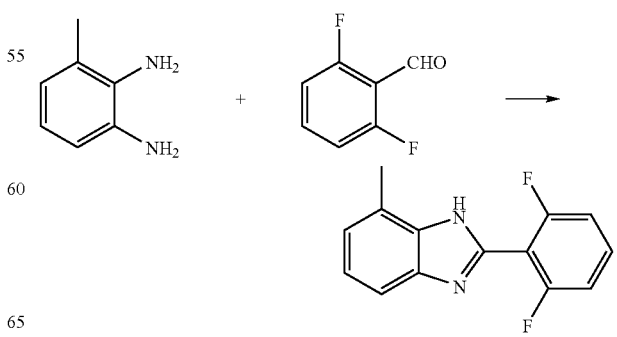

This example teaches the preparation of 2-(2,6-Difluorophenyl)-7-methyl-1H-benzoimidazole according to the following procedure. A solution of 3-methyl-benzene-1,2-diamine (100 mg, 0.82 mmol) and 2,6-difluorobenzaldehyde in EtOH (2 mL) was heated for 5 min at 180° C. in a microwave synthesizer. The EtOH was removed, the residue was dissolved in DMSO (1 mL), and was purified on a Gilson HPLC to afford 2-(2,6-difluoro-phenyl)-7-methyl-1H-benzoimidazole as TFA salt (200 mg) at 100% yield. MUX LC/MS (10-99%) M+1/Z 245.061 retention time 2.1 min.

Other compounds of Formula I have been prepared by methods substantially similar to those described above. The characterization data for these compounds is summarized in Table 3 below. The compound numbers correspond to the compound numbers listed in Table 2.

TABLE 3

Characterization Data for Selected Compounds of Formula I from Table 2

| Cmpd # | LC/MS M+ | LC/RT (min) |
|---|---|---|
| 3 | 256.28 | 3.20 |
| 14 | 336.40 | 2.63 |
| 16 | 326.20 | 1.90 |
| 23 | 324.40 | 3.74 |
| 49 | 326.20 | 2.75 |
| 54 | 344.00 | 2.94 |
| 66 | 372.20 | 2.46 |
| 165 | 324.20 | 1.84 |
| 171 | 364.00 | 2.32 |
| 189 | 324.20 | 1.69 |
| 192 | 324.20 | 2.79 |
| 196 | 358.20 | 2.45 |
| 197 | 332.00 | 2.87 |
| 199 | 321.20 | 1.85 |
| 249 | 309.20 | 2.06 |
| 250 | 314.00 | 2.76 |
| 251 | 313.20 | 1.91 |
| 252 | 329.20 | 1.97 |
| 253 | 309.20 | 1.96 |
| 254 | 363.20 | 2.17 |
| 255 | 364.00 | 2.25 |
| 256 | 365.20 | 2.19 |
| 257 | 379.20 | 2.35 |
| 258 | 364.00 | 2.25 |
| 259 | 339.20 | 2.14 |
| 260 | 372.20 | 2.15 |
| 261 | 372.20 | 2.09 |
| 262 | 386.00 | 2.22 |
| 263 | 372.20 | 2.07 |
| 264 | 346.20 | 2.04 |
| 265 | 338.20 | 3.13 |
| 266 | 344.20 | 3.00 |
| 267 | 323.20 | 2.89 |
| 268 | 370.00 | 2.89 |
| 269 | 336.40 | 2.08 |
| 270 | 344.00 | 3.90 |
| 271 | 346.00 | 3.70 |
| 272 | 340.00 | 3.63 |
| 273 | 324.00 | 3.81 |
| 274 | 325.20 | 3.18 |
| 275 | 366.82 | 3.20 |
| 276 | 346.20 | 3.30 |
| 277 | 315.78 | 3.10 |
| 278 | 267.30 | 3.30 |
| 279 | 346.85 | 3.30 |
| 280 | 335.30 | 3.10 |
| 281 | 326.43 | 3.50 |
| 282 | 284.33 | 3.50 |
| 283 | 323.41 | 3.10 |
| 284 | 317.36 | 3.10 |
| 285 | 321.20 | 1.88 |
| 286 | 339.20 | 1.76 |
| 287 | 354.20 | 2.28 |
| 288 | 353.20 | 1.55 |
| 289 | 366.20 | 2.16 |
| 290 | 350.20 | 2.06 |
| 291 | 382.00 | 2.96 |
| 292 | 372.00 | 2.84 |
| 293 | 372.00 | 3.07 |
| 294 | 332.00 | 2.75 |
| 295 | 338.20 | 2.62 |
| 296 | 348.00 | 2.90 |
| 297 | 373.00 | 2.66 |
| 298 | 384.00 | 2.85 |
| 299 | 400.20 | 3.00 |
| 300 | 384.00 | 2.77 |
| 301 | 413.00 | 3.10 |
| 302 | 358.00 | 3.09 |
| 303 | 356.20 | 2.96 |
| 304 | 400.20 | 2.29 |
| 305 | 352.20 | 1.68 |
| 306 | 398.20 | 2.44 |
| 307 | 380.00 | 2.35 |
| 308 | 320.20 | 2.11 |
| 309 | 398.20 | 1.88 |
| 310 | 321.20 | 1.90 |
| 311 | 332.20 | 2.01 |
| 312 | 338.20 | 1.90 |
| 313 | 380.00 | 2.37 |
| 314 | 388.20 | 2.49 |
| 315 | 386.20 | 2.52 |
| 316 | 422.00 | 2.46 |
| 317 | 381.00 | 2.01 |
| 318 | 386.20 | 2.57 |
| 319 | 388.20 | 2.23 |
| 320 | 381.40 | 1.68 |
| 321 | 388.20 | 2.34 |
| 322 | 386.20 | 2.69 |
| 323 | 408.20 | 2.34 |
| 324 | 328.20 | 2.15 |
| 325 | 401.20 | 2.10 |
| 326 | 372.20 | 2.42 |
| 327 | 400.20 | 2.26 |
| 328 | 398.00 | 2.43 |
| 329 | 347.20 | 1.30 |
| 330 | 338.20 | 1.81 |
| 331 | 347.20 | 1.26 |
| 332 | 381.40 | 1.61 |
| 333 | 353.20 | 1.74 |
| 334 | 335.40 | 1.63 |
| 335 | 335.20 | 1.86 |
| 336 | 383.20 | 1.73 |
| 337 | 374.20 | 1.65 |
| 338 | 339.00 | 1.46 |
| 339 | 408.40 | 1.44 |
| 340 | 347.20 | 1.44 |
| 341 | 381.40 | 1.53 |
| 342 | 415.20 | 2.15 |
| 343 | 364.40 | 1.79 |
| 344 | 388.20 | 2.39 |
| 345 | 362.20 | 2.27 |
| 346 | 342.20 | 2.26 |
| 347 | 421.00 | 2.05 |
| 348 | 350.20 | 2.13 |
| 349 | 376.00 | 2.31 |
| 350 | 382.00 | 2.23 |
| 351 | 404.40 | 2.46 |
| 352 | 376.00 | 2.37 |
| 353 | 406.20 | 2.26 |
| 354 | 404.20 | 2.63 |
| 355 | 328.00 | 2.06 |
| 356 | 342.00 | 1.82 |
| 357 | 344.00 | 1.87 |
| 358 | 350.20 | 2.02 |
| 359 | 350.20 | 1.89 |
| 360 | 350.20 | 1.98 |
| 361 | 368.00 | 1.96 |
| 362 | 366.00 | 1.99 |
| 363 | 350.20 | 2.08 |

TABLE 3-continued

Characterization Data for Selected Compounds of Formula I from Table 2

| Cmpd # | LC/MS M+ | LC/RT (min) |
|---|---|---|
| 366 | 334.00 | 2.54 |
| 367 | 350.20 | 2.75 |
| 368 | 316.20 | 2.45 |
| 369 | 330.20 | 2.68 |
| 370 | 344.00 | 2.83 |

Micromass MUX LCT 4 channel LC/MS, Waters 60 F pump, Gilson 215 4 probe autosampler, Gilson 849 injection module, 1.5 mL/min/column flow rate, 10-99% $CH_3CN$ (0.035% TFA)/$H_2O$ (0.05% TFA) gradient, Phenomenex Luna 5u C18 columns (50 × 4.60 mm), Waters MUX UV-2488 UV detector, Cedex 75 ELSD detectors.

Assays for Detecting and Measuring NaV Inhibition Properties of Compounds

A) Optical Methods for Assaying NaV Inhibition Properties of Compounds:

Compounds of the invention are useful as antagonists of voltage-gated sodium ion channels. Antagonist properties of test compounds were assessed as follows. Cells expressing the NaV of interest were placed into microtiter plates. After an incubation period, the cells were stained with fluorescent dyes sensitive to the transmembrane potential. The test compounds were added to the microtiter plate. The cells were stimulated with either a chemical or electrical means to evoke a NaV dependent membrane potential change from unblocked channels, which was detected and measured with trans-membrane potential-sensitive dyes. Antagonists were detected as a decreased membrane potential response to the stimulus. The optical membrane potential assay utilized voltage-sensitive FRET sensors described by Gonzalez and Tsien (See, Gonzalez, J. E. and R. Y. Tsien (1995) "Voltage sensing by fluorescence resonance energy transfer in single cells" *Biophys J* 69 (4): 1272-80, and Gonzalez, J. E. and R. Y. Tsien (1997) "Improved indicators of cell membrane potential that use fluorescence resonance energy transfer" *Chem Biol* 4 (4): 269-77) in combination with instrumentation for measuring fluorescence changes such as the Voltage/Ion Probe Reader (VIPR®) (See, Gonzalez, J. E., K. Oades, et al. (1999) "Cell-based assays and instrumentation for screening ion-channel targets" *Drug Discov Today* 4 (9): 431-439).

B) VIPR® Optical Membrane Potential Assay Method with Chemical Stimulation Cell Handling and Dye Loading 24 hours before the assay on VIPR, CHO cells endogenously expressing a NaV1.2 type voltage-gated NaV are seeded in 96-well poly-lysine coated plates at 60,000 cells per well. Other subtypes are performed in an analogous mode in a cell line expressing the NaV of interest.

1) On the day of the assay, medium is aspirated and cells are washed twice with 225 μL of Bath Solution #2 (BS #2).
2) A 15 uM CC2-DMPE solution is prepared by mixing 5 mM coumarin stock solution with 10% Pluronic 127 1:1 and then dissolving the mix in the appropriate volume of BS #2.
3) After bath solution is removed from the 96-well plates, the cells are loaded with 80 μL of the CC2-DMPE solution. Plates are incubated in the dark for 30 minutes at room temperature.
4) While the cells are being stained with coumarin, a 15 μL oxonol solution in BS #2 is prepared. In addition to DiSBAC$_2$(3), this solution should contain 0.75 mM ABSC1 and 30 μL veratridine (prepared from 10 mM EtOH stock, Sigma #V-5754).
5) After 30 minutes, CC2-DMPE is removed and the cells are washed twice with 225 μL of BS #2. As before, the residual volume should be 40 μL.
6) Upon removing the bath, the cells are loaded with 80 μL of the DiSBAC$_2$(3) solution, after which test compound, dissolved in DMSO, is added to achieve the desired test concentration to each well from the drug addition plate and mixed thoroughly. The volume in the well should be roughly 121 μL. The cells are then incubated for 20-30 minutes.
7) Once the incubation is complete, the cells are ready to be assayed on VIPR® with a sodium addback protocol. 120 μL of Bath solution #1 is added to stimulate the NaV dependent depolarization. 200 μL tetracaine was used as an antagonist positive control for block of the NaV channel.

Analysis of VIPR® Data:

Data are analyzed and reported as normalized ratios of background-subtracted emission intensities measured in the 460 nm and 580 nm channels. Background intensities are then subtracted from each assay channel. Background intensities are obtained by measuring the emission intensities during the same time periods from identically treated assay wells in which there are no cells. The response as a function of time is then reported as the ratios obtained using the following formula:

$$R(t) = \frac{(intensity_{460\ nm} - background_{460\ nm})}{(intensity_{580\ nm} - background_{580\ nm})}$$

The data is further reduced by calculating the initial ($R_i$) and final ($R_f$) ratios. These are the average ratio values during part or all of the pre-stimulation period, and during sample points during the stimulation period. The response to the stimulus $R=R_f/R_i$ is then calculated. For the $Na^+$ addback analysis time windows, baseline is 2-7 sec and final response is sampled at 15-24 sec.

Control responses are obtained by performing assays in the presence of a compound with the desired properties (positive control), such as tetracaine, and in the absence of pharmacological agents (negative control). Responses to the negative (N) and positive (P) controls are calculated as above. The compound antagonist activity A is defined as:

$$A = \frac{R - P}{N - P} * 100.$$

where R is the ratio response of the test compound

| Solutions [mM] | |
|---|---|
| Bath Solution #1: | NaCl 160, KCl 4.5, CaCl$_2$ 2, MgCl$_2$ 1, HEPES 10, pH 7.4 with NaOH |
| Bath Solution #2 | TMA-Cl 160, CaCl$_2$ 0.1, MgCl$_2$ 1, HEPES 10, pH 7.4 with KOH (final K concentration~5 mM) |
| CC2-DMPE: | prepared as a 5 mM stock solution in DMSO and stored at −20° C. |
| DiSBAC$_2$(3): | prepared as a 12 mM stock in DMSO and stored at −20° C. |
| ABSC1: | prepared as a 200 mM stock in distilled H$_2$O and stored at room temperature |

Cell Culture

CHO cells are grown in DMEM (Dulbecco's Modified Eagle Medium; GibcoBRL #10569-010) supplemented with 10% FBS (Fetal Bovine Serum, qualified; GibcoBRL #16140-071) and 1% Pen-Strep (Penicillin-Streptomycin; GibcoBRL #15140-122). Cells are grown in vented cap flasks, in 90% humidity and 10% $CO_2$, to 100% confluence. They are usually split by trypsinization 1:10 or 1:20, depending on scheduling needs, and grown for 2-3 days before the next split.

C) VIPR® Optical Membrane Potential Assay Method with Electrical Stimulation

The following is an example of how NaV1.3 inhibition activity is measured using the optical membrane potential method #2. Other subtypes are performed in an analogous mode in a cell line expressing the NaV of interest.

HEK293 cells stably expressing NaV1.3 are plated into 96-well microtiter plates. After an appropriate incubation period, the cells are stained with the voltage sensitive dyes CC2-DMPE/DiSBAC2(3) as follows.

Reagents:

100 mg/mL Pluronic F-127 (Sigma #P2443), in dry DMSO 10 mM $DiSBAC_2(3)$ (Aurora #00-100-010) in dry DMSO 10 mM CC2-DMPE (Aurora #00-100-008) in dry DMSO 200 mM ABSC1 in $H_2O$ Hank's Balanced Salt Solution (Hyclone #SH30268.02) supplemented with 10 mM HEPES (Gibco #15630-080)

Loading Protocol:

2×CC2-DMPE=20 µM CC2-DMPE: 10 mM CC2-DMPE is vortexed with an equivalent volume of 10% pluronic, followed by vortexing in required amount of HBSS containing 10 mM HEPES. Each cell plate will require 5 mL of 2×CC2-DMPE. 50 µL of 2×CC2-DMPE is to wells containing washed cells, resulting in a 10 µM final staining concentration. The cells are stained for 30 minutes in the dark at RT.

2×$DISBAC_2(3)$ with ABSC1=6 µM $DISBAC_2(3)$ and 1 mM ABSC1: The required amount of 10 mM $DISBAC_2(3)$ is added to a 50 ml conical tube and mixed with 1 µL 10% pluronic for each mL of solution to be made and vortexed together. Then HBSS/HEPES is added to make up 2× solution. Finally, the ABSC1 is added.

The 2×$DiSBAC_2(3)$ solution can be used to solvate compound plates. Note that compound plates are made at 2× drug concentration. Wash stained plate again, leaving residual volume of 50 µL. Add 50 uL/well of the 2×$DiSBAC_2(3)$ w/ ABSC1. Stain for 30 minutes in the dark at RT.

The electrical stimulation instrument and methods of use are described in ION Channel Assay Methods PCT/US01/21652, herein incorporated by reference. The instrument comprises a microtiter plate handler, an optical system for exciting the coumarin dye while simultaneously recording the coumarin and oxonol emissions, a waveform generator, a current- or voltage-controlled amplifier, and a device for inserting electrodes in well. Under integrated computer control, this instrument passes user-programmed electrical stimulus protocols to cells within the wells of the microtiter plate.

Reagents

Assay Buffer #1

140 mM NaCl, 4.5 mM KCl, 2 mM $CaCl_2$, 1 mM $MgCl_2$, 10 mM HEPES, 10 mM glucose, pH 7.40, 330 mOsm Pluronic stock (1100×): 100 mg/mL pluronic 127 in dry DMSO Oxonol stock (3333×): 10 mM $DiSBAC_2(3)$ in dry DMSO Coumarin stock (1000×): 10 mM CC2-DMPE in dry DMSO ABSC1 stock (400×): 200 mM ABSC1 in water Assay Protocol
1. Insert or use electrodes into each well to be assayed.
2. Use the current-controlled amplifier to deliver stimulation wave pulses for 3 s. Two seconds of pre-stimulus recording are performed to obtain the un-stimulated intensities. Five seconds of post-stimulation recording are performed to examine the relaxation to the resting state.

Data Analysis

Data are analyzed and reported as normalized ratios of background-subtracted emission intensities measured in the 460 nm and 580 nm channels. Background intensities are then subtracted from each assay channel. Background intensities are obtained by measuring the emission intensities during the same time periods from identically treated assay wells in which there are no cells. The response as a function of time is then reported as the ratios obtained using the following formula:

$$R(t) = \frac{(intensity_{460\ nm} - background_{460\ nm})}{(intensity_{580\ nm} - background_{580\ nm})}$$

The data is further reduced by calculating the initial ($R_i$) and final ($R_f$) ratios. These are the average ratio values during part or all of the pre-stimulation period, and during sample points during the stimulation period. The response to the stimulus $R=R_f/R_i$ is then calculated.

Control responses are obtained by performing assays in the presence of a compound with the desired properties (positive control), such as tetracaine, and in the absence of pharmacological agents (negative control). Responses to the negative (N) and positive (P) controls are calculated as above. The compound antagonist activity A is defined as:

$$A = \frac{R-P}{N-P} * 100.$$

where R is the ratio response of the test compound.

Electrophysiology Assays for NaV Activity and Inhibition of Test Compounds

Patch clamp electrophysiology was used to assess the efficacy and selectivity of sodium channel blockers in dorsal root ganglion neurons. Rat neurons were isolated from the dorsal root ganglions and maintained in culture for 2 to 10 days in the presence of NGF (50 ng/ml) (culture media consisted of NeurobasalA supplemented with B27, glutamine and antibiotics). Small diameter neurons (nociceptors, 8-12 µm in diameter) have been visually identified and probed with fine tip glass electrodes connected to an amplifier (Axon Instruments). The "voltage clamp" mode has been used to assess the compound's IC50 holding the cells at −60 mV. In addition, the "current clamp" mode has been employed to test the efficacy of the compounds in blocking action potential generation in response to current injections. The results of these experiments have contributed to the definition of the efficacy profile of the compounds.

VOLTAGE-CLAMP Assay in DRG Neurons

TTX-resistant sodium currents were recorded from DRG somata using the whole-cell variation of the patch clamp technique. Recordings were made at room temperature (~22° C.) with thick walled borosilicate glass electrodes (WPI; resistance 3-4 MΩ) using an Axopatch 200B amplifier (Axon Instruments). After establishing the whole-cell configuration, approximately 15 minutes were allowed for the pipette solution to equilibrate within the cell before beginning recording. Currents were lowpass filtered between 2-5 kHz and digitally sampled at 10 kHz. Series resistance was compensated 60-70% and was monitored continuously throughout the experiment. The liquid junction potential (−7 mV) between the intracellular pipette solution and the external recording solution was not accounted for in the data analysis. Test solutions were applied to the cells with a gravity driven fast perfusion system (SF-77; Warner Instruments).

Dose-response relationships were determined in voltage clamp mode by repeatedly depolarizing the cell from the experiment specific holding potential to a test potential of +10 mV once every 60 seconds. Blocking effects were allowed to plateau before proceeding to the next test concentration.

Solutions

Intracellular solution (in mM): Cs—F (130), NaCl (10), $MgCl_2$ (1), EGTA (1.5), $CaCl_2$ (0.1), HEPES (10), glucose (2), pH=7.42, 290 mOsm.

Extracellular solution (in mM): NaCl (138), $CaCl_2$ (1.26), KCl (5.33), $KH_2PO_4$ (0.44), $MgCl_2$ (0.5), $MgSO_4$ (0.41), $NaHCO_3$ (4), $Na_2HPO_4$ (0.3), glucose (5.6), HEPES (10), CdCl2 (0.4), NiCl2 (0.1), TTX ($0.25 \times 10^{-3}$).

CURRENT-CLAMP Assay for NaV Channel Inhibition Activity of Compounds

Cells were current-clamped in whole-cell configuration with a Multiplamp 700A amplifier (Axon Inst). Borosilicate pipettes (4-5 MOhm) were filled with (in mM):150 K-gluconate, 10 NaCl, 0.1 EGTA, 10 Hepes, 2 $MgCl_2$, (buffered to pH 7.34 with KOH). Cells were bathed in (in mM): 140 NaCl, 3 KCl, 1 MgCl, 1 CaCl, and 10 Hepes). Pipette potential was zeroed before seal formation; liquid junction potentials were not corrected during acquisition. Recordings were made at room temperature.

Assays for Detecting and Measuring CaV Inhibition Properties of Compounds

A) Optical Methods for Assaying CaV Inhibition Properties of Compounds:

Compounds of the invention are useful as antagonists of voltage-gated calcium ion channels. Antagonist properties of test compounds were assessed as follows. Cells expressing the CaV of interest were placed into microtiter plates. After an incubation period, the cells were stained with fluorescent dyes sensitive to the transmembrane potential. The test compounds were added to the microtiter plate. The cells were stimulated with electrical means to evoke a CaV dependent membrane potential change from unblocked channels, which was detected and measured with trans-membrane potential-sensitive dyes. Antagonists were detected as a decreased membrane potential response to the stimulus. The optical membrane potential assay utilized voltage-sensitive FRET sensors described by Gonzalez and Tsien (See, Gonzalez, J. E. and R. Y. Tsien (1995) "Voltage sensing by fluorescence resonance energy transfer in single cells" *Biophys J* 69 (4): 1272-80, and Gonzalez, J. E. and R. Y. Tsien (1997) "Improved indicators of cell membrane potential that use fluorescence resonance energy transfer" *Chem Biol* 4 (4): 269-77) in combination with instrumentation for measuring fluorescence changes such as the Voltage/Ion Probe Reader (VIPR®) (See, Gonzalez, J. E., K. Oades, et al. (1999) "Cell-based assays and instrumentation for screening ion-channel targets" *Drug Discov Today* 4 (9): 431-439).

VIPR® Optical Membrane Potential Assay Method with Electrical Stimulation

The following is an example of how CaV2.2 inhibition activity is measured using the optical membrane potential method. Other subtypes are performed in an analogous mode in a cell line expressing the CaV of interest.

HEK293 cells stably expressing CaV2.2 are plated into 96-well microtiter plates. After an appropriate incubation period, the cells are stained with the voltage sensitive dyes CC2-DMPE/DiSBAC2(3) as follows.

Reagents:

100 mg/mL Pluronic F-127 (Sigma #P2443), in dry DMSO 10 mM $DiSBAC_6(3)$ (Aurora #00-100-010) in dry DMSO 10 mM CC2-DMPE (Aurora #00-100-008) in dry DMSO 200 mM Acid Yellow 17 (Aurora #VABSC) in $H_2O$ 370 mM Barium Chloride (Sigma Cat# B6394) in $H_2O$ Bath X 160 mM NaCl (Sigma Cat# S-9888)

4.5 mM KCl (Sigma Cat# P-5405)

1 mM MgCl2 (Fluka Cat# 63064)

10 mM HEPES (Sigma Cat# H-4034)

pH 7.4 using NaOH

Loading Protocol:

2×CC2-DMPE=20 µM CC2-DMPE: 10 mM CC2-DMPE is vortexed with an equivalent volume of 10% pluronic, followed by vortexing in required amount of HBSS containing 10 mM HEPES. Each cell plate will require 5 mL of 2×CC2-DMPE. 50 µL of 2×CC2-DMPE is added to wells containing washed cells, resulting in a 10 µM final staining concentration. The cells are stained for 30 minutes in the dark at RT.

2×CC2DMPE & $DISBAC_6(3)$=8 µM CC2DMPE & 2.5 µM $DISBAC_6(3)$: Vortex together both dyes with an equivalent volume of 10% pluronic (in DMSO). Vortex in required amount of Bath X with beta-cyclodextrin. Each 96 well cell plate will require 5 ml of 2×CC2DMPE. Wash plate with ELx405 with Bath X, leaving a residual volume of 50 µL/well. Add 50 µL of 2×CC2DMPE & $DISBAC_6(3)$ to each well. Stain for 30 minutes in the dark at RT.

1.5×AY17=750 µM AY17 with 15 mM $BaCl_2$: Add Acid Yellow 17 to vessel containing Bath X. Mix well. Allow solution to sit for 10 minutes. Slowly mix in 370 mM $BaCl_2$. This solution can be used to solvate compound plates. Note that compound plates are made at 1.5× drug concentration and not the usual 2×. Wash CC2 stained plate, again, leaving residual volume of 50 µL. Add 100 uL/well of the AY17 solution. Stain for 15 minutes in the dark at RT. Run plate on the optical reader.

The electrical stimulation instrument and methods of use are described in ION Channel Assay Methods PCT/US01/21652, herein incorporated by reference. The instrument comprises a microtiter plate handler, an optical system for exciting the coumarin dye while simultaneously recording the coumarin and oxonol emissions, a waveform generator, a current- or voltage-controlled amplifier, and a device for inserting electrodes in well. Under integrated computer control, this instrument passes user-programmed electrical stimulus protocols to cells within the wells of the microtiter plate.

Assay Protocol

Insert or use electrodes into each well to be assayed.

Use the current-controlled amplifier to deliver stimulation wave pulses for 3-5 s. Two seconds of pre-stimulus recording are performed to obtain the un-stimulated intensities. Five seconds of post-stimulation recording are performed to examine the relaxation to the resting state.

Data Analysis

Data are analyzed and reported as normalized ratios of background-subtracted emission intensities measured in the 460 nm and 580 nm channels. Background intensities are then subtracted from each assay channel. Background intensities are obtained by measuring the emission intensities during the same time periods from identically treated assay wells in which there are no cells. The response as a function of time is then reported as the ratios obtained using the following formula:

$$R(t) = \frac{(intensity_{460\ nm} - background_{460\ nm})}{(intensity_{580\ nm} - background_{580\ nm})}$$

The data is further reduced by calculating the initial ($R_i$) and final ($R_f$) ratios. These are the average ratio values during part or all of the pre-stimulation period, and during sample points during the stimulation period. The response to the stimulus $R=R_f/R_i$ is then calculated.

Control responses are obtained by performing assays in the presence of a compound with the desired properties (positive control), such as mibefradil, and in the absence of pharmacological agents (negative control). Responses to the negative (N) and positive (P) controls are calculated as above. The compound antagonist activity A is defined as:

$$A = \frac{R-P}{N-P} * 100.$$

where R is the ratio response of the test compound.

Electrophysiology Assays for CaV Activity and Inhibition of Test Compounds

Patch clamp electrophysiology was used to assess the efficacy of calcium channel blockers expressed in HEK293 cells. HEK293 cells expressing CaV2.2 have been visually identified and probed with fine tip glass electrodes connected to an amplifier (Axon Instruments). The "voltage clamp" mode has been used to assess the compound's IC50 holding the cells at −100 mV. The results of these experiments have contributed to the definition of the efficacy profile of the compounds.

VOLTAGE-CLAMP Assay in HEK293 Cells Expressing CaV2.2

CaV2.2 calcium currents were recorded from HEK293 cells using the whole-cell variation of the patch clamp technique. Recordings were made at room temperature (~22° C.) with thick walled borosilicate glass electrodes (WPI; resistance 3-4 MΩ) using an Axopatch 200B amplifier (Axon Instruments). After establishing the whole-cell configuration, approximately 15 minutes were allowed for the pipette solution to equilibrate within the cell before beginning recording. Currents were lowpass filtered between 2-5 kHz and digitally sampled at 10 kHz. Series resistance was compensated 60-70% and was monitored continuously throughout the experiment. The liquid junction potential (−7 mV) between the intracellular pipette solution and the external recording solution was not accounted for in the data analysis. Test solutions were applied to the cells with a gravity driven fast perfusion system (SF-77; Warner Instruments).

Dose-response relationships were determined in voltage clamp mode by repeatedly depolarizing the cell from the experiment specific holding potential to a test potential of +20 mV for 50 ms at frequencies of 0.1, 1, 5, 10, 15, and 20 Hz. Blocking effects were allowed to plateau before proceeding to the next test concentration.

Solutions

Intracellular solution (in mM): Cs—F (130), NaCl (10), MgCl$_2$ (1), EGTA (1.5), CaCl$_2$ (0.1), HEPES (10), glucose (2), pH=7.42, 290 mOsm.

Extracellular solution (in mM): NaCl (138), BaCl$_2$ (10), KCl (5.33), KH$_2$PO$_4$ (0.44), MgCl$_2$ (0.5), MgSO$_4$ (0.41), NaHCO$_3$ (4), Na$_2$HPO$_4$ (0.3), glucose (5.6), HEPES (10).

Following these procedures, representative compounds of the present invention were found to possess desired N-type calcium channel modulation activity.

Compounds of the invention as shown in Table 2 were found modulate voltage-gated sodium channels at 25.0 μM or less.

In order that the invention described herein may be more fully understood, the following examples are set forth. It should be understood that these examples are for illustrative purposes only and are not to be construed as limiting this invention in any manner.

We claim:

1. A method of treating or lessening the severity of a disease, disorder, or condition selected from acute, chronic, neuropathic, or inflammatory pain comprising the step of administering to a patient an effective amount of a compound of Formula I:

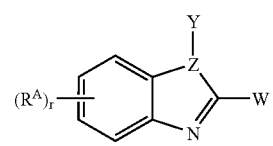

or a pharmaceutically acceptable salt thereof, wherein:
r is 0;
Z is N;
Y is hydrogen;
W is Formula Ia:

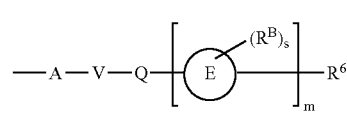

wherein:
A is -T-NH—,
wherein:
T is —CH$_2$CH$_2$—;
V is —C(O)—;
Q is —CH$_2$O—;
m is 1;
Ring E is phenyl;
s is 0 to 1;

each occurrence of R is independently selected from hydrogen or an optionally substituted $C_{1-6}$ aliphatic group; and $R^B$ is selected from J wherein:

J is halo, CN, $NO_2$, $CF_3$, $OCF_3$, OH, $SR^6$, $S(O)R^6$, $SO_2R^6$, $NH_2$, $NHR^6$, $N(R^6)_2$, $NR^6R^8$, C(O)OH, C(O)$OR^6$ or $OR^6$; or:

two J on adjacent ring atoms, taken together, form 1,2-methylenedioxy or 1,2-ethylenedioxy;

$R^6$ is hydrogen or a $C_{1-6}$aliphatic group substituted with $R^7$, wherein:

$R^7$ is a $C_{3-8}$cycloaliphatic, $C_{6-10}$ aryl, a 5-10 membered heteroaryl ring having 1-4 heteroatoms independently selected from nitrogen, oxygen, or sulfur, or a 3-10 membered heterocyclyl ring having 1-4 heteroatoms independently selected from nitrogen, oxygen, or sulfur, wherein $R^7$ is optionally substituted with up to two substituents independently selected from R, 1,2-methylenedioxy, 1,2-ethylenedioxy, or $(CH_2)_n$-G, wherein n is 0 or 1; and wherein G is selected from halo, CN, $NO_2$, $CF_3$, $OCF_3$, OH, S-aliphatic, S(O)-aliphatic, $SO_2$-aliphatic, $NH_2$, N-aliphatic, N(aliphatic)$_2$, N(aliphatic)$R^8$, COOH, C(O)O(-aliphatic, or O-aliphatic; and $R^8$ is an amino protecting group.

2. The method according to claim 1, wherein the disease, condition, or disorder is femur cancer pain; non-malignant chronic bone pain; rheumatoid arthritis; osteoarthritis; spinal stenosis; neuropathic low back pain; neuropathic low back pain; myofascial pain syndrome; fibromyalgia; temporomandibular joint pain; chronic visceral pain, including, abdominal; pancreatic; IBS pain; chronic headache pain; migraine; tension headache, including, cluster headaches; chronic neuropathic pain, including, post-herpetic neuralgia; diabetic neuropathy; HIV-associated neuropathy; trigeminal neuralgia; Charcot-Marie Tooth neuropathy; hereditary sensory neuropathies; peripheral nerve injury; painful neuromas; ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome; phantom pain; intractable pain; acute pain, acute post-operative pain; acute musculoskeletal pain; joint pain; mechanical low back pain; neck pain; tendonitis; injury/exercise pain; acute visceral pain, including, abdominal pain; pyelonephritis; appendicitis; cholecystitis; intestinal obstruction; hernias; etc; chest pain, including, cardiac pain; pelvic pain, renal colic pain, acute obstetric pain, including, labor pain; cesarean section pain; acute inflammatory, burn and trauma pain; acute intermittent pain, including, endometriosis; acute herpes zoster pain; sickle cell anemia; acute pancreatitis; breakthrough pain; orofacial pain, including, sinusitis pain, dental pain; multiple sclerosis (MS) pain; pain in depression; leprosy pain; Behcet's disease pain; adiposis dolorosa; phlebitic pain; Guillain-Barre pain; painful legs and moving toes; Haglund syndrome; erythromelalgia pain; Fabry's disease pain; interstitial cyctitis (IC); or prostatitis; arthritis, migraine cluster headaches, trigeminal neuralgia, herpetic neuralgia or general neuralgias.

3. The method according to claim 1, wherein each $R^B$ is independently $OR^6$, $N(R^6)_2$, halo, or $NO_2$.

4. The method according to claim 1, wherein said compound is of formula IIa:

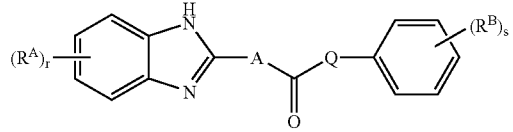

or a pharmaceutically acceptable salt thereof.

5. The method according to claim 4, wherein:
A is —$CH_2CH_2NH$—;
Q is —$CH_2O$—; and
each $R^B$ is independently halogen.

6. The method according to claim 4, wherein:
A is —$CH_2CH_2NH$—;
Q is —$CH_2O$—; and
each $R^B$ is independently CN, —$N(R^6)_2$, or halogen.

7. The method according to claim 4, wherein:
A is —$CH_2CH_2NH$—;
Q is —$CH_2O$—; and
each $R^B$ is independently —$N(R^6)_2$, or halogen.

8. The method according to claim 4, wherein:
A is —$CH_2CH_2NH$—;
Q is —$CH_2O$—; and
each $R^B$ is independently —$OR^6$, or halogen.

9. The method according to claim 4, wherein:
A is —$CH_2CH_2NH$—;
Q is —$CH_2O$—; and
each $R^B$ is independently fluoro, or chloro.

10. The method according to claim 4, wherein:
A is —$CH_2CH_2NH$—;
Q is —$CH_2O$—; and
each $R^B$ is independently bromo, or chloro.

11. The method according to claim 1, wherein said method comprises the step of administering to said patient an effective amount of a compound selected from any one of the following:

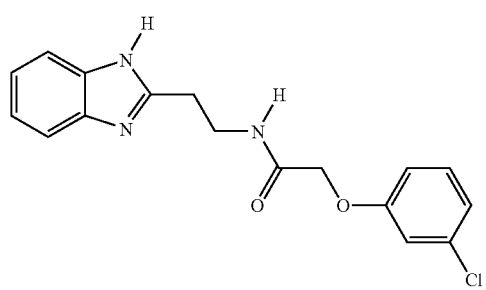

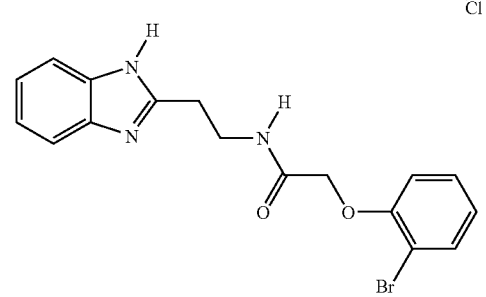

-continued
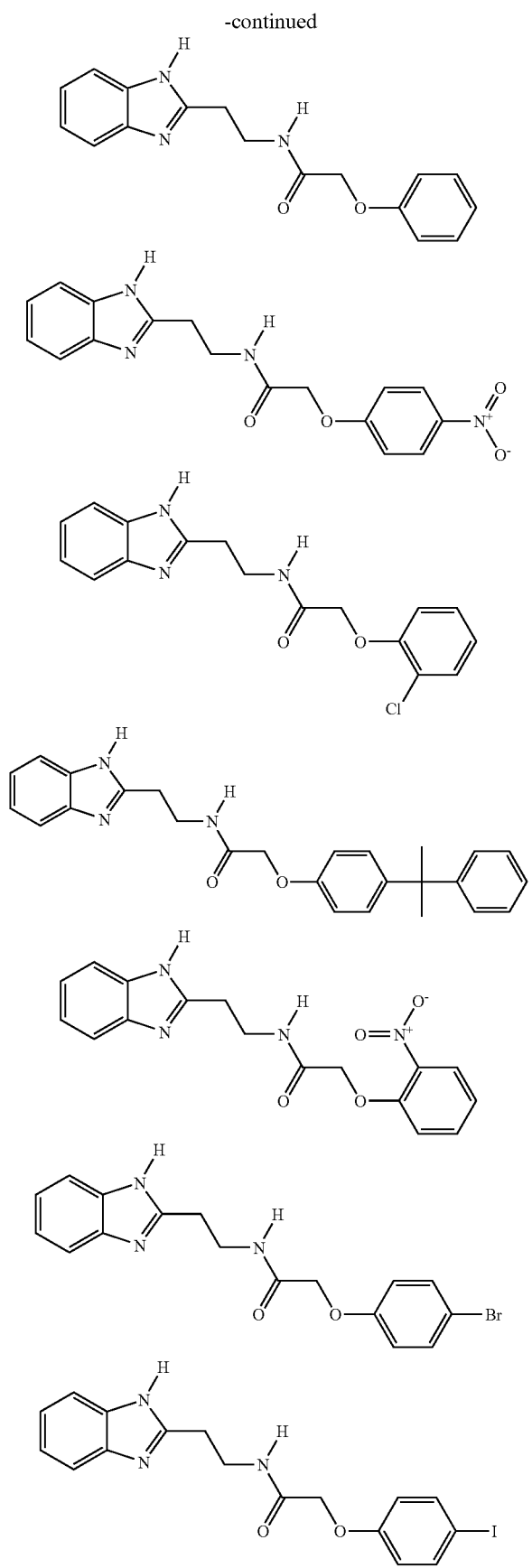
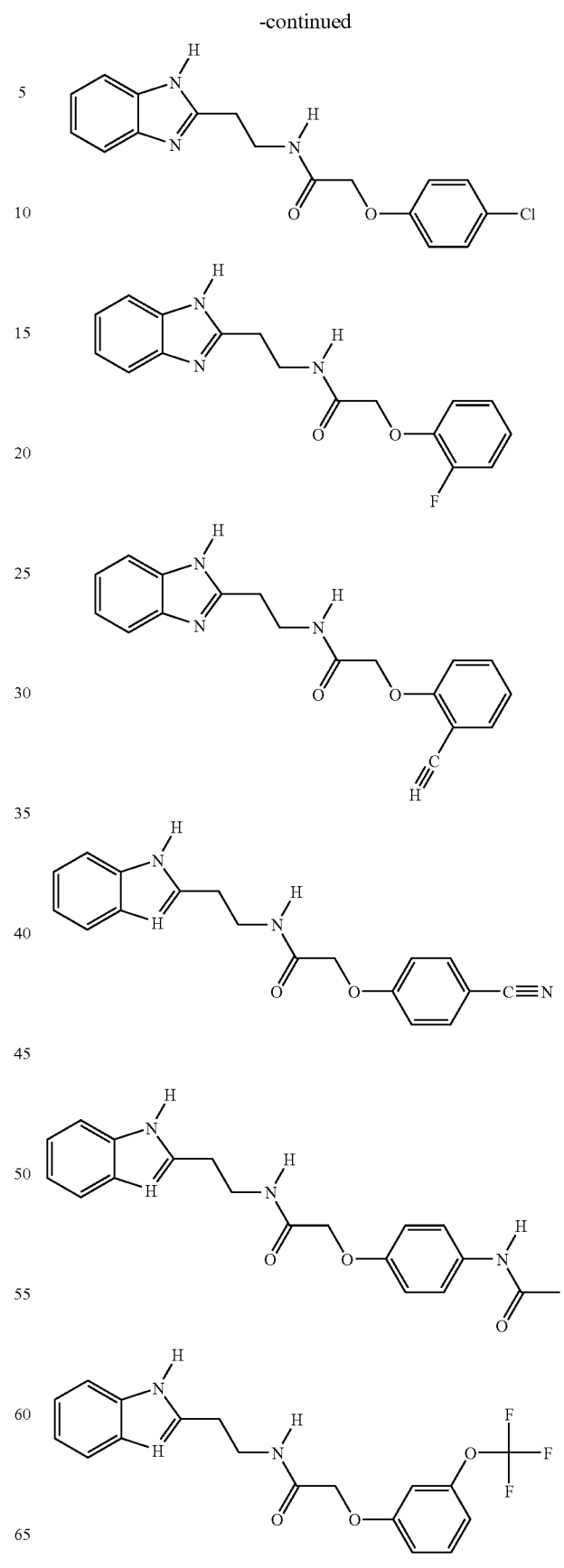

-continued

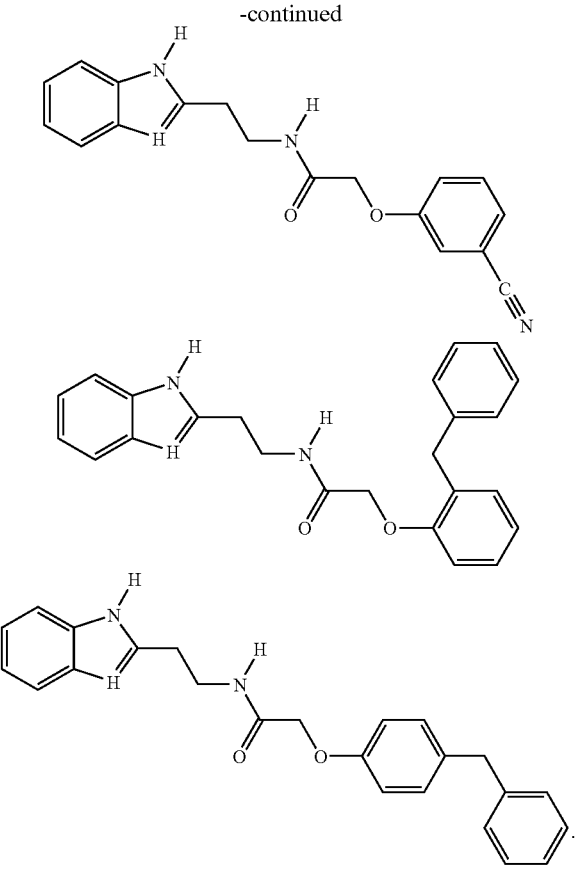

12. A method of inhibiting NaV1.2, NaV1.3, NaV1.4, NaV1.5, NaV1.7, or NaV1.8 activity in a biological sample which method comprises contacting said biological sample with a compound of Formula I:

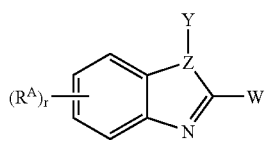

or a pharmaceutically acceptable salt thereof, wherein:
r is 0;
Z is N;
Y is hydrogen;
W is Formula Ia:

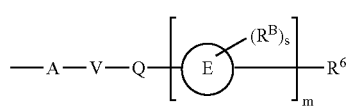

wherein:
A is -T-NH—,
wherein:
T is —$CH_2CH_2$—;
V is —C(O)—;
Q is —$CH_2O$—;
m is 1;
Ring E is phenyl;
s is 0 to 1;
each occurrence of R is independently selected from hydrogen or an optionally substituted $C_{1-6}$ aliphatic group; and
$R^B$ is selected from J wherein:
J is halo, CN, $NO_2$, $CF_3$, $OCF_3$, OH, $SR^6$, $S(O)R^6$, $SO_2R^6$, $NH_2$, $NHR^6$, $N(R^6)_2$, $NR^6R^8$, C(O)OH, C(O)$OR^6$ or $OR^6$; or:
two J on adjacent ring atoms, taken together, form 1,2-methylenedioxy or 1,2-ethylenedioxy;
$R^6$ is hydrogen or a $C_{1-6}$aliphatic group substituted with $R^7$, wherein:
$R^7$ is a $C_{3-8}$cycloaliphatic, $C_{6-10}$ aryl, a 5-10 membered heteroaryl ring having 1-4 heteroatoms independently selected from nitrogen, oxygen, or sulfur, or a 3-10 membered heterocyclyl ring having 1-4 heteroatoms independently selected from nitrogen, oxygen, or sulfur, wherein $R^7$ is optionally substituted with up to two substituents independently selected from R, 1,2-methylenedioxy, 1,2-ethylenedioxy, or $(CH_2)_n$-G, wherein n is 0 or 1; and wherein G is selected from halo, CN, $NO_2$, $CF_3$, $OCF_3$, OH, S-aliphatic, S(O)-aliphatic, $SO_2$-aliphatic, $NH_2$, N-aliphatic, N(aliphatic)$_2$, N(aliphatic)$R^8$, COOH, C(O)O(-aliphatic, or O-aliphatic; and
$R^8$ is an amino protecting group.

13. A method of inhibiting NaV1.2, NaV1.3, NaV1.4, NaV1.5, NaV1.7, or NaV1.8 activity in a patient to treat or lessen the severity of a disease, disorder or condition in said patient wherein said disease, disorder or condition is selected from acute, chronic, neuropathic or inflammatory pain, and wherein said method comprises administering to said patient a compound of Formula I:

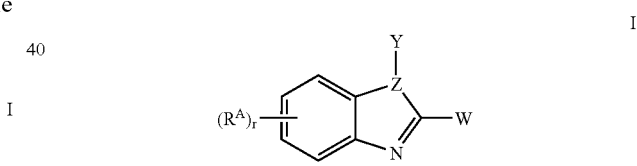

or a pharmaceutically acceptable salt thereof, wherein:
r is 0;
Z is N;
Y is hydrogen;
W is Formula Ia:

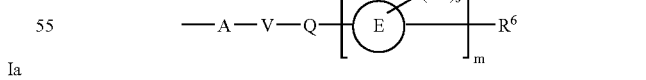

wherein:
A is -T-NH—,
wherein:
T is —$CH_2CH_2$—;
V is —C(O)—;
Q is —$CH_2O$—;
m is 1;
Ring E is phenyl;
s is 0 to 1;

each occurrence of R is independently selected from hydrogen or an optionally substituted $C_{1-6}$ aliphatic group; and $R^B$ is selected from J wherein:

J is halo, CN, $NO_2$, $CF_3$, $OCF_3$, OH, $SR^6$, $S(O)R^6$, $SO_2R^6$, $NH_2$, $NHR^6$, $N(R^6)_2$, $NR^6R^8$, C(O)OH, C(O)$OR^6$ or $OR^6$; or:

two J on adjacent ring atoms, taken together, form 1,2-methylenedioxy or 1,2-ethylenedioxy;

$R^6$ is hydrogen or a $C_{1-6}$ aliphatic group substituted with $R^7$, wherein:

$R^7$ is a $C_{3-8}$ cycloaliphatic, $C_{6-10}$ aryl, a 5-10 membered heteroaryl ring having 1-4 heteroatoms independently selected from nitrogen, oxygen, or sulfur, or a 3-10 membered heterocyclyl ring having 1-4 heteroatoms independently selected from nitrogen, oxygen, or sulfur, wherein $R^7$ is optionally substituted with up to two substituents independently selected from R, 1,2-methylenedioxy, 1,2-ethylenedioxy, or $(CH_2)_n$-G, wherein n is 0 or 1; and wherein G is selected from halo, CN, $NO_2$, $CF_3$, $OCF_3$, OH, S-aliphatic, S(O)-aliphatic, $SO_2$-aliphatic, $NH_2$, N-aliphatic, N(aliphatic)$_2$, N(aliphatic)$R^8$, COOH, C(O)O(-aliphatic, or O-aliphatic; and $R^8$ is an amino protecting group.

14. The method according to claim 13, wherein $R^B$ is $OR^6$, $N(R^6)_2$, halo, or $NO_2$.

15. The method according to claim 13, wherein said compound is of formula IIa:

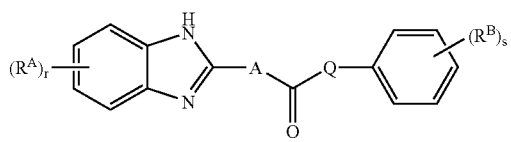

IIa or a pharmaceutically acceptable salt thereof.

16. The method according to claim 15, wherein:
A is —$CH_2CH_2NH$—;
Q is —$CH_2O$—; and
$R^B$ is CN, —$N(R^6)_2$, —$OR^6$ or halogen.

17. The method according to claim 16, wherein:
$R^B$ is —$N(R^6)_2$, or halogen.

18. The method according to claim 17, wherein:
$R^B$ is fluoro, chloro or bromo.

19. The method according to claim 18, wherein:
$R^B$ is bromo or chloro.

20. The method according to claim 13, wherein said method comprises administering to said patient a compound selected from any one of the following:

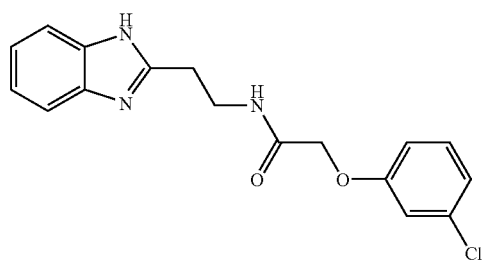

-continued

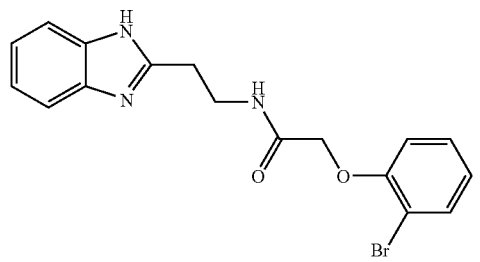

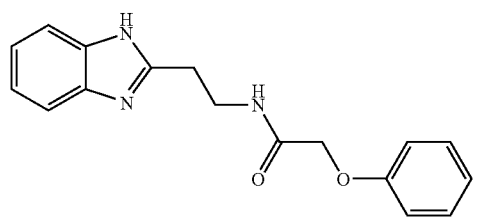

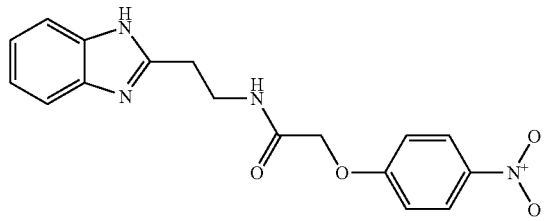

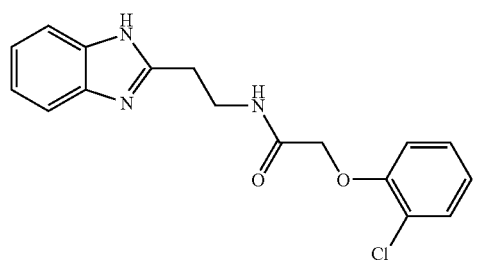

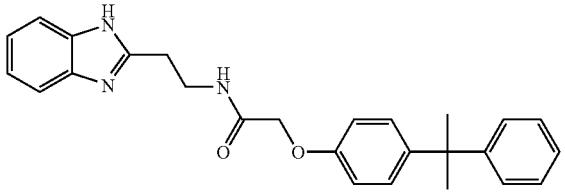

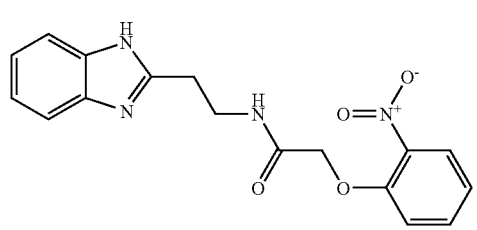

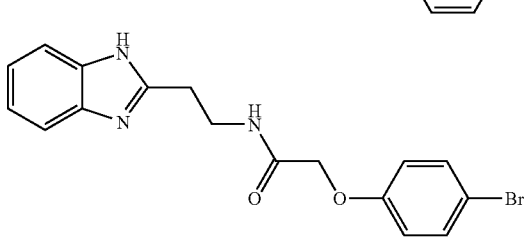

-continued
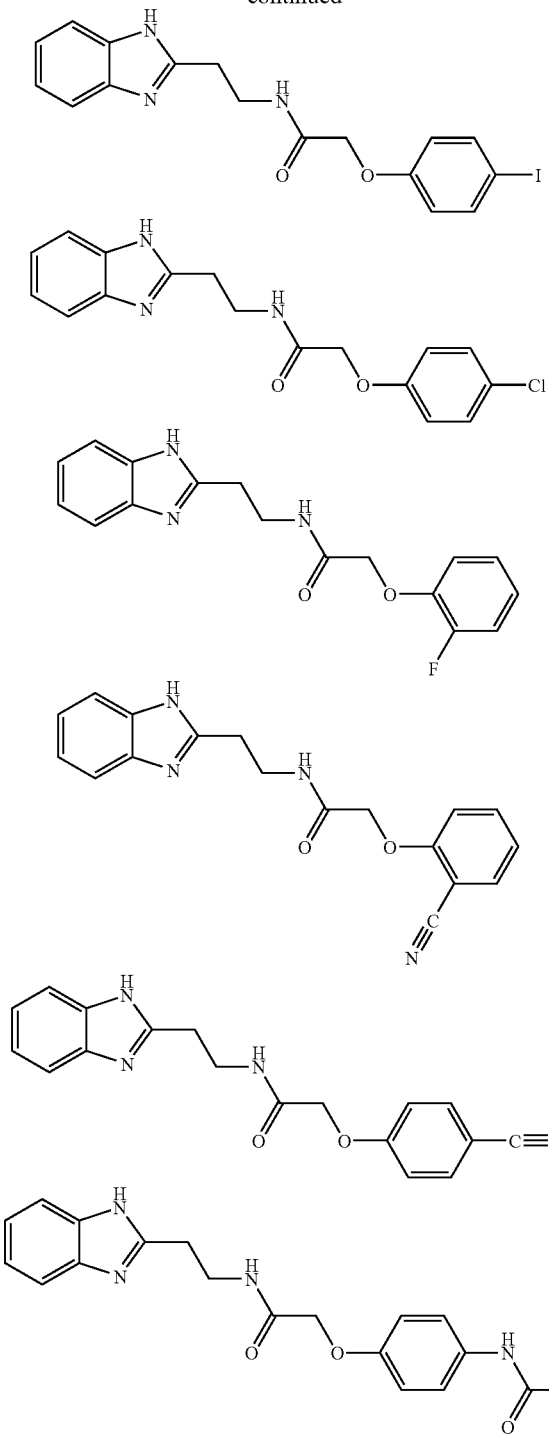
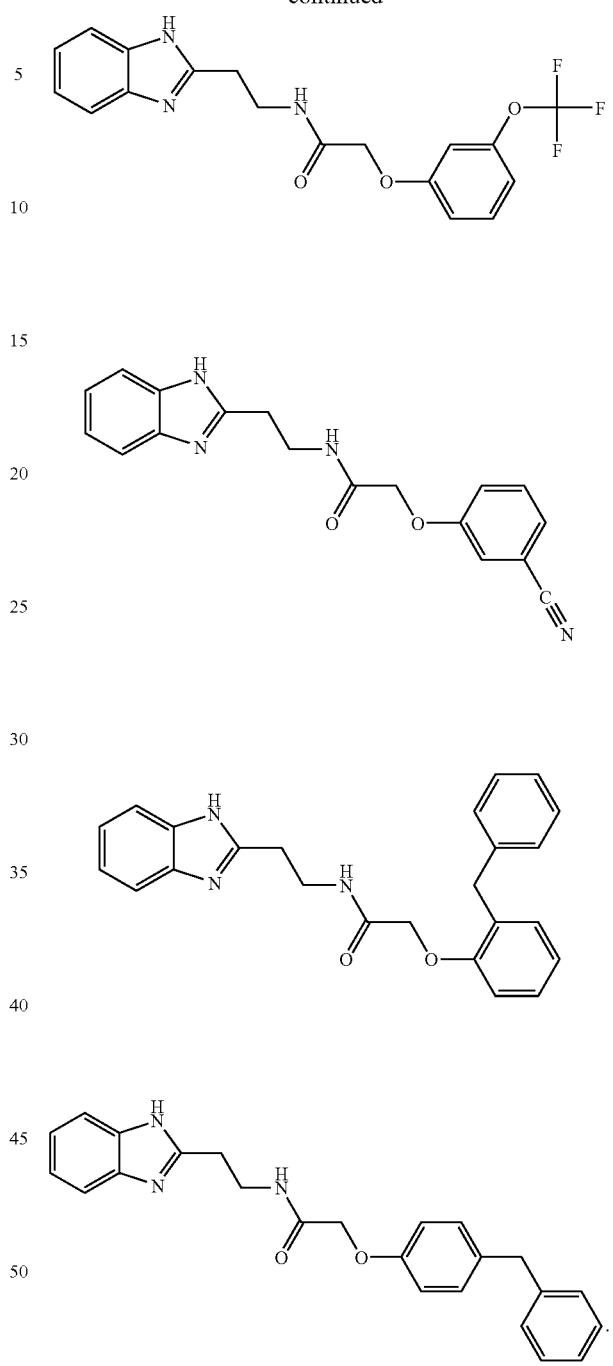
* * * * *